US010364467B2

(12) United States Patent
Lo et al.

(10) Patent No.: US 10,364,467 B2
(45) Date of Patent: Jul. 30, 2019

(54) USING SIZE AND NUMBER ABERRATIONS IN PLASMA DNA FOR DETECTING CANCER

(71) Applicant: The Chinese University of Hong Kong, Shatin, New Territories (CN)

(72) Inventors: Yuk-Ming Dennis Lo, Homantin (CN); Rossa Wai Kwun Chiu, Shatin (CN); Kwan Chee Chan, Shatin (CN); Peiyong Jiang, Shatin (CN)

(73) Assignee: The Chinese University of Hong Kong, Shatin, New Territories (HK)

( * ) Notice: Subject to any disclaimer, the term of this patent is extended or adjusted under 35 U.S.C. 154(b) by 573 days.

(21) Appl. No.: 14/994,053

(22) Filed: Jan. 12, 2016

(65) Prior Publication Data

US 2016/0201142 A1 Jul. 14, 2016

Related U.S. Application Data

(60) Provisional application No. 62/111,534, filed on Feb. 3, 2015, provisional application No. 62/102,867, filed on Jan. 13, 2015.

(51) Int. Cl.
*G06F 19/00* (2018.01)
*C12Q 1/6886* (2018.01)
(Continued)

(52) U.S. Cl.
CPC ......... *C12Q 1/6886* (2013.01); *C12Q 1/6869* (2013.01); *G16B 20/00* (2019.02);
(Continued)

(58) Field of Classification Search
CPC .. C12Q 1/6886; C12Q 1/6827; C12Q 1/6837; C12Q 2545/114; C12Q 1/6883;
(Continued)

(56) References Cited

U.S. PATENT DOCUMENTS 5,641,628 A 6/1997 Bianchi
5,879,883 A 3/1999 Benson et al.
(Continued)

FOREIGN PATENT DOCUMENTS

CN 1779688 A 5/2006
CN 1997757 A 7/2007
(Continued)

OTHER PUBLICATIONS

Agrawal et al. "Commercial landscape of non-invasive prenatal testing in the United States" Prenatal Diagnosis 2013 vol. 33 pp. 521-531.*

(Continued)

*Primary Examiner* — Mary K Zeman
(74) *Attorney, Agent, or Firm* — Kilpatrick Townsend & Stockton LLP

(57) ABSTRACT

Analysis of tumor-derived circulating cell-free DNA opens up new possibilities for performing liquid biopsies for solid tumor assessment or cancer screening. However, many aspects of the biological characteristics of tumor-derived cell-free DNA remain unclear. Regarding the size profile of plasma DNA molecules, some studies reported increased integrity of tumor-derived plasma DNA while others reported shorter tumor-derived plasma DNA molecules. We performed an analysis of the size profiles of plasma DNA in patients with cancer using massively parallel sequencing at single base resolution and in a genomewide manner. Tumor-derived plasma DNA molecules were further identified using chromosome arm-level z-score analysis (CAZA). We showed that populations of aberrantly short and long DNA molecules co-existed in the plasma of patients with cancer. The short ones preferentially carried the tumor-associated copy number aberrations. These results show the ability to use plasma DNA as a molecular diagnostic tool.

13 Claims, 34 Drawing Sheets

(51) Int. Cl.
*C12Q 1/6869* (2018.01)
*G16B 20/00* (2019.01)
*G16B 40/00* (2019.01)

(52) U.S. Cl.
CPC ........ *G16B 40/00* (2019.02); *C12Q 2600/112* (2013.01); *C12Q 2600/156* (2013.01)

(58) Field of Classification Search
CPC .......... C12Q 2537/165; C12Q 2537/16; C12Q 2545/101; C12Q 1/6809; C12Q 1/6876; C12Q 1/68; G06F 19/18; G06F 19/22; G06F 19/20; G06F 15/025; G06F 19/00; G06F 19/24; G06F 19/10; G06F 19/16; G06F 17/10; G06F 17/11; G06F 19/12; G06F 19/28; G06F 19/321; G06F 19/34; G06F 19/3418; G16H 50/20; G16H 10/40; G16H 50/30; G16H 50/70; G16H 10/60; G16H 70/20; G01N 33/574; G06N 7/005; G06N 99/005; G06Q 50/24
See application file for complete search history.

(56) References Cited

U.S. PATENT DOCUMENTS

| | | | |
|---|---|---|---|
| 6,100,029 | A | 8/2000 | Lapidus et al. |
| 6,143,496 | A | 11/2000 | Brown et al. |
| 6,214,558 | B1 | 4/2001 | Shuber et al. |
| 6,258,540 | B1 | 7/2001 | Lo et al. |
| 6,391,559 | B1 | 5/2002 | Brown et al. |
| 6,440,706 | B1 | 8/2002 | Vogelstein et al. |
| 6,566,101 | B1 | 5/2003 | Shuber et al. |
| 6,632,655 | B1 | 10/2003 | Mehta et al. |
| 6,664,056 | B2 | 12/2003 | Lo et al. |
| 6,753,147 | B2 | 6/2004 | Vogelstein et al. |
| 6,927,028 | B2 | 8/2005 | Dennis et al. |
| 7,332,277 | B2 | 2/2008 | Dhallan |
| 7,442,506 | B2 | 10/2008 | Dhallan |
| 7,476,363 | B2 | 1/2009 | Unger et al. |
| 7,645,576 | B2 | 1/2010 | Lo et al. |
| 7,655,399 | B2 | 2/2010 | Cantor et al. |
| 7,727,720 | B2 | 6/2010 | Dhallan |
| 7,838,647 | B2 | 11/2010 | Hahn et al. |
| 7,888,017 | B2 | 2/2011 | Quake et al. |
| 8,008,018 | B2 | 8/2011 | Quake et al. |
| RE44,596 | E | 11/2013 | Stroun et al. |
| 8,620,593 | B2 | 12/2013 | Lo et al. |
| 8,712,697 | B2 | 4/2014 | Struble et al. |
| 8,741,811 | B2 | 6/2014 | Lo et al. |
| 9,121,069 | B2 | 9/2015 | Lo et al. |
| 9,260,745 | B2 | 2/2016 | Rava et al. |
| 9,361,426 | B2 | 6/2016 | Akmaev et al. |
| 9,598,731 | B2 | 3/2017 | Talasaz |
| 9,732,390 | B2 | 8/2017 | Lo et al. |
| 9,758,814 | B2 | 9/2017 | Fehr et al. |
| 9,834,822 | B2 | 12/2017 | Talasaz |
| 9,840,743 | B2 | 12/2017 | Talasaz |
| 9,902,992 | B2 | 2/2018 | Talasaz et al. |
| 2001/0051341 | A1 | 12/2001 | Lo et al. |
| 2002/0164816 | A1 | 11/2002 | Quake |
| 2003/0022207 | A1 | 1/2003 | Balasubramanian et al. |
| 2003/0044388 | A1 | 3/2003 | Dennis et al. |
| 2003/0180765 | A1 | 9/2003 | Traverso et al. |
| 2003/0186255 | A1 | 10/2003 | Williams et al. |
| 2003/0204331 | A1 | 10/2003 | Whitney et al. |
| 2004/0096892 | A1 | 5/2004 | Wang et al. |
| 2004/0137470 | A1 | 7/2004 | Dhallan |
| 2004/0203037 | A1 | 10/2004 | Lo et al. |
| 2004/0209299 | A1 | 10/2004 | Pinter et al. |
| 2005/0003351 | A1 | 1/2005 | Fejgin et al. |
| 2005/0019792 | A1 | 1/2005 | McBride et al. |
| 2005/0037388 | A1 | 2/2005 | Antonarakis et al. |
| 2005/0129581 | A1 | 6/2005 | McBride et al. |
| 2005/0130176 | A1 | 6/2005 | Vogelstein et al. |
| 2005/0145496 | A1 | 7/2005 | Goodsaid et al. |
| 2005/0164241 | A1 | 7/2005 | Hahn et al. |
| 2005/0221341 | A1 | 10/2005 | Shimkets et al. |
| 2005/0221373 | A1 | 10/2005 | Enzelberger et al. |
| 2005/0252773 | A1 | 11/2005 | McBride et al. |
| 2005/0282213 | A1 | 12/2005 | Halle |
| 2006/0046258 | A1 | 3/2006 | Lapidus et al. |
| 2006/0051775 | A1 | 3/2006 | Bianchi |
| 2006/0121452 | A1 | 6/2006 | Dhallan |
| 2006/0252068 | A1 | 11/2006 | Lo et al. |
| 2006/0252071 | A1 | 11/2006 | Lo et al. |
| 2007/0059680 | A1 | 3/2007 | Kapur et al. |
| 2007/0122823 | A1 | 5/2007 | Bianchi et al. |
| 2007/0122835 | A1 | 5/2007 | Dhallan |
| 2007/0134658 | A1 | 6/2007 | Bohmer |
| 2007/0202525 | A1 | 8/2007 | Quake et al. |
| 2007/0207466 | A1 | 9/2007 | Cantor et al. |
| 2007/0212689 | A1 | 9/2007 | Bianchi et al. |
| 2007/0238105 | A1 | 10/2007 | Barrett et al. |
| 2007/0275402 | A1 | 11/2007 | Lo et al. |
| 2008/0020390 | A1 | 1/2008 | Mitchell et al. |
| 2008/0026390 | A1 | 1/2008 | Stoughton et al. |
| 2008/0038733 | A1 | 2/2008 | Bischoff et al. |
| 2008/0050739 | A1 | 2/2008 | Stoughton et al. |
| 2008/0070792 | A1 | 3/2008 | Stoughton et al. |
| 2008/0071076 | A1 | 3/2008 | Hahn et al. |
| 2008/0090239 | A1 | 4/2008 | Shoemaker et al. |
| 2008/0096216 | A1 | 4/2008 | Quake |
| 2008/0096766 | A1 | 4/2008 | Lee |
| 2008/0113358 | A1 | 5/2008 | Kapur et al. |
| 2008/0124721 | A1 | 5/2008 | Fuchs et al. |
| 2008/0138809 | A1 | 6/2008 | Kapur et al. |
| 2008/0153090 | A1 | 6/2008 | Lo et al. |
| 2008/0182261 | A1 | 7/2008 | Bianchi |
| 2008/0193927 | A1 | 8/2008 | Mann et al. |
| 2008/0213775 | A1 | 9/2008 | Brody et al. |
| 2008/0220422 | A1 | 9/2008 | Shoemaker et al. |
| 2008/0299562 | A1 | 12/2008 | Oeth et al. |
| 2009/0029377 | A1 | 1/2009 | Lo et al. |
| 2009/0170114 | A1 | 7/2009 | Quake et al. |
| 2009/0280492 | A1 | 11/2009 | Stoughton et al. |
| 2009/0291443 | A1 | 11/2009 | Stoughton et al. |
| 2010/0094562 | A1 | 4/2010 | Shohat |
| 2010/0112575 | A1 | 5/2010 | Fan et al. |
| 2010/0216151 | A1 | 8/2010 | Lapidus et al. |
| 2010/0216153 | A1 | 8/2010 | Lapidus et al. |
| 2010/0291572 | A1 | 11/2010 | Stoughton et al. |
| 2011/0003293 | A1 | 1/2011 | Stoughton et al. |
| 2011/0105353 | A1 | 5/2011 | Lo et al. |
| 2011/0171741 | A1 | 7/2011 | Wang et al. |
| 2011/0246083 | A1* | 10/2011 | Fan ..................... C12Q 1/6869 702/20 |
| 2013/0029852 | A1* | 1/2013 | Rava ..................... C12Q 1/6806 506/2 |
| 2013/0040824 | A1 | 2/2013 | Lo et al. |
| 2013/0237431 | A1 | 9/2013 | Lo et al. |
| 2013/0261984 | A1 | 10/2013 | Eberle et al. |
| 2013/0288244 | A1* | 10/2013 | Deciu ..................... C12Q 1/683 435/6.11 |
| 2014/0045181 | A1 | 2/2014 | Lo et al. |
| 2014/0080715 | A1 | 3/2014 | Lo et al. |
| 2014/0100121 | A1 | 4/2014 | Lo et al. |
| 2014/0227699 | A1 | 8/2014 | Lo et al. |
| 2014/0274740 | A1 | 9/2014 | Srinivasan et al. |
| 2014/0274752 | A1 | 9/2014 | Blume et al. |
| 2014/0364439 | A1 | 12/2014 | Wu et al. |
| 2015/0104793 | A1 | 4/2015 | Quake et al. |
| 2015/0197785 | A1 | 7/2015 | Carter et al. |
| 2015/0211070 | A1 | 7/2015 | Seligson et al. |
| 2015/0344970 | A1 | 12/2015 | Vogelstein et al. |
| 2015/0376700 | A1 | 12/2015 | Schnall-Levin et al. |
| 2016/0002739 | A1 | 1/2016 | Schütz et al. |
| 2016/0017419 | A1 | 1/2016 | Chiu et al. |
| 2016/0019338 | A1* | 1/2016 | Chudova ............... C12Q 1/6858 702/20 |
| 2016/0032396 | A1 | 2/2016 | Diehn et al. |
| 2016/0046979 | A1 | 2/2016 | Leamon et al. |
| 2016/0232290 | A1 | 8/2016 | Rava et al. |
| 2016/0239604 | A1 | 8/2016 | Chudova et al. |

(56) References Cited

U.S. PATENT DOCUMENTS

| | | |
|---|---|---|
| 2016/0275239 A1 | 9/2016 | Devogelaere et al. |
| 2016/0281154 A1 | 9/2016 | So et al. |
| 2016/0304936 A1 | 10/2016 | Ji et al. |
| 2016/0333416 A1* | 11/2016 | Babiarz ............... G06F 19/22 |
| 2016/0333417 A1 | 11/2016 | Talasaz |
| 2017/0016054 A1 | 1/2017 | Southern et al. |
| 2017/0073774 A1 | 3/2017 | Lo et al. |
| 2017/0107576 A1 | 4/2017 | Babiarz et al. |
| 2017/0145516 A1 | 5/2017 | Kopetz et al. |
| 2017/0211143 A1 | 7/2017 | Shendure et al. |
| 2017/0211153 A1 | 7/2017 | Kohli et al. |
| 2017/0218450 A1 | 8/2017 | Lo et al. |
| 2017/0218459 A1 | 8/2017 | Talasaz et al. |
| 2017/0233829 A1 | 8/2017 | Lo et al. |
| 2017/0235877 A1 | 8/2017 | Lo et al. |
| 2017/0240973 A1 | 8/2017 | Eltoukhy et al. |
| 2017/0249421 A1 | 8/2017 | Eberle et al. |
| 2017/0260590 A1 | 9/2017 | Eltoukhy et al. |
| 2017/0326238 A1* | 11/2017 | Chang ................... A61K 45/06 |
| 2017/0342477 A1 | 11/2017 | Jensen et al. |
| 2017/0342500 A1 | 11/2017 | Marquard et al. |
| 2017/0362638 A1 | 12/2017 | Chudova et al. |
| 2018/0045727 A1 | 2/2018 | Spetzler et al. |

FOREIGN PATENT DOCUMENTS

| | | |
|---|---|---|
| CN | 102369299 A | 3/2012 |
| EP | 1229135 A2 | 8/2002 |
| EP | 0994963 B1 | 5/2003 |
| EP | 2161347 A2 | 3/2010 |
| EP | 2426217 A1 | 3/2012 |
| EP | 2771483 | 9/2014 |
| EP | 3018213 A1 | 5/2016 |
| EP | 3191628 | 7/2017 |
| EP | 3194612 | 7/2017 |
| EP | 3218523 | 9/2017 |
| JP | 2002272497 A | 9/2002 |
| JP | 2007515947 A | 6/2007 |
| KR | 10-2002-0064298 | 8/2002 |
| KR | 20040102024 A | 12/2004 |
| RU | 2249820 C1 | 4/2005 |
| WO | 03020974 A2 | 3/2003 |
| WO | 03030823 A2 | 4/2003 |
| WO | 03048295 A1 | 6/2003 |
| WO | 03074723 A2 | 9/2003 |
| WO | 2004016758 A2 | 2/2004 |
| WO | 2004046370 A2 | 6/2004 |
| WO | 2004065629 A1 | 8/2004 |
| WO | 2004078999 A1 | 9/2004 |
| WO | 2004079011 A1 | 9/2004 |
| WO | 2005023091 A2 | 3/2005 |
| WO | 2005035725 A2 | 4/2005 |
| WO | 2005039389 A2 | 5/2005 |
| WO | 2005118852 A2 | 12/2005 |
| WO | 2006010610 A2 | 2/2006 |
| WO | 2006108101 A2 | 10/2006 |
| WO | 2007028155 A2 | 3/2007 |
| WO | 2007044091 A2 | 4/2007 |
| WO | 2007075836 A2 | 7/2007 |
| WO | 2007092473 A2 | 8/2007 |
| WO | 2007100911 A2 | 9/2007 |
| WO | 2007132166 A2 | 11/2007 |
| WO | 2007132167 A2 | 11/2007 |
| WO | 2007147073 A2 | 12/2007 |
| WO | 2007147074 A2 | 12/2007 |
| WO | 2007147076 A2 | 12/2007 |
| WO | 2008050734 A1 | 5/2008 |
| WO | 2008150368 A1 | 12/2008 |
| WO | 2009013492 A1 | 1/2009 |
| WO | 2009019455 A2 | 2/2009 |
| WO | 2009037690 A1 | 3/2009 |
| WO | 2009/051842 A2 | 4/2009 |
| WO | 2010112316 A1 | 10/2010 |
| WO | 2011053790 A2 | 5/2011 |
| WO | 2011054936 A1 | 5/2011 |
| WO | 2011090556 A1 | 7/2011 |
| WO | 2012071621 A1 | 6/2012 |
| WO | 2013052907 A2 | 4/2013 |
| WO | 2013060762 A1 | 5/2013 |
| WO | 2014039556 A1 | 3/2014 |
| WO | 2014043763 A1 | 3/2014 |
| WO | 2016015058 A2 | 1/2016 |
| WO | 2016028316 A1 | 2/2016 |
| WO | 2016040901 A1 | 3/2016 |
| WO | 2016077709 A1 | 5/2016 |
| WO | 2016/116033 A1 | 7/2016 |
| WO | 2016179049 A1 | 11/2016 |
| WO | 2016179530 A1 | 11/2016 |
| WO | 2016183106 A1 | 11/2016 |
| WO | 2017009372 A2 | 1/2017 |
| WO | 2017027391 A2 | 2/2017 |
| WO | 2017062867 A1 | 4/2017 |
| WO | 2017070497 A1 | 4/2017 |
| WO | 2018081130 A1 | 5/2018 |

OTHER PUBLICATIONS

Chan et al. 2013 Clinical Chemistry 59:1 211-224.*
Schwarzenbach et al. 2011 Nature Reviews Cancer vol. 11 p. 426-437.*
Lun et al. 2008 PNAS vol. 105 No. 50, 19920-19925.*
Extended European Search Report dated May 25, 2018 in EP Patent Application No. 17209781.8. 6 pages.
Fan, H. Christina et al.; "Analysis of the Size Distributions of Fetal and Maternal Cell-Free DNA by Paired-End Sequencing"; Clinical Chemistry; 2010; vol. 56, No. 8; pp. 1279-1286.
Extended European Search Report dated Jun. 4, 2018 in EP Patent Application No. 16737075.8. 13 pages.
Yu, Stephanie C. Y. et al.; "Size-based molecular diagnostics using plasma DNA for noninvasive prenatal testing"; PNAS; 2014; vol. 111, No. 23; pp. 8583-8588.
Jiang, Peiyong et al.; "Lengthening and shortening of plasma DNA in hepatocellular carcinoma patients"; PNAS; Mar. 17, 2015; 112(11); E1317-E1325; published online Feb. 2, 2015; doi: 10.1073/pnas.1500076112; 9 pages.
Mouliere, Florent et al.; "High Fragmentation Characterizes Tumour-Derived Circulating DNA"; PLoS One; 2011; vol. 6, Issue 9; e23418; 10 pages.
Chan, K.C. Allen et al.; "Cancer Genome Scanning in Plasma: Detection of Tumor-Associated Copy Number Aberrations, Single-Nucleotide Variants, and Tumoral Heterogeneity by Massively Parallel Sequencing"; Clinical Chemistry; vol. 59, Issue 1; pp. 211-224.
Leary, Rebecca J. et al.; "Detection of Chromosomal Alterations in the Circulation of Cancer Patients with Whole-Genome Sequencing"; Science Translational Medicine; 2012; vol. 4, Issue 162; 162ra154; 13 pages.
International Search Report and Written Opinion dated Apr. 22, 2016 in PCT Application No. PCT/CN2016/070785. 11 pages.
Communication of a notice of opposition dated Oct. 12, 2018 in EP Patent Application No. 13757943.9. 18 pages.
Ellinger, Jörg et al.; "Cell-free circulating DNA: diagnostic value in patients with testicular germ cell cancer;" Journal of Urology; Jan. 1, 2009; vol. 181, No. 1; pp. 363-371.
Chan, K.C. Allen et al.; "Size Distributions of Maternal and Fetal DNA in Maternal Plasma"; Clinical Chemistry; 2004; vol. 50, No. 1; pp. 88-92.
Gang, Feng et al.; "Prediction of Clear Cell Renal Cell Carcinoma by Integrity of Cell-free DNA in Serum"; Urology; Feb. 2010; vol. 75, Issue 2; pp. 262-265.
Wang, Brant G. et al.; "Increased Plasma DNA Integrity in Cancer Patients"; Cancer Research; Jul. 15, 2003; vol. 63, No. 14; pp. 3966-3968 (4 pages).
Lo, Y.M. Dennis et al.; "Maternal Plasma DNA Sequencing Reveals the Genome-Wide Genetic and Mutational Profile of the Fetus"; Science Translational Medicine; Published Dec. 8, 2010; vol. 2, Issue 61; 61ra91; pp. 1-13; plus 60 pages of "Supporting Online Material" (73 total pages).

(56) References Cited

OTHER PUBLICATIONS

Maron, Jill L. et al.; "Prenatal Diagnosis Using Cell-Free Nucleic Acids in Maternal Body Fluids: A Decade of Progress"; American Journal of Medical Genetics Part C: Seminars in Medical Genetics; 2007; vol. 145C, Issue 1; pp. 5-17.
Tsui, Nancy B.Y. et al.; "High Resolution Size Analysis of Fetal DNA in the Urine of Pregnant Women by Paired-End Massively Parallel Sequencing"; PLoS One; 2012; Epub Oct. 31, 2012; e48319; doi: 10.1371/journal.pone.0048319; vol. 7, Issue 10; 7 pages.
Mouliere, Florent et al.; "The importance of examining the proportion of circulating DNA originating from tumor, microenvironment and normal cells in colorectal cancer patients"; Expert Opinion on Biological Therapy; 2012; vol. 12, Supplement 1; pp. S209-S215 (8 pages).
Chan, K.C. Allen et al.; "Persistent Aberrations in Circulating DNA Integrity after Radiotherapy Are Associated with Poor Prognosis in Nasopharyngeal Carcinoma Patients"; Clinical Cancer Research; Jul. 1, 2008; vol. 14, No. 13; pp. 4141-4145 (6 pages).
English translation of Notice of Allowance dated Oct. 25, 2018 in KR Patent Application No. 10-2017-7022238. 1 page.
Devonshire, Alison S. et al.; "Towards standardisation of cell-free DNA measurement in plasma: controls for extraction efficiency, fragment size bias and quantification"; Analytical and Bioanalytical Chemistry; Oct. 2014; vol. 406, No. 26; pp. 6499-6512.
Elshimali, Yahya I. et al.; "The Clinical Utilization of Circulating Cell Free DNA (CCFDNA) in Blood of Cancer Patients"; International Journal of Molecular Sciences; 2013; vol. 14, No. 9; pp. 18925-18958.
Agarwal, Ashwin et al.; "Commercial landscape of noninvasive prenatal testing in the United States"; Prenatal Diagnosis; 2013; vol. 33, No. 6; pp. 521-531.
Landau, Dan A. et al.; "Evolution and Impact of Subclonal Mutations in Chronic Lymphocytic Leukemia"; Cell; Feb. 14, 2013; vol. 152, No. 4; pp. 714-726.
Landau, Dan A. et al.; "Mutations driving CLL and their evolution in progression and relapse"; Nature; Oct. 22, 2015; vol. 526; pp. 525-530.
Separation of RNA & DNA by Gel Filtration Chromatography, Edvotek, 1987, pp. 1-27.
Solexa Genome Analysis System, Solexa Advancing Genetic Analysis One Billion Bases at a Time, 2006, 2 pages.
Australian Application No. 2008278839, First Examiner Report dated May 10, 2012, 3 pages.
Australian Application No. 2013200581, Second Examination Report dated Dec. 13, 2013, 5 pages.
Australian Application No. 2013202132, First Examination Report dated Jun. 5, 2014, 4 pages.
Australian Application No. 2013202141, First Examiner Report dated Jun. 5, 2014, 12 pages.
Australian Application No. 2013202157, First Examiner Report dated Jun. 5, 2014, 12 pages.
Australian Application No. 2013202160, First Examiner Report dated Jun. 5, 2014, 13 pages.
Australian Application No. 2013229186, First Examiner Report dated Dec. 1, 2015, 5 pages.
Australian Application No. 2015271883, First Examiner Report dated Dec. 14, 2016, 4 pages.
Australian Application No. 2017201258, Second Examination Report dated Sep. 3, 2018, 5 pages.
Bauer et al., A Prospective Analysis of Cell-Free Fetal DNA Concentration in Maternal Plasma as an Indicator for Adverse Pregnancy Outcome, Prenatal Diagnosis, vol. 26, No. 9, Jul. 11, 2006, pp. 831-836.
Bentley, Whole-Genome Re-Sequencing, Current Opinion in Genetics & Development, vol. 16, No. 6, 2006, pp. 545-552.
Bianchi et al., Large Amounts of Cell-free Fetal DNA Are Present in Amniotic Fluid, Clinical Chemistry, vol. 47, No. 10, Oct. 2001, pp. 1867-1869.
Bischoff et al., Cell-Free Fetal DNA and Intact Fetal Cells in Maternal Blood Circulation: Implications for First and Second Trimester Non-Invasive Prenatal Diagnosis, Human Reproduction Update, vol. 8, No. 6, Nov. 2002, pp. 492-500.
Braslavsky et al., Sequence Information can be Obtained from Single DNA Molecules, PNAS, vol. 100, No. 7, Apr. 1, 2003, pp. 3960-3964.
Brenner et al., Gene Expression Analysis by Massively Parallel Signature Sequencing (MPSS) on Microbead Arrays, Nature Biotechnology, vol. 18, Jun. 2000, pp. 630-634.
Canadian Application No. 2,694,007, Office Action dated Apr. 10, 2017, 5 pages.
Canadian Application No. 2,973,025, Office Action dated Aug. 14, 2018, 4 pages.
Campbell et al., Identification of Somatically Acquired Rearrangements in Cancer Using Genome-Wide Massively Parallel Paired-End Sequencing, Nature Genetics, vol. 40, No. 6, Jun. 2008, pp. 722-729.
Chan et al., DNA Mapping Using Microfluidic Stretching and Single-Molecule Detection of Fluorescent Site-Specific Tags, Genome Research, vol. 14, 2004, pp. 1137-1146.
Chan et al., Hypermethylated RASSF1A in Maternal Plasma: A Universal Fetal DNA Marker that Improves the Reliability of Noninvasive Prenatal Diagnosis, Clinical Chemistry, vol. 52, No. 12, Dec. 31, 2006, pp. 2211-2218.
Chan et al., Molecular Characterization of Circulating EBV DNA in the Plasma of Nasopharyngeal Carcinoma and Lymphoma Patients, Cancer Research, vol. 63, No. 9, May 1, 2003, pp. 2028-2032.
Chim et al., Detection of Placental Epigenetic Signature of Maspin Gene in Material Plasma, XP-002355638, PNAS, vol. 102, No. 41, Oct. 11, 2005, pp. 14753-14758.
Chiu et al., Application of Fetal DNA in Maternal Plasma for Noninvasive Prenatal Diagnosis, Expert Review of Molecular Diagnostics, vol. 2, No. 1, Jan. 2002, pp. 32-40.
Chiu et al., Effects of Blood-Processing Protocols on Fetal and Total DNA Quantification in Maternal Plasma, Clinical Chemistry, vol. 47, No. 9, Sep. 2001, pp. 1607-1613.
Chiu et al., Non-Invasive Prenatal Assessment of Trisomy 21 by Multiplexed Maternal Plasma DNA Sequencing: Large Scale Validity Study, BMJ, vol. 342, No. c7401, Jan. 11, 2011, pp. 1-9.
Chiu et al., Non-Invasive Prenatal Diagnosis by Single Molecule Counting Technologies, Trends in Genetics, vol. 25, No. 7, Jul. 1, 2009, pp. 324-331.
Chiu et al., Noninvasive Prenatal Diagnosis of Fetal Chromosomal Aneuploidy by Massively Parallel Genomic Sequencing of DNA in Maternal Plasma, Proceedings of the National Academy of Sciences, vol. 105, No. 51, Dec. 23, 2008, pp. 20458-20463.
Cirigliano et al., Clinical Application of Multiplex Quantitative Fluorescent Polymerase Chain Reaction (QF-PCR) for the Rapid Prenatal Detection of Common Chromosome Aneuploidies, Molecular Human Reproduction, vol. 7, No. 10, 2001, pp. 1001-1006.
Chinese Application No. 200880108126.3, Office Action dated Aug. 27, 2012, 3 pages.
Chinese Application No. 200880108126.3, Office Action dated Dec. 31, 2011, 3 pages.
Chinese Application No. 200880108126.3, Office Action dated May 28, 2013, 3 pages.
Dear, One by One: Single Molecule Tools for Genomics, Briefings in Functional Genomics and Proteomics, vol. 1, No. 4, Jan. 2003, pp. 397-416.
Della Ragione et al., Differential DNA Methylation as a Tool for Noninvasive Prenatal Diagnosis (NIPD) of X Chromosome Aneuploidies, The Journal of Molecular Diagnostics, vol. 12, No. 6, Nov. 1, 2010, pp. 797-807.
Dhallan et al., A Non-Invasive Test for Prenatal Diagnosis Based on Fetal DNA Present in Maternal Blood: A Preliminary Study, The Lancet, vol. 369, Feb. 2, 2007, pp. 474-481.
Diehl et al., Detection and Quantification of Mutations in the Plasma of Patients with Colorectal Tumors, Proceedings of the National Academy of Sciences, vol. 102, No. 45, Nov. 8, 2005, pp. 16368-16373.
Ding et al., MS Analysis of Single-Nucleotide Differences in Circulating Nucleic Acids: Application to Noninvasive Prenatal

(56) References Cited

OTHER PUBLICATIONS

Diagnosis, Proceedings of the National Academy of Sciences of the United States (PNAS), National Academy of Science US, vol. 101, No. 29, Jul. 20, 2004, pp. 10762-10767.
Ding et al., Other Applications of Single Nucleotide Polymorphisms, Trends in Biotechnology, Elsevier Publications, Cambridge, GB, vol. 25, No. 7, Jun. 14, 2007, pp. 279-283.
Dressman et al., Transforming Single DNA Molecules into Fluorescent Magnetic Particles for Detection and Enumeration of Genetic Variations, Proceedings of the National Academy of Sciences of the United States of America, vol. 100, No. 15, Jul. 22, 2003, pp. 8817-8822.
Eurasian Application No. 201201551, Search Report dated May 15, 2013, 2 pages.
El Karoui et al., Getting more from digital SNP data, Statistics in Medicine, vol. 25, Jan. 1, 2006, pp. 3124-3133.
European Application No. 07763674.4, Extended European Search Report dated Jul. 31, 2009, 10 pages.
European Application No. 07763674.4, Office Action dated Sep. 23, 2009, 1 page.
European Application No. 07763674.4, Office Action dated Dec. 21, 2010, 11 pages.
European Application No. 07784444.7, Extended European Search Report dated Dec. 22, 2009, 9 pages.
European Application No. 07798579.4, Extended European Search Report dated Dec. 21, 2009, 8 pages.
European Application No. 07798580.2, Extended European Search Report dated Dec. 22, 2009, 6 pages.
European Application No. 08776038.5, Exam Report dated Aug. 3, 2010, 7 pages.
European Application No. 08776038.5, Exam Report dated Nov. 22, 2011, 7 pages.
European Application No. 08776038.5, Exam Report dated Nov. 12, 2012, 9 pages.
European Application No. 08776043.5, Office Action dated Jul. 13, 2010, 6 pages.
European Application No. 12173422.2, Extended European Search Report dated Nov. 23, 2012, 10 pages.
European Application No. 12175754.6, Extended European Search Report dated Nov. 23, 2012, 12 pages.
European Application No. 12180129.4, Extended European Search Report dated Sep. 9, 2014, 15 pages.
European Application No. 12180133.6, Extended European Search Report dated Jun. 25, 2014, 10 pages.
European Application No. 12180138.5, Partial European Search Report dated Dec. 10, 2014, 12 pages.
European Application No. 13757943.9, Extended European Search Report dated Sep. 7, 2015, 7 pages.
European Application No. 14193706.0, Extended European Search Report dated Mar. 18, 2015, 5 pages.
European Application No. 14193706.0, Office Action dated Nov. 3, 2015, 4 pages.
European Application No. 17202838.3, Extended European Search Report dated Jan. 19, 2018, 5 pages.
European Application No. 7784442.1, Extended European Search Report dated Nov. 9, 2009, 9 pages.
Fan et al., Detection of Aneuploidy with Digital PCR, Department of Bioengineering, Stanford University and Howard Hughes Medical Institute, May 8, 2007, 14 pages.
Fan et al., Detection of Aneuploidy with Digital Polymerase Chain Reaction, Analytical Chemistry, American Chemical Society, vol. 79, No. 19, Oct. 1, 2007, pp. 7576-7579.
Fan et al., Microfluidic Digital PCR Enables Rapid Prenatal Diagnosis of Fetal Aneuploidy, American Journal of Obstetrics & Gynecology, May 2009, pp. 543e1-543e7.
Fan et al., Noninvasive Diagnosis of Fetal Aneuploidy by Shotgun Sequencing DNA from Maternal Blood, Proceedings National Academy of Sciences of the USA, vol. 105, No. 42, Oct. 21, 2008, pp. 16266-16271.
Fan et al., Sensitivity of Noninvasive Prenatal Detection of Fetal Aneuploidy from Maternal Plasma Using Shotgun Sequencing is Limited only by Counting Statistics, PLoS One, vol. 5, No. 5, e10439, Mar. 2010, pp. 1-7.
Feinberg et al., A Technique for Radiolabeling DNA Restriction Endonuclease Fragments to High Specific Activity, Analytical Biochemistry, vol. 132, Issue 1, Jul. 1, 1983, pp. 6-13.
Giurato et al., An Accurate Pipeline for Analysis of NGS Data of Small Non-Coding RNA, EMBnet.Journal, vol. 18, 2012, pp. 100-101.
Green et al., Analysis of One Million Base Pairs of Neanderthal DNA, Nature, vol. 444, Issue 7117, Nov. 16, 2006, pp. 330-336.
Harris et al., Single-Molecule DNA Sequencing of a Viral Genome, Science, vol. 320, Issue 5872, Apr. 4, 2008, pp. 106-109.
Hong et al., A Nanoliter-Scale Nucleic Acid Processor with Parallel Architecture, Nature Biotechnology, vol. 22, Issue 4, Apr. 14, 2004, pp. 435-439.
Hong et al., Molecular Biology on a Microfluidic Chip, Journal of Physics: Condensed Matter, vol. 18, Apr. 19, 2006, pp. S691-S701.
Hromadnikova et al., Quantitative Analysis of DNA Levels in Maternal Plasma in Normal and Down Syndrome Pregnancies, BMC Pregnancy and Childbirth, vol. 2, No. 4, May 28, 2002, pp. 1-5.
Jahr et al., DNA Fragments in the Blood Plasma of Cancer Patients: Quantitations and Evidence for their Origin from Apoptotic and Necrotic Cells, Cancer Research, vol. 61, Issue 4, Feb. 15, 2001, pp. 1659-1665.
Jiang et al., Increased Plasma DNA Integrity Index in Head and Neck Cancer Patients, International Journal of Cancer, vol. 119, Issue 11, Dec. 1, 2006, pp. 2673-2676.
Japanese Application No. 2010-517480, Notice of Reasons for Rejection dated Jun. 25, 2013, 13 pages (6 pages for the original document and 7 pages for the English translation).
Japanese Application No. 2013-267526, Office Action dated Jun. 13, 2017, 7 pages.
Japanese Application No. 2014-560451, Office Action dated Feb. 23, 2016, 10 pages.
Japanese Application No. 2017-000134, Office Action dated Dec. 12, 2017, 6 pages.
Kazakov et al., Extracellular DNA in the Blood of Pregnant Women, Tsitologiia, vol. 37, No. 3, 1995, pp. 232-236.
Kimura et al., The DYRK1A Gene, Encoded in Chromosome 21 Down Syndrome Critical Region, Bridges Between Beta-Amyloid Production and Tau Phosphorylation in Alzheimer Disease, Human Molecular Genetics, vol. 16, Issue 1, Jan. 2007, pp. 15-23.
Korbel et al., Paired-End Mapping Reveals Extensive Structural Variation in the Human Genome, Science, vol. 318, No. 5849, Oct. 19, 2007, pp. 420-426.
Korshunova et al., Massively Parallel Bisulphate Pyrosequencing Reveals the Molecular Complexity of Breast Cancer-Associated Cytosine-Methylation Patterns Obtained from Tissue and Serum DNA, Genome Research, vol. 18, 2008, pp. 19-29.
Korean Application No. 10-2016-7021214, Office Action dated Nov. 21, 2016, 12 pages.
Laframboise et al., Allele-Specific Amplification in Cancer Revealed by SNP Array Analysis, PLoS Computational Biology, vol. 1, Issue 6, e65, Nov. 2005, pp. 0507-0517.
Lapaire et al., Array-CGH Analysis of Cell-Free Fetal DNA in 10 mL of Amniotic Fluid Supernatant, Prenatal Diagnosis, vol. 27, No. 7, Jul. 2007, pp. 616-621.
Lapaire et al., Cell-Free Fetal DNA in Amniotic Fluid: Unique Fragmentation Signatures in Euploid and Aneuploid Fetuses, Clinical Chemistry, vol. 53, No. 3, Mar. 2007, pp. 405-411.
Lapaire et al., Larger Columns and Change of Lysis Buffer Increase the Yield of Cell-Free DNA Extracted from Amniotic Fluid, Clinical Chemistry, vol. 52, No. 1, Jan. 2006, pp. 156-157.
Larrabee et al., Microarray Analysis of Cell-Free Fetal DNA in Amniotic Fluid: A Prenatal Molecular Karyotype, XP-002413186, The American Society of Human Genetics, vol. 75, No. 3, Sep. 1, 2004, pp. 485-491.
Lecoeur, Nuclear Apoptosis Detection by Flow Cytometry: Influence of Endogenous Endonucleases, Experimental Cell Research, vol. 277, No. 1, Jul. 1, 2002, pp. 1-14.

(56) References Cited

OTHER PUBLICATIONS

Leutwyler, Mapping Chromosomes 21, Scientific American, May 15, 2000, pp. 1-5.
Li et al., Size Separation of Circulatory DNA in Maternal Plasma Permits Ready Detection of Fetal DNA Polymorphisms, Clinical Chemistry, Molecular Diagnostics and Genetics, vol. 50, No. 6, Jun. 2004, pp. 1002-1011.
Liu et al., Decoding Circulating Nucleic Acids in Human Serum Using Microfluidic Single Molecule Spectroscopy, Journal of the American Chemical Society, vol. 132, No. 16, Apr. 5, 2010, pp. 5793-5798.
Lo et al., Digital PCR for the Molecular Detection of Fetal Chromosomal Aneuploidy, PNAS, vol. 104, No. 32, Aug. 7, 2007, pp. 13116-13121.
Lo et al., Fetal DNA in Maternal Plasma, Annals of the New York Academy of Sciences, vol. 906, Apr. 2000, pp. 141-147.
Lo, Noninvasive Prenatal Detection of Fetal Chromosomal Aneuploidies by Maternal Plasma Nucleic Acid Analysis: A Review of the Current State of the Art, BJOG: An International Journal of Obstetrics & Gynaecology, vol. 116, No. 2, Jan. 2009, pp. 152-157.
Lo et al., Noninvasive Prenatal Diagnosis of Fetal Chromosomal Aneuploidies by Maternal Plasma Nucleic Acid Analysis, Clinical Chemistry, vol. 54, Issue 3, Feb. 2008, pp. 461-466.
Lo et al., Plasma Placental RNA Allelic Ratio Permits Noninvasive Prenatal Chromosomal Aneuploidy Detection, Nature Medicine, vol. 13, Issue 2, Feb. 1, 2007, pp. 1-6.
Lo et al., Prenatal Diagnosis: Progress Through Plasma Nucleic Acids, Nature Reviews Genetics, vol. 8, No. 1, Jan. 2007, pp. 71-77.
Lo et al., Presence of Fetal DNA in Maternal Plasma and Serum, The Lancet, vol. 350, No. 9076, Aug. 16, 1997, pp. 485-487.
Lo et al., Quantitative Analysis of Fetal DNA in Maternal Plasma and Serum: Implications for Noninvasive Prenatal Diagnosis, AJHG, vol. 62, Issue 4, Apr. 1998, pp. 768-775.
Lun et al., Microfluidics Digital PCR Reveals a Higher than Expected Fraction of Fetal DNA in Maternal Plasma, Clinical Chemistry, vol. 54, Issue 10, Oct. 2008, pp. 1664-1672.
Maloney et al., Microchimerism of Maternal Origin Persists into Adult Life, Journal Clinical Investigation, vol. 104, Jul. 1999, pp. 41-47.
Mann et al., Strategies for the Rapid Prenatal Diagnosis of Chromosome Aneuploidy, European Journal of Human Genetics, vol. 12, 2004, pp. 907-915.
Marcus et al., Microfluidic Single-Cell mRNA Isolation and Analysis, American Chemical Society, Anal Chem, vol. 78, No. 9, Mar. 2006, pp. A-F.
Marcus et al., Parallel Picoliter RT-PCR Assays Using Microfluidics, Analytical Chemistry, vol. 78, No. 3, Feb. 1, 2006, pp. 956-958.
Margulies et al., Genome Sequencing in Microfabricated High-density Picolitre Reactors, Nature, vol. 437, No. 7057, Sep. 15, 2005, pp. 376-380.
Meyer et al., Analysis of the Transcriptional Complexity of *Arabidopsis thaliana* by Massively Parallel Signature Sequencing, Nature Biotechnology, vol. 22, No. 8, Aug. 2004, pp. 1006-1011.
Meyer et al., From Micrograms to Picograms: Quantitative PCR Reduces the Material Demands of High-Throughput Sequencing, Nucleic Acids Research, vol. 36, No. 1, e5, Jan. 1, 2008, pp. 1-6.
Muller et al., Identification of Loss of Heterozygosity on Circulating Free DNA in Peripheral Blood of Prostate Cancer Patients: Potential and Technical Improvements, Clinical Chemistry, vol. 54, Issue 4, Apr. 2008, pp. 688-696.
Ng et al., The Concentration of Circulating Corticotropin-Releasing Hormone mRNA in Maternal Plasma Is Increased in Preeclampsia, Clinical Chemistry, vol. 49, Issue 5, May 2003, pp. 727-731.
Noonan et al., Sequencing and Analysis of Neanderthal Genomic DNA, Science, vol. 314, Issue 5802, Nov. 17, 2006, pp. 1113-1118.
Nygren et al., Quantification of Fetal DNA by Use of Methylation-Based DNA Discrimination, Clinical Chemistry, vol. 56, Issue 10, Oct. 2010, pp. 1627-1635.
New Zealand Application No. 600407, Examination Report dated Jun. 5, 2012, 2 pages.
Old et al., Candidate Epigenetic Biomarkers for Non-Invasive Prenatal Diagnosis of Down Syndrome, Reproductive BioMedicine Online, vol. 15, No. 2, Jun. 21, 2007, pp. 227-235.
Ottesen et al., Microfluidic Digital PCR Enables Multigene Analysis of Individual Environmental Bacteria, Science, vol. 314, Issue 5804, Dec. 1, 2006, pp. 1464-1467.
Palomaki et al., DNA Sequencing of Maternal Plasma to Detect Down Syndrome: An International Clinical Validation Study, Genetics in Medicine, vol. 13, No. 11, Nov. 2011, pp. 913-920.
Panhard et al., Constructions of a Global Score Quantifying Allelic Imbalance Among Biallelic SIDP Markers in Bladder Cancer, Statistics in Medicine, vol. 22, Sep. 2003, pp. 3771-3779.
Papageorgiou et al., Fetal-Specific DNA Methylation Ratio Permits Noninvasive Prenatal Diagnosis of Trisomy 21, Nature Medicine, vol. 17, No. 4, Apr. 2011, pp. 510-513.
International Application No. PCT/EP2010/066935, International Search Report and Written Opinion dated Feb. 23, 2011, 10 pages.
International Application No. PCT/GB2008/002524, International Search Report and Written Opinion dated Oct. 30, 2008, 28 pages.
International Application No. PCT/GB2008/002530, International Search Report and Written Opinion dated Dec. 15, 2008, 14 pages.
International Application No. PCT/IB2012/000015, International Search Report and Written Opinion dated Apr. 27, 2012, 9 pages.
International Application No. PCT/IB2013/000312, International Search Report and Written Opinion dated Jun. 18, 2013, 13 pages.
International Application No. PCT/US2007/003209, International Preliminary Report on Patentability dated Oct. 14, 2008, 7 pages.
International Application No. PCT/US2007/003209, International Search Report and Written Opinion dated Sep. 18, 2008, 7 pages.
International Application No. PCT/US2009/057136, International Search Report and Written Opinion dated Mar. 16, 2010, 14 pages.
International Application No. PCT/US2010/055655, International Search Report and Written Opinion dated Apr. 20, 2011, 20 pages.
Peter et al., Cell-Free DNA Fragmentation Patterns in Amniotic Fluid Identify Genetic Abnomnalities and Changes Due to Storage, Diagnostic Molecular Pathology, vol. 17, No. 3, Sep. 2008, pp. 185-190.
Pohl et al., Principle and Applications of Digital PCR, Expert Review of Molecular Diagnostics, vol. 4, Issue 1, 2004, pp. 41-47.
Poon et al., Differential DNA Mehtylation between Fetus and Mother as a Strategy for Detecting Fetal DNA in Maternal Plasma, Clinical Chemistry, vol. 48, No. 1, 2002, pp. 35-41.
Rahil et al., Rapid Detection of Common Autosomal Aneuploidies by Quantitative Fluorescent PCR on Uncultured Amniocytes, European Journal of Human Genetics, vol. 10, 2002, pp. 462-466.
Reed et al., Non-Invasive Determination of the Paternal HLA Haplotype of a Fetus Using Kinetic PCR to Detect Fetal Microchimerism in Maternal Plasma, Bone Marrow Transplantation, vol. 29, No. 6, 2002, pp. 527-529.
Reinartz et al., Massively Parallel Signature Sequencing (MPSS) as a Tool for In-Depth Quantitative Gene Expression Profiling in All Organisms, Briefings in Functional Genomics and Proteomics, vol. 1, Issue 1, Feb. 1, 2002, pp. 95-104.
Ruan et al., Fusion Transcripts and Transcribed Retrotransposed Loci Discovered Through Comprehensive Transcriptome Analysis Using Paired-End DiTags (PETs), Genome Research, vol. 17, 2007, pp. 828-838.
Rubben et al., Somatic Deletion of the NFI Gene in a Neurofibromatosis Type I-associated Malignant Melanoma Demonstrated by Digital PCR, Molecular Cancer, vol. 5, No. 36, Sep. 10, 2006, 9 pages.
Salani et al., Measurement of Cyclin E Genomic Copy Number and Strand Length in Cell-Free DNA Distinguish Malignant Versus Benign Effusions, Cancer Research, vol. 13, Issue 19, Oct. 1, 2007, pp. 5805-5809.
Sehnert et al., Optimal Detection of Fetal Chromosomal Abnormalities by Massively Parallel DNA Sequencing of Cell-Free Fetal DNA From Maternal Blood, Clinical Chemistry, vol. 57, Issue 7, Apr. 25, 2011, pp. 1042-1049.
Seo et al., Four-Color DNA Sequencing by Synthesis on a Chip Using Photocleavable Fluorescent Nucleotides, Proc. Natl. Acad. Sci USA, vol. 102, No. 17, Apr. 26, 2005, pp. 5926-5931.
Singapore Application No. 2012054102, Written Opinion and Search Report dated Apr. 17, 2015, 9 pages.

(56) References Cited

OTHER PUBLICATIONS

Shendure et al., Next-Generation DNA Sequencing, Nature Biotechnology, vol. 26, No. 10, Oct. 2008, pp. 1135-1145.
Shih et al., Evidence that Genetic Instability Occurs at an Early Stage of Colorectal Tumorigenesis, Cancer Research, vol. 61, Feb. 1, 2001, pp. 818-822.
Smith et al., Using Quality Scores and Longer Reads Improves Accuracy of Solexa Read Mapping, BMC Bioinformatics, vol. 9, No. 128, Feb. 2008, pp. 1-8.
Soni et al., Progress Toward Ultrafast DNA Sequencing Using Solid-State Nanopores, Clinical Chemistry, vol. 53, No. 11, 2007, pp. 1996-2001.
Sozzi et al., Detection of Microsatellite Alterations in Plasma DNA of Non-Small Cell Lung Cancer Patients: A Prospect for Early Diagnosis, Clinical Cancer Research, vol. 5, Oct. 1999, pp. 2689-2692.
Sparks et al., Noninvasive Prenatal Detection and Selective Analysis of Cell-Free DNA Obtained from Maternal Blood: Evaluation for Trisomy 21 and Trisomy 18, American Journal of Obstetrics & Gynecology, vol. 206, No. 4, Apr. 2012, pp. 319.e1-319.e9.
Stolovitzky et al., Statistical Analysis of MPSS Measurements: Application to the Study of LPS-activated Macrophage Gene Expression, PNAS, vol. 102, No. 5, Feb. 1, 2005, pp. 1402-1407.
Swarup et al., Circulating (Cell-free) Nucleic Acids—a Promising, Non-invasive Tool for Early Detection of Several Human Diseases, FEBS Letters, vol. 581, Feb. 2, 2007, pp. 795-799.
Sykes et al., Quantitation of Targets for PCR by use of Limiting Dilution, BioTechniques, vol. 13, No. 3, Sep. 1992, pp. 444-449.
Taback et al., Prognostic Significance of Circulating Microsatellite Markers in the Plasma of Melanoma Patients, Cancer Research, vol. 61, No. 15, Aug. 1, 2001, pp. 5723-5726.
Tanaka et al., Genome-Wide Expression Profiling of Mid-Gestation Placenta and Embryo Using a 15,000 Mouse Developmental cDNA Microarray, PNAS, vol. 97, No. 16, Aug. 1, 2000, pp. 9127-9132.
Thornley, Analysis of Trace Data from Fluorescence Based Sanger Sequencing, Thesis, University of London Imperial College of Science, Technology and Medicine Department of Computing, 1997, 171 pages.
Tong et al., Epigenetic-Genetic Chromosome Dosage Approach for Fetal Trisomy 21 Detection Using an Autosomal Genetic Reference Marker, PLOS One, vol. 5, No. 12, e15244, Dec. 2010, 9 pages.
Tong et al., Noninvasive Prenatal Detection of Fetal Trisomy 18 by Epigenetic Allelic Ratio Analysis in Maternal Plasma: Theoretical and Empirical Considerations, Clinical Chemistry, vol. 52, No. 12, Oct. 13, 2006, pp. 2194-2202.
Tong et al., Plasma Epigenetic Markers for Cancer Detection and Prenatal Diagnosis, Frontiers in Bioscience, vol. 11, Sep. 1, 2006, pp. 2647-2656.
Tong ET AI. et al., Noninvasive Prenatal Detection of Trisomy 21 by an Epigenetic-Genetic Chromosome-Dosage Approach, Clinical Chemistry, Molecular Diagnostics and Genetics, vol. 56, No. 1, Jan. 1, 2010, pp. 90-98.
Tsui et al., Noninvasive Prenatal Diagnosis of Hemophilia by Microfluidics Digital PCR Analysis of Maternal Plasma DNA, Blood, vol. 117, No. 13, Mar. 31, 2011, pp. 3684-3691.
Tufan et al., Analysis of Cell-Free Fetal DNA from Maternal Plasma and Serum Using a Conventional Multiplex PCR: Factors Influencing Success, Turkish Journal of Medical Science, vol. 35, 2005, pp. 85-92.
Tuzun et al., Fine-Scale Structural Variation of the Human Genome, Nat. Genet., vol. 37, No. 7, Jul. 2005, pp. 727-732.
Uitto et al., Probing the Fetal Genome: Progress in Non-Invasive Prenatal Diagnosis, Trends in Molecular Medicine, vol. 9, No. 8, Aug. 2003, pp. 339-343.
Voelkerding et al., Digital Fetal Aneuploidy Diagnosis by Next-Generation Sequencing, Clinical Chemistry, vol. 56, No. 3, Mar. 2010, pp. 336-338.
Vogelstein et al., Digital PCR, Proceedings of the National Academy of Sciences, vol. 96, No. 16, Aug. 1999, pp. 9236-9241.
Volik et al., End-Sequence Profiling: Sequence-Based Analysis of Aberrant Genomes, Proc. Natl. Acd. Sci., USA, vol. 100, No. 13, Jun. 24, 2003, pp. 7696-7701.
Warren et al., Transcription Factor Profiling in Individual Hematopoietic Progenitors by Digital RT-PCR, PNAS, vol. 103, No. 47, Nov. 21, 2006, pp. 17807-17812.
Wheeler et al., The Complete Genome of an Individual by Massively Parallel DNA Sequencing, Nature, vol. 452, Apr. 17, 2008, pp. 872-877.
White et al., Digital PCR Provides Sensitive and Absolute Calibration for High Throughput Sequencing, BMC Genomics, vol. 10, No. 116, Mar. 19, 2009, pp. 116-146.
Xiong et al., A Simple, Rapid, High-Fidelity and Cost-Effective PCR-Based Two-Step DNA Synthesis Method for Long Gene Sequences, Nucleic Acids Research, vol. 32, No. 12, e98, Feb. 2004, 10 pages.
Yang et al., Rapid Prenatal Diagnosis of Trisomy 21 by Real-time Quantitative Polymerase Chain Reaction with Amplification of Small Tandem Repeats and S100B in Chromosome 21, Yonsei Medical Journal, vol. 46, No. 2, Apr. 2005, pp. 193-197.
Zavala et al., Genomic GC Content Prediction in Prokaryotes from a Sample of Genes, Gene, vol. 357, No. 2, Sep. 2005, pp. 137-143.
Zheng et al., Nonhematopoietically Derived DNA is Shorter than Hematopoietically Derived DNA in Plasma: A Transplantation Model, Clinical Chemistry, vol. 58, No. 3, Mar. 2012, pp. 549-558.
Zhong et al., Fetal DNA in Maternal Plasma is Elevated in Pregnancies with Aneuploid Fetuses, Prenatal Diagnosis, vol. 20, No. 10, Oct. 2000, pp. 795-798.
Zhou et al., Counting Alleles Reveals a Connection Between Chromosome 18q Loss and Vascular Invasion, Nature Biology, vol. 19, No. 1, Jan. 2001, pp. 78-81.
Zhou et al., Counting Alleles to Predict Recurrence of Early-Stage Colorectal Cancers, The Lancet, vol. 359, No. 9302, Jan. 19, 2002, pp. 219-225.
Zhu et al., Single Molecule Profiling of Alternative Pre-mRNA Splicing, Science, vol. 301, Sep. 2003, pp. 836-838.
Zimmermann et al., Molecular Diagnosis in Prenatal Medicine, Ph.D. Thesis, Only Chapter 1, 2004, pp. 1-19.
Zimmermann et al., Novel Real-Time Quantitative PCR Test for Trisomy 21, Clinical Chemistry, vol. 48, No. 2, Feb. 2002, pp. 362-363.
Diehl, Frank et al.; "Digital quantification of mutant DNA in cancer patients"; Current Opinion in Oncology; Jan. 2007; vol. 19, No. 1; pp. 36-42.
Emanuel, Stuart L. et al.; "Amplification of Specific Gene Products from Human Serum"; GATA; Genetic Analysis: Biomolecular Engineering; 1993; vol. 10, Issue 6; pp. 144-146.
Hahn, Sinuhe et al.; "Prenatal Diagnosis Using Fetal Cells and Cell-Free Fetal DNA in Maternal Blood: What Is Currently Feasible?"; Clinical Obstetrics and Gynecology; Sep. 2002; vol. 45, No. 3; pp. 649-656.
Lo, Y-M. D. et al.; "Detection of fetal RhD sequence from peripheral blood of sensitized RhD-negative pregnant women"; British Journal of Haematology; Jul. 1994; vol. 87, Issue 3; pp. 658-660.
Lo, Y-M. D. et al.; "Detection of single-copy fetal DNA sequence from maternal blood"; The Lancet; Letters to the Editor; Jun. 16, 1990; vol. 335, Issue 8703; pp. 1463-1464.
Lo, Y-M. D. et al.; "Prenatal Sex Determination by DNA Amplification From Maternal Peripheral Blood"; The Lancet; Dec. 9, 1989; vol. 335, Issue 8676; pp. 11363-11365.
Martin, Maureen et al.; "A Method for Using Serum or Plasma as a Source of DNA for HLA Typing"; Human Immunology; Feb. 1992; vol. 33, Issue 2; pp. 108-113.
Nelson, M. et al.; "Genotyping fetal DNA by non-invasive means: extraction from maternal plasma"; Vox Sanguinis; 2001; vol. 80, Issue 2; pp. 112-116.
Pertl, Barbara et al.; "Fetal DNA in Maternal Plasma: Emerging Clinical Applications"; Obstetrics & Gynecology; Sep. 2001; vol. 98, No. 3; pp. 483-490.
Poon, Leo L.M. et al.; "Circulating fetal DNA in maternal plasma"; Clinica Chimica Acta; Nov. 2001; vol. 313, Issues 1-2; pp. 151-155.

(56) References Cited

OTHER PUBLICATIONS

Sparkes, Rebecca et al.; "New Molecular Techniques for the Prenatal Detection of Chromosomal Aneuploidy"; Journal of Obstetrics and Gynaecology Canada; Jul. 2008; vol. 30, Issue 7, No. 210; pp. 617-621.

Tettelin, H. et al.; "The nucleotide sequence of *Saccharomyces cerevisiae* chromosome VII"; Nature; Letters to Nature; Supplement to Nature May 29, 1997; vol. 387, Issue No. 6632S; pp. 81-84 (5 total pages).

Communication pursuant to Article 94(3) EPC dated Apr. 29, 2019 in EP Patent Application No. 16737075.8. 9 pages.

\* cited by examiner

From outer to inner ring:
1) CNAs in plasma (CAZA)
2) CNAs in plasma (1-Mb)
3) CNAs in tumor tissue (CAZA)
4) CNAs in tumor tissue (1-Mb)

| | No. of patients (percentage) with CNA detected in plasma for | | | | |
|---|---|---|---|---|---|
| | Chr 1p | Chr 1q | Chr 8p | Chr 8q | Any of chr 1p/1q/8p/8q |
| HCC patients (n=90) | 39/90 (43.3%) | 46/90 (51.1%) | 33/90 (36.7%) | 63/90 (70.0%) | 76/90 (84.4%) |
| Cirrhotic patients (n=36) | 3/36 (8.3%) | 5/36 (13.9%) | 1/36 (2.8%) | 1/36 (2.8%) | 8/36 (22.2%) |
| HBV carriers (n=67) | 1/67 (1.5%) | 3/67 (4.48%) | 1/67 (1.5%) | 1/67 (1.5%) | 3/67 (4.5%) |
| Healthy subjects (n=32) | 0/32 (0%) | 0/32 (0%) | 0/32 (0%) | 0/32 (0%) | 0/32 (0%) |

FIG. 4

| Case no. | Tumor DNA fraction in plasma (%) | Tumor size (cm) | 1p Tumor | 1p Plasma | 1q Tumor | 1q Plasma | 8p Tumor | 8p Plasma | 8q Tumor | 8q Plasma |
|---|---|---|---|---|---|---|---|---|---|---|
| HOT412 | 27.5 | 6.5 | Gain | Gain | Gain | Gain | Loss | Loss | Gain | Gain |
| HOT407 | 19.4 | 8 | Nil | Nil | Nil | Gain | Loss | Loss | Gain | Gain |
| HOT414 | 18.7 | 15 | Loss | Loss | Gain | Gain | Loss | Loss | Gain | Gain |
| HOT426 | 4.1 | 6.5 | Loss | Loss | Gain | Gain | Loss | Nil | Nil | Gain |
| HOT394 | 2.5 | 4 | Loss | Loss | Gain | Gain | Loss | Loss | Gain | Gain |
| HOT397 | 2.4 | 5.5 | Loss | Loss | Gain | Nil | Loss | Nil | Gain | Gain |
| HOT393 | 1.8 | 3 | Loss | Nil | Nil | Loss | Nil | Gain | Nil | Gain |
| HOT427 | 1.7 | 1.5 | Nil | Loss | Gain | Gain | Nil | Nil | Nil | Nil |
| HOT413 | 1.7 | 2 | Loss | Loss | Gain | Nil | Loss | Nil | Gain | Gain |
| HOT425 | 1.5 | 8.5 | Loss | Loss | Nil | Nil | Loss | Nil | Gain | Gain |
| HOT428 | 1.5 | 2 | Loss | Nil | Gain | Loss | Loss | Nil | Gain | Gain |
| HOT432 | 1.0 | 2 | Loss | Nil | Nil | Nil | Nil | Nil | Nil | Gain |

500

Concordant results in tumor and plasma 30/48 (63%)

CNA detected in tumor but not in plasma 10/48 (21%); Mainly for plasma samples with <2% tumor DNA CNA detected in plasma but not in tumor 7/48 (15%)

Different CNA patterns in tumor and plasma 1/48 (2%)

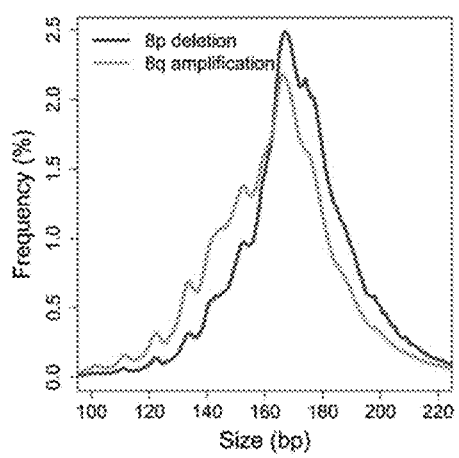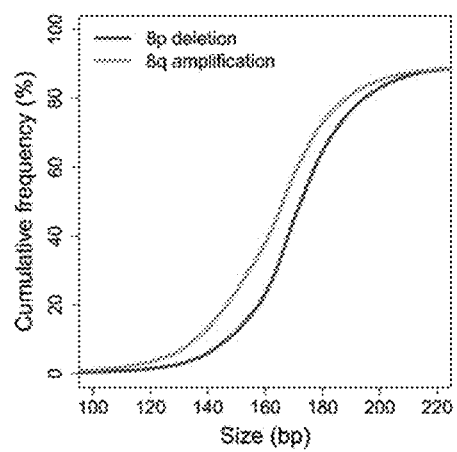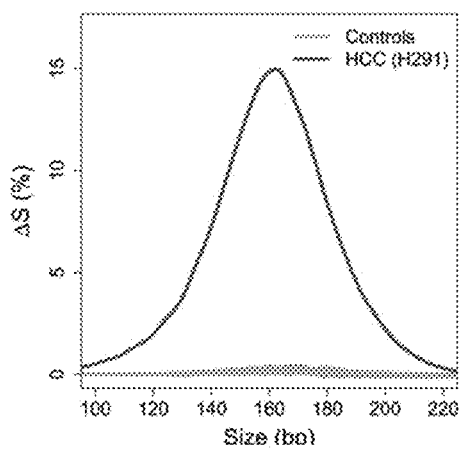
*FIG. 12*

USING SIZE AND NUMBER ABERRATIONS IN PLASMA DNA FOR DETECTING CANCER

CROSS-REFERENCES TO RELATED APPLICATIONS

This application claims priority to and is a nonprovisional of U.S. Patent Application No. 62/102,867 entitled "Using Size And Number Aberrations In Plasma DNA For Detecting Cancer" by Lo et al. filed Jan. 13, 2015; and 62/111,534 entitled "Using Size and Number Aberrations in Plasma DNA for Detecting Cancer" by Lo et al., filed Feb. 3, 2015, the disclosures of which are incorporated by reference in its entirety for all purposes.

BACKGROUND

The analysis of circulating cell-free DNA has been increasingly used for the detection and monitoring of cancers (1-3). Different cancer-associated molecular characteristics, including copy number aberrations (4-7), methylation changes (8-11), single nucleotide mutations (4, 12-15), cancer-derived viral sequences (16, 17) and chromosomal rearrangements (18, 19) can be detected in the plasma of patients with various types of cancers. Despite the rapid expansion of clinical applications, many fundamental molecular characteristics of circulating DNA in cancer patients remain unclear, thereby limiting the most effective clinical use of such analyses.

In particular, previous studies on the size of circulating DNA in cancer patients gave inconsistent results. Studies have demonstrated that the overall integrity (a measurement of size) of circulating DNA would increase in cancer patients when compared with subjects without a malignant condition (20-23). Using PCR with different amplicon sizes, it was shown that the proportion of longer DNA would be higher in cancer patients. This aberration in DNA integrity was shown to be reversible after treatment and the persistence of such changes was associated with poor prognosis (20, 24). On the other hand, there is also seemingly contradictory evidence that circulating DNA derived from tumor tissues might be shorter than those derived from non-malignant cells. For example, it has been shown that the proportion of DNA molecules carrying cancer-associated mutations would be higher when those mutations were detected using PCR with shorter amplicons (12, 25).

Further, studying the size profile of tumor-derived DNA in the plasma of the HCC patients is a challenging endeavor because tumor-derived plasma DNA cannot be readily distinguished from the non-tumor-derived background DNA in plasma. The detection of cancer-specific mutations offers a genotypic means to distinguish the tumoral from the non-tumoral plasma DNA. However, there are relatively few cancer-specific mutations across the genome (29-32). Accordingly, it can be difficult to accurately identify tumor-derived DNA in plasma, particularly for the purpose of generating a broad, detailed and yet cost-effective view of the size distribution of tumor-derived DNA.

Such difficulties provide obstacles in obtaining accurate measurements in samples possibly containing mixtures of tumoral and non-tumoral DNA.

BRIEF SUMMARY

Embodiments can provide systems and methods for determining whether regions exhibit an aberration (e.g., an amplification or a deletion), which may be associated with cancer. For example, embodiments can identify a region as possibly having an aberration using a count-based analysis and confirm whether the region does have the aberration using a size-based analysis.

In other embodiments, regions that exhibit an aberration can be compared to reference patterns that correspond to known types of cancer. A type of cancer can be identified when a sufficient number of regions have a matching aberration. Such matching regions can further be identified as related to the cancer for the analysis of tumor DNA, e.g., for a size analysis.

In yet other embodiments, a size analysis of DNA fragments in a sample (e.g., a mixture possibly containing both tumor and non-tumor DNA) can depend on a measured fraction of tumor DNA in the sample. For example, longer DNA fragments than healthy controls can indicate an early stage cancer for low tumor DNA fraction, and shorter DNA fragments than healthy controls can indicate a later stage cancer for higher tumor DNA fraction.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 4 is a table 400 showing detectability of CNA in plasma of HCC patients, hepatitis B virus (HBV) carriers, patients with liver cirrhosis and healthy subjects according to embodiments of the present invention.

FIG. 5 shows a table 500 of CNAs detected in the tumor and corresponding plasma of 12 HCC patients.

FIGS. 8A, 8B, and 8C show a table 800 of patterns of chromosomal regions for different types of cancer.

FIG. 12 shows size distributions of plasma DNA originating from the amplified 8q and deleted 8p of a representative case H291. (A) The size distributions of plasma DNA for 8p (red) and 8q (green). (B) Plot of cumulative frequencies for plasma DNA size for 8p (red) and 8q (green). (C) The difference in cumulative frequencies for the HCC case H291.

TERMS

Figure 1:
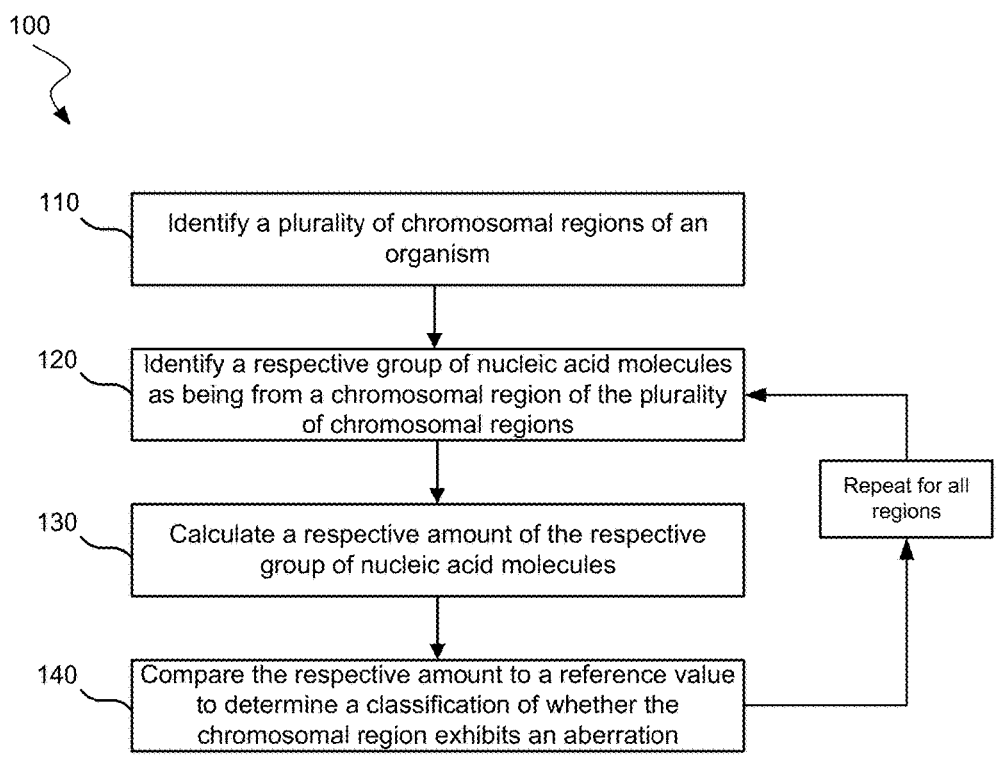
FIG. 1 is a flowchart illustrating a method 100 of identifying chromosomal regions as exhibiting an aberration according to embodiments of the present invention.

The term "biological sample" as used herein refers to any sample that is taken from a subject (e.g., a human, such as a pregnant woman) and contains one or more nucleic acid molecule(s) of interest. Examples include plasma, saliva, pleural fluid, sweat, ascitic fluid, bile, urine, serum, pancreatic juice, stool, cervical lavage fluid, and cervical smear samples.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer M A et al., *Nucleic Acids Res* 1991; 19:5081; Ohtsuka E et al., *J Biol Chem* 1985; 260:2605-2608; and Rossolini G M et al., *Mol Cell Probes* 1994; 8:91-98). The term nucleic acid is used interchangeably with gene, cDNA, mRNA, small noncoding RNA, microRNA (miRNA), Piwi-interacting RNA, and short hairpin RNA (shRNA) encoded by a gene or locus.

The term "gene" means the segment of DNA involved in producing a polypeptide chain. It may include regions preceding and following the coding region (leader and trailer) as well as intervening sequences (introns) between individual coding segments (exons).

As used herein, the term "locus" or its plural form "loci" is a location or address of any length of nucleotides (or base pairs) which has a variation across genomes.

The term "sequenced tag" (also called sequence read) refers to a sequence obtained from all or part of a nucleic acid molecule, e.g., a DNA fragment. In one embodiment, just one end of the fragment is sequenced, e.g., about 30 bp. The sequenced tag can then be aligned to a reference genome. Alternatively, both ends of the fragment can be sequenced to generate two sequenced tags, which can provide greater accuracy in the alignment and also provide a length of the fragment. In yet another embodiment, a linear DNA fragment can be circularized, e.g., by ligation, and the part spanning the ligation site can be sequenced.

The term fractional tumor DNA concentration is used interchangeably with the terms tumor DNA proportion and tumor DNA fraction, and refers to the proportion of DNA molecules that are present in a sample that is derived from a tumor.

The term "size profile" generally relates to the sizes of DNA fragments in a biological sample. A size profile may be a histogram that provides a distribution of an amount of DNA fragments at a variety of sizes. Various statistical parameters (also referred to as size parameters or just parameter) can be used to distinguish one size profile to another. One parameter is the percentage of DNA fragment of a particular size or range of sizes relative to all DNA fragments or relative to DNA fragments of another size or range.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "classification" as used herein refers to any number(s) or other characters(s) (including words) that are associated with a particular property of a sample. For example, a "+" symbol could signify that a sample is classified as having deletions or amplifications (e.g., duplications). The terms "cutoff" and "threshold" refer to a predetermined number used in an operation. For example, a cutoff size can refer to a size above which fragments are excluded. A threshold value may be a value above or below which a particular classification applies. Either of these terms can be used in either of these contexts.

The term "level of cancer" can refer to whether cancer exists, a stage of a cancer, a size of tumor, how many deletions or amplifications of a chromosomal region are involved (e.g. duplicated or tripled), and/or other measure of a severity of a cancer. The level of cancer could be a number or other characters. The level could be zero. The level of cancer also includes premalignant or precancerous conditions associated with deletions or amplifications.

A "subchromosomal region" is a region that is smaller than a chromosome. Examples of subchromosomal regions are 100 kb, 200 kb, 500 kb, 1 Mb, 2 Mb, 5 Mb, or 10 Mb. Another example of a subchromosomal region is one that corresponds to one or more bands, or subbands, or one of the arms of a chromosome. Bands or subbands are features observed in cytogenetic analysis. A subchromosomal region may be referred to by its genomic coordinates in relation to a reference human genome sequence.

DETAILED DESCRIPTION

Cancers often have regions with copy number aberrations (amplifications or deletions) relative to the person's normal genome. Techniques can count cell-free DNA fragments in a sample (e.g., plasma or serum) that include tumor DNA fragment and non-tumor DNA fragments. The counting can identify regions that are over-represented (indicative of amplification) or under-represented (indicative of deletion). But, as such count-based techniques are statistical in nature, incorrect indications can occur. Embodiments can identify a region as possibly having a copy number aberration (also referred to as aberration) using a count-based analysis and confirm whether the region does have the aberration using a size-based analysis. Such a confirmation provides additional accuracy in identifying regions with aberrations.

Regions that have aberrations can be used to identify an existence of cancer in the organism from which the sample was obtained. But, the existence of cancer does not convey a type of cancer. To address this problem, embodiments can use reference patterns of aberrations in regions from samples with known cancers. A test pattern of which regions are aberrant can be determined for a given sample being tested, and the test pattern can be compared to the references patterns to determine a type of cancer. An amount of regions of the test pattern that exhibit a same deletion or amplification as a reference pattern corresponding to a particular type of cancer can be determined, and the amount can be compared to a threshold to determine a classification of whether the particular type of cancer is present. Once a region is identified as both having an aberration and corresponding to a particular type of cancer, one can have greater confidence in analyzing the region for tumor DNA. For example, the region can be used to measure a tumor DNA fraction in the sample.

Additionally, various studies have shown inconsistent results as to the length of cell-free tumor DNA fragments: some showing longer fragments for tumor DNA and other showing shorter fragments for tumor DNA. The analysis below shows that both can be correct, but for different tumor DNA fractions. Embodiments can use different size thresholds in a size-analysis based on a measured tumor DNA fraction, which may be determined using counting of DNA fragments in a region identified as having an aberration. Accordingly, some implementations can reconcile these apparent inconsistencies through, for example: (a) genome-wide high resolution size profiling of plasma DNA enabled by massively parallel sequencing; and (b) an efficient approach to distinguish tumor-derived DNA from the non-tumoral background DNA in the plasma of cancer patients (e.g., using regions identified as having an aberration).

I. INTRODUCTION

It has become feasible to measure the lengths of millions or billions of every individual plasma DNA molecule in samples with the use of massively parallel sequencing (26, 27). Hence, plasma DNA sizes could be studied in a genom-ewide manner and at single-base resolution. Using this approach, the size of circulating DNA has generally been shown to resemble the size of mononucleosomal DNA suggesting that plasma DNA might be generated through apoptosis (26, 27). In pregnant women, plasma DNA derived from the fetus has been shown to be shorter than that of DNA derived from the mother (26). The size difference between circulating fetal and maternal DNA has provided a new conceptual basis for quantifying fetal DNA in maternal plasma and detecting chromosomal aneuploidies through size analysis of plasma DNA (28). In addition, differences in the size distributions of circulating DNA derived from the transplanted organs and the patients' own tissues have been observed for recipients of solid organ or bone marrow transplantation (27).

Plasma of cancer patients contains a mixture of tumor-derived DNA and non-tumor-derived DNA. Examples below analyze the size distribution of plasma DNA in cancer patients with hepatocellular carcinoma (HCC). The size distributions of plasma DNA in HCC patients, patients with chronic hepatitis B virus (HBV) infection, patients with liver cirrhosis and healthy subjects were also analyzed. Embodiments can use certain aberrant regions to analyze the size profile of tumor-derived DNA in the plasma of the HCC patients. The use of such aberrant regions can overcome the challenge that tumor-derived plasma DNA is not readily distinguished from the non-tumor-derived background DNA in plasma.

Some embodiments use chromosome arms that are affected by copy number aberrations (CNAs) to infer the difference in size distributions of tumor- and non-tumor-derived plasma DNA. For chromosome arms that are amplified in the tumor tissues, the proportional contribution from tumor-derived DNA to plasma DNA would increase whereas for chromosome arms that are deleted in the tumor, the contribution would decrease. Therefore, the comparison of size profiles of chromosome arms that are amplified and deleted would reflect the size difference between tumor-derived and non-tumor-derived DNA in plasma. CNAs involving a whole chromosome arm or a large trunk of a chromosome arm is relatively common (33). Deletion of chromosomes 1p and 8p and amplification of chromosomes 1q and 8q are commonly observed in the HCC tissues (34-36). Thus, the analysis focuses on chromosomes 1 and 8 for the CNA and size profiling analyses of plasma DNA.

II. COUNTING ANALYSIS TO IDENTIFY ABERRANT REGIONS

An aberrant region includes an amplification or a deletion. An amplification means that a sequence in the region occurs more often than it does in a reference sequence, and thus the sequence has been amplified. The amplification typically would occur in only one chromosome copy (haplotype). A deletion means that a sequence in the region has been deleted relative to the reference sequence, typically just one chromosome copy has the deletion for diploid organisms. A region can be defined by at least two loci (which are separated from each other), and DNA fragments at these loci can be used to obtain a collective value about the region.

A. Detecting an Aberrant Region by Counting

The aberration of a region can be determined by counting an amount of DNA fragments (molecules) that are derived from the region. As examples, the amount can be a number of DNA fragments, a number of bases to which a DNA fragment overlapped, or other measure of DNA fragments in a region. The amount of DNA fragments for the region can be determined by sequencing the DNA fragments to obtain sequence reads and aligning the sequence reads to a reference genome. In one embodiment, the amount of sequence reads for the region can be compared to the amount of sequence reads for another region so as to determine over-representation (amplification) or underrepresentation (deletion). In another embodiment, the amount of sequence reads can be determined for one haplotype and compared to the amount of sequence reads for another haplotype.

Accordingly, the number of DNA fragments from one chromosomal region (e.g., as determined by counting the sequenced tags aligned to that region) can be compared to a reference value (which may be determined from a reference chromosome region, from the region on another haplotype, or from the same region in another sample that is known to be healthy). The comparison can determined whether the amount is statistically different (e.g., above or below) the reference value. A threshold for the difference can be used, e.g., corresponding to 3 standard deviations (SD), as seen in a distribution of values seen in a population.

As part of the comparison, a tag count can be normalized before the comparison. A normalized value for the sequence reads (tags) for a particular region can be calculated by dividing the number of sequenced reads aligning to that region by the total number of sequenced reads alignable to the whole genome. This normalized tag count allows results from one sample to be compared to the results of another sample. For example, the normalized value can be the proportion (e.g., percentage or fraction) of sequence reads expected to be from the particular region. But, many other normalizations are possible, as would be apparent to one skilled in the art. For example, one can normalize by dividing the number of counts for one region by the number of counts for a reference region (in the case above, the reference region is just the whole genome) or by always using a same number of sequence reads. This normalized tag count can then be compared against a threshold value, which may be determined from one or more reference samples not exhibiting cancer.

In some embodiments, the threshold value can be the reference value. In other embodiments, the reference value can be the other value used for normalization, and the comparison can include the reference value and the threshold value. For example, the amount for the region can be divided by the reference value to obtain a parameter, which is compared to the threshold value to see if a statistically significant different exists. As another example, the amount for the region can be compared to the reference value plus the threshold value.

In one embodiment, the comparison is made by calculating the z-score of the case for the particular chromosomal region. The z-score can be calculated using the following equation: z-score=(normalized tag count of the case−mean)/SD, where "mean" is the mean normalized tag count aligning to the particular chromosomal region for the reference samples; and SD is the standard deviation of the number of normalized tag count aligning to the particular region for the reference samples. Hence, the z-score can correspond to the number of standard deviations that the normalized tag count of a chromosomal region for the tested case is away from the mean normalized tag count for the same chromosomal region of the one or more reference subjects. This z-score can be compared to a threshold, e.g., 3 for amplification and −3 for deletion. Chromosomal regions that are amplified would have a positive value of the z-score above the threshold. Chromosomal regions that are deleted would have a negative value of the z-score that is below the threshold.

The magnitude of the z-score can be determined by several factors. One factor is the fractional concentration of tumor-derived DNA in the biological sample (e.g. plasma). The higher the fractional concentration of tumor-derived DNA in the sample (e.g. plasma), the larger the difference between the normalized tag count of the tested case and the reference cases would be. Hence, a larger magnitude of the z-score would result.

Another factor is the variation of the normalized tag count in the one or more reference cases. With the same degree of the over-representation of the chromosomal region in the biological sample (e.g. plasma) of the tested case, a smaller variation (i.e. a smaller standard deviation) of the normalized tag count in the reference group would result in a higher z-score. Similarly, with the same degree of under-representation of the chromosomal region in the biological sample (e.g. plasma) of the tested case, a smaller standard deviation of the normalized tag count in the reference group would result in a more negative z-score.

Another factor is the magnitude of chromosomal aberration in the tumor tissues. The magnitude of chromosomal aberration refers to the copy number changes for the particular chromosomal region (either gain or loss). The higher the copy number changes in the tumor tissues, the higher the degree of over- or under-representation of the particular chromosomal region in the plasma DNA would be. For example, the loss of both copies of the chromosome would result in greater under-representation of the chromosomal region in the plasma DNA than the loss of one of the two copies of the chromosome and, hence, resulted in a more negative z-score. Typically, there are multiple chromosomal aberrations in cancers. The chromosomal aberrations in each cancer can further vary by its nature (i.e. amplification or deletion), its degree (single or multiple copy gain or loss) and its extent (size of the aberration in terms of chromosomal length).

The precision of measuring the normalized tag count is affected by the number of molecules analyzed. For example, 15,000, 60,000 and 240,000 molecules may be needed to be analyzed to detect chromosomal aberrations with one copy change (either gain or loss) when the fractional concentration is approximately 12.5%, 6.3% and 3.2% respectively. Further details of the tag counting for detection of cancer for different chromosomal regions is described in U.S. Patent Publication No. 2009/0029377 entitled "Diagnosing Fetal Chromosomal Aneuploidy Using Massively Parallel Genomic Sequencing" by Lo et al; and U.S. Pat. No. 8,741,811 entitled "Detection Of Genetic Or Molecular Aberrations Associated With Cancer" by Lo et al., the disclosure of which are incorporated by reference in its entirety for all purposes.

B. Method

FIG. 1 is a flowchart illustrating a method 100 of identifying a chromosomal region as potentially exhibiting an amplification according to embodiments of the present invention. Method 100, and other methods described herein, can be performed entirely or partially using a computer system.

At step 110, a plurality of chromosomal regions of an organism may be identified. Each chromosomal region may include a plurality of loci. A region may be 1 Mb in size, or some other equal size. The entire genome can then include about 3,000 regions, each of predetermined size and location. Such predetermined regions can vary to accommodate a length of a particular chromosome or a specified number of regions to be used, and any other criteria mentioned herein. If regions have different lengths, such lengths can be used to normalize results, e.g., as described herein.

Steps 120-140 may be performed for each of the chromosomal regions. At step 120, for each chromosomal region, a respective group of nucleic acid molecules may be identified as being from the chromosomal region. The identification may be based on identifying a location of nucleic acid molecules in a reference genome. For example, the cell-free DNA fragments can be sequenced to obtain sequence reads, and the sequence reads can be mapped (aligned) to the reference genome. If the organism was a human, then the reference genome would be a reference human genome, potentially from a particular subpopulation. As another example, the cell-free DNA fragments can be analyzed with different probes (e.g., following PCR or other amplification), where each probe corresponds to a different genomic location. In some embodiments, the analysis of the cell-free DNA fragments can be performed by receiving sequence reads or other experimental data corresponding to the cell-free DNA fragments, and then analyzing the experimental data using a computer system.

At step 130, a computer system may calculate a respective amount of the respective group of nucleic acid molecules. The respective value defines a property of the nucleic acid molecules of the respective group. The respective value can be any of the values mentioned herein. For example, the value can be the number of fragments in the group or a statistical value of a size distribution of the fragments in the group. The respective value can also be a normalized value, e.g., a tag count of the region divided by the total number of tag counts for the sample or the number of tag counts for a reference region. The respective value can also be a difference or ratio from another value, thereby providing the property of a difference for the region.

At step 140, the respective amount may be compared to a reference value to determine a classification of whether the chromosomal region exhibits an aberration (i.e. an amplification or a deletion). In some embodiments, the chromosomal region may be classified as not exhibiting an aberration. The comparison may include determining a z-score based on the respective amount and the reference value. As an example, the reference value may be any threshold or reference value described herein. For example, the reference value could be a threshold value determined for normal samples. As another example, the reference value could be the tag count for another region, and the comparison can include taking a difference or ratio (or function of such) and then determining if the difference or ratio is greater than a threshold value.

The reference value may vary based on the results of other regions. For example, if neighboring regions also show a deviation (although small compared to a threshold, e.g., a z-score of 3), then a lower threshold can be used. For example, if three consecutive regions are all above a first threshold, then cancer may be more likely. Thus, this first threshold may be lower than another threshold that is required to identify cancer from non-consecutive regions. Having three regions (or more than three) having even a small deviation can have a low enough probability of a chance effect that the sensitivity and specificity can be preserved.

C. Chromosome Arm-Level Z-Score Analysis (CAZA)

In some embodiments, a chromosome can be split into many subchromosomal regions (e.g., 1 Mb regions). This high resolution may not maximize sensitivity and specificity. Other embodiments can split a chromosome into two arms, namely p and q. Analyzing the two arms can improve specificity by reducing noise caused by such fine resolution. An example of chromosome arm-level z-score analysis is now provided.

We analyzed a total of 225 plasma DNA samples from 90 HCC patients, 67 patients with chronic HBV infection, 36 patients with HBV-associated liver cirrhosis and 32 healthy subjects. A median of 31 million reads (range: 17-79 million) was obtained from each plasma sample. Amounts of sequence reads originating from chromosome arms that were three SDs below (z-scores <−3) and three SDs above (z-scores >3) the mean of healthy controls were deemed to indicate significant under- and over-representations of the plasma DNA from those chromosome arms, respectively. These quantitative plasma DNA aberrations were generally reflective of the presence of copy number losses and copy number gains (CNAs) in the tumor (4).

Figure 2:
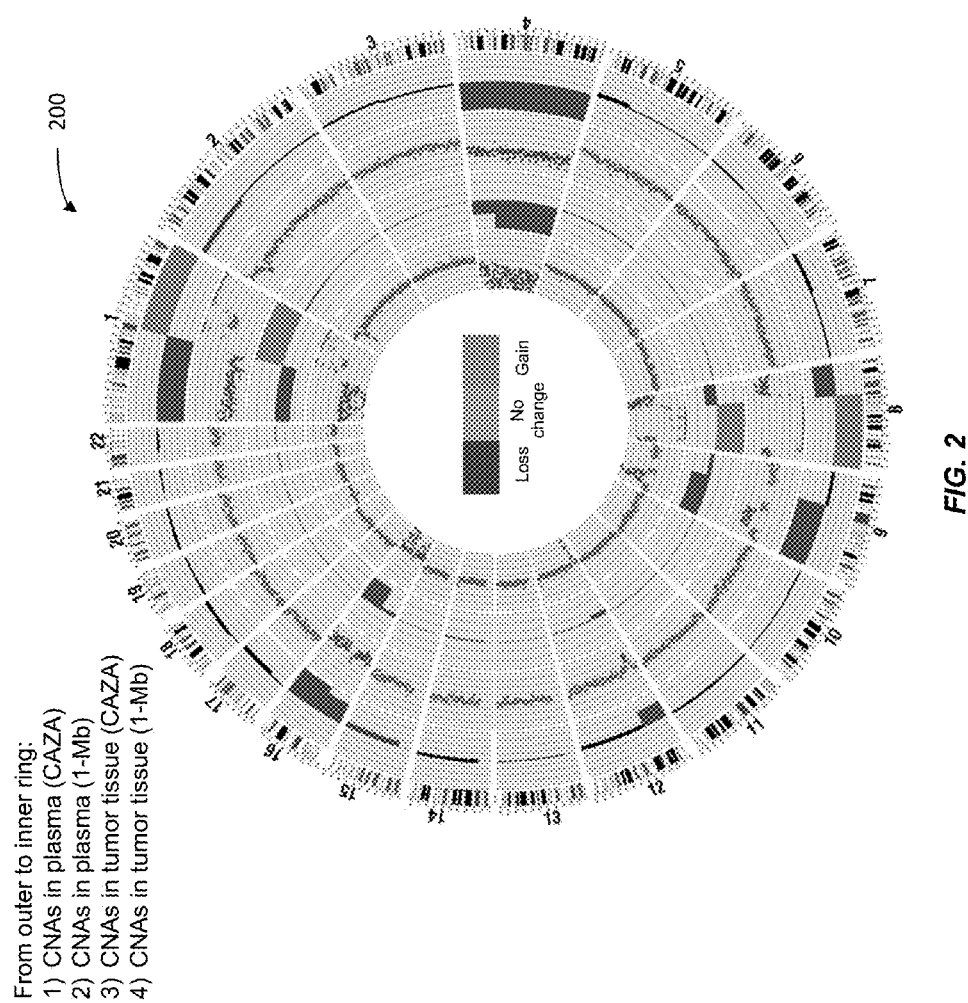
FIG. 2 shows a Circos plot 200 identifying regions exhibiting amplifications and deletions in plasma and tissue samples of a representative hepatocellular carcinoma (HCC) patient according to embodiments of the present invention.

FIG. 2 shows a Circos plot 200 identifying regions exhibiting amplifications and deletions in plasma and tissue samples of a representative hepatocellular carcinoma (HCC) patient according to embodiments of the present invention. From inside to outside: CNAs in the tumor tissue (in 1-Mb resolution); arm-level CNAs in the tumor tissue; plasma CNAs (in 1-Mb resolution); arm-level plasma CNAs. Regions with gains and losses are shown in green and red, respectively. The distance between two consecutive horizontal lines represents a z-score of 5. Chromosome ideograms (outside the plots) are oriented from pter to qter in a clockwise direction.

Figure 3:
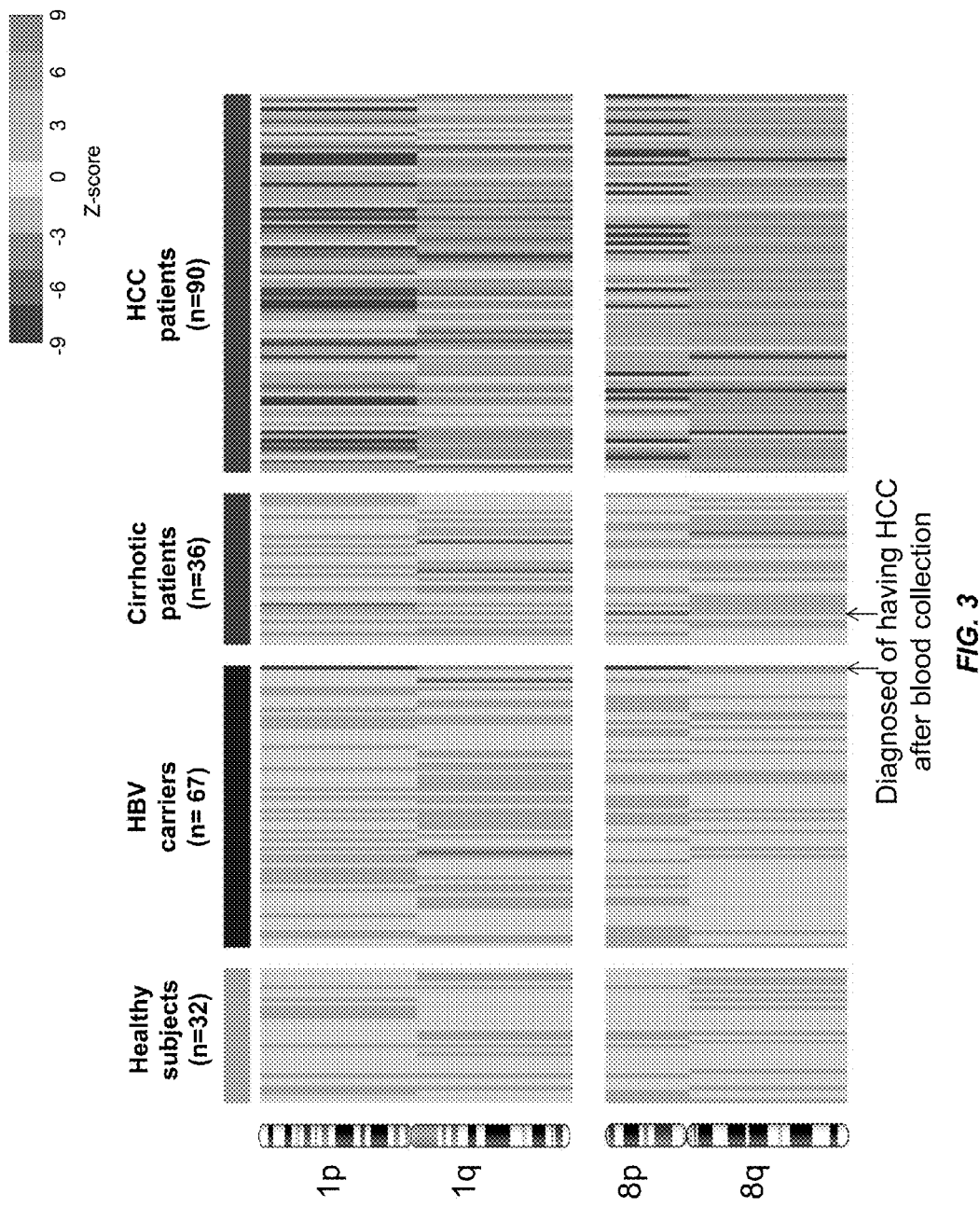
FIG. 3 shows plasma copy number aberration (CNA) results for various subjects according to embodiments of the present invention.

FIG. 3 shows plasma copy number aberration (CNA) results for all the studied subjects using an embodiment of CAZA. The four chromosome arms (1p, 1q, 8p and 8q) that are frequently affected by CNAs in HCC were analyzed. Red and green lines represent under- and over-representation, respectively, of the corresponding chromosome arms in plasma. Each vertical line represents the data for one case.

FIG. 4 is a table 400 showing detectability of CNA in plasma of HCC patients, HBV carriers, patients with liver cirrhosis and healthy subjects according to embodiments of the present invention. Table 400 shows categories of patients in the leftmost column. The remaining columns show the number of patients and the percentage with CNA detected in the plasma for different chromosome arms. Seventy-six (84.4%) of the 90 HCC patients had at least one chromosomal arm-level CNA on chromosomes 1 and 8 in plasma. Tumor tissues of 12 HCC patients were available to corroborate the plasma DNA findings. The tissue samples were sequenced and the CNA patterns are shown in FIG. 5.

FIG. 5 shows a table 500 of CNAs detected in the tumor and corresponding plasma of 12 HCC patients. In table 500, the patient case number is listed in the first column. The patients are arranged in descending order of tumor DNA fraction in plasma, as shown in the second column. The third column shows the tumor size. The remaining columns show CNAs detected in the tumor and plasma for different chromosome arms. 'Gain' indicates a copy number gain. 'Loss' indicates a copy number loss. 'Nil' indicates no detectable CNA. A total of 48 chromosome arms were analyzed for the 12 patients. The numbers (and percentages) of chromosome arms with concordant and discordant results between tumor and plasma are shown.

Of the 48 chromosome arms analyzed for the 12 patients, concordant changes in plasma and tumor tissues were observed for 30 (63%) arms. CNAs were only observed in the tumor, but not in the plasma, for 10 (21%) arms. These cases tended to have lower tumor DNA fractions in plasma. CNAs were observed in the plasma, but not the tumor, for 7 (15%) arms. In one case (HOT428), a gain of 1q was observed in the tumor, but a loss was observed in plasma. These data might suggest the presence of tumoral heterogeneity where there might be other foci or clones of cancer cells contributing plasma DNA.

Among the HBV carriers with and without liver cirrhosis, the detection rates of these CNA were 22.2% and 4.5%, respectively. One patient with liver cirrhosis and one chronic HBV carrier without cirrhosis exhibited CNAs in plasma, but not known to have HCC at the time of blood collection, were diagnosed as having HCC at 3 months and 4 months afterwards, respectively. All the HBV carriers and cirrhotic patients were followed up for at least 6 months. For those control subjects without any CNA in plasma, none of them had developed HCC during the follow-up period. None of the 32 healthy subjects had detectable CNA on chromosome 1 or 8 in plasma by CAZA. In the HCC patients, the disproportionate increase or decrease in sequence reads in plasma due to the presence of CNA is reflective of the fractional concentration of tumor DNA in the plasma sample. The median fractional concentration of tumor-derived DNA in the plasma of the HCC patients was 2.1% (range: 0% to 53.1%; interquartile range: 1.2% to 3.8%).

CAZA provides a way to detect tumor-associated CNAs non-invasively. In HCC, chromosomes 1 and 8 are commonly affected by CNAs (34-36). Indeed, our data showed that 76 (84.4%) of the 90 HCC patients had at least one CNA involving either arms on chromosomes 1 and 8 in plasma, whereas none of the 32 healthy subjects exhibited any CNA for these two chromosomes in plasma. Plasma CNAs involving chromosomes 1 and 8 were also detected in 22.2% and 4.5% of the cirrhotic patients and HBV carriers. In one HBV carrier and one patient with liver cirrhosis, HCC was diagnosed shortly after the blood collection. It is likely that the cancer would have been present at the time of blood collection and was associated with the CNAs in plasma, thereby showing the early screening capabilities of embodiments. The relatively high detection rate of plasma CNAs in the HCC patients suggests that this approach might have future value in the screening of HBV carriers. Moreover, CNAs are present in almost all types of cancer (33). Therefore, this approach can be applied as a generic tumor marker with adaptation to the specific CNA patterns of the cancer of interest.

III. DETECTING CANCER TYPE BASED ON PATTERN OF ABERRANT REGIONS

Some embodiments can use known aberrant regions (along with whether amplification or deletion) of a type of cancer in order to identify potential cancers implicated by aberrations identified in the sample. In the example above, the known aberrant regions for HCC were used to screen the sample for HCC. This screening can compare the identified aberrant regions (including whether amplification or deletion) to a known set of aberrant regions. If a sufficiently high match is determined, then that type of cancer can be flagged as a possible test result.

A matching criteria can be the percentage of regions of the set that are also identified in the sample. The matching criteria can require specific regions to be aberrant. For example, the match can be identified for HCC when 1p, 1q, or 8q is aberrant, or when more than one of these chromosome arms are aberrant. Thus, there can be specific subsets to which identical match is required, but the subsets can be smaller than a full set of known aberrant regions for a type of cancer.

Thus, a pattern of aberrant regions for a test sample can be compared to the pattern of aberrant regions for a particular type of cancer, which may be determined from patients known to have a particular type of cancer. Embodiments can be used to screen for cancer and identify the type of cancer involved, particularly where the tumor may be small (e.g., less than 2 cm in size). Imaging techniques have difficulty in identifying tumors less than 2 cm in size. Such techniques can also be used to track progress of the patient after treatment.

A. Method

Figure 6:
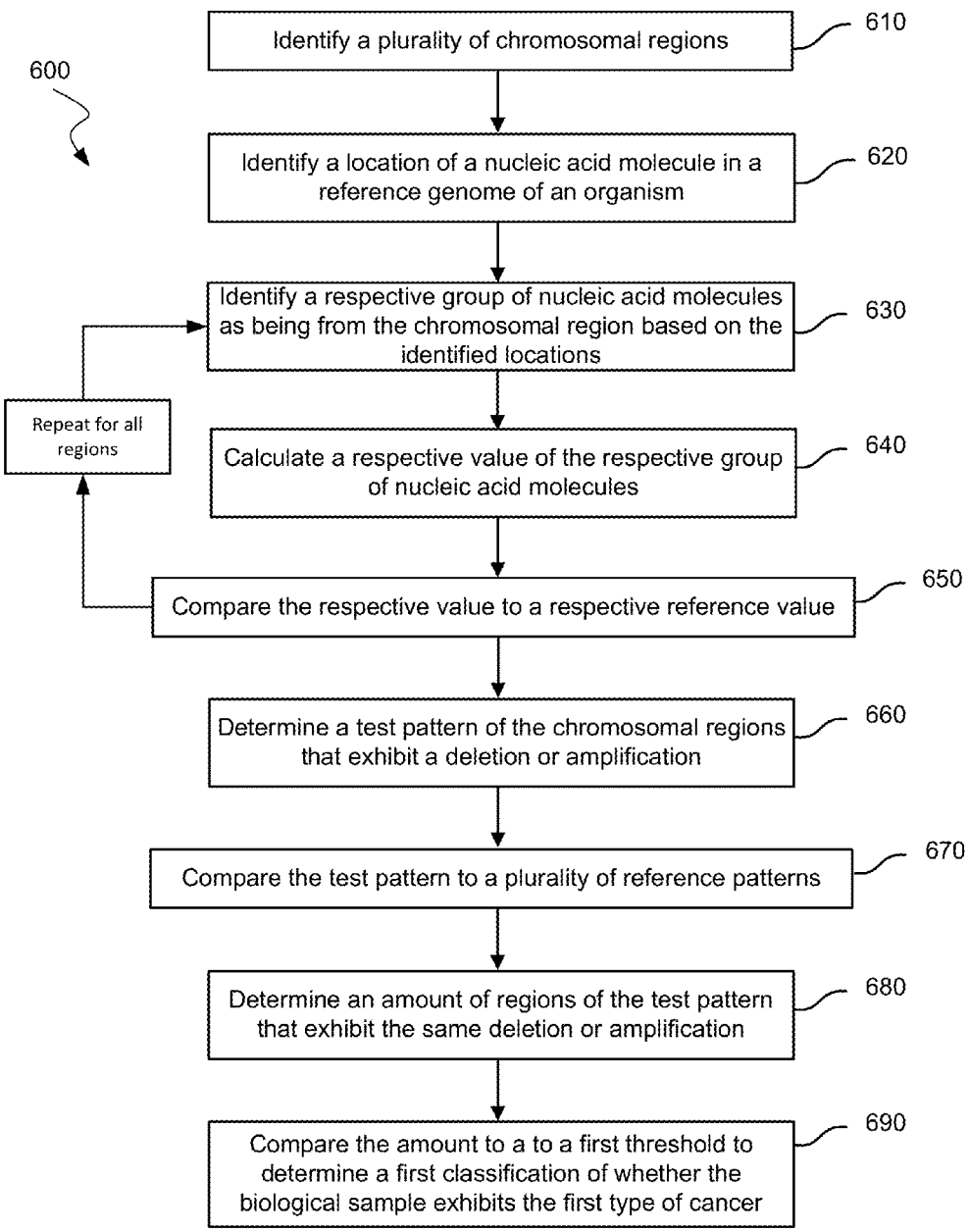
FIG. 6 shows a flowchart illustrating a method of analyzing a biological sample of an organism to determine whether a biological sample exhibits a first type of cancer according to embodiments of the present invention.

FIG. 6 is a flowchart illustrating a method 600 of analyzing a biological sample of an organism to determine whether a biological sample exhibits a first type of cancer according to embodiments of the present invention. The biological sample includes nucleic acid molecules (also called fragments) originating from normal cells and potentially from cells associated with cancer. At least some of these molecules may be cell-free in the sample.

In one embodiment of this and any other method described herein, the biological sample includes cell-free DNA fragments. Although the analysis of plasma DNA has been used to illustrate the different methods described in this application, these methods can also be applied to detect tumor-associated chromosomal aberrations in samples containing a mixture of normal and tumor-derived DNA. The other sample types include saliva, tears, pleural fluid, ascitic fluid, bile, urine, serum, pancreatic juice, stool and cervical smear samples In step 610, a plurality of chromosomal regions of the organism are identified. The plurality of chromosomal regions are subchromosomal and may be non-overlapping. The chromosomal regions that are counted can have restrictions. For example, only regions that are contiguous with at least one other region may be counted (or contiguous regions can be required to be of a certain size, e.g., four or more regions). For embodiments where the regions are not equal, the number can also account for the respective lengths (e.g., the number could be a total length of the aberrant regions). In some embodiments, the regions correspond to arms of the chromosomes. In other embodiments, the regions may be smaller than the arms, e.g., 1-Mb regions.

In some embodiments, a chromosomal region can be of a particular haplotype (i.e., correspond to a particular chromosome copy). In embodiments using a relative haplotype dosage (RHDO) analysis, each region can include at least two heterozygous loci. Further details on RHDO can be found in U.S. Pat. No. 8,741,811.

In step 620, for each of a plurality of nucleic acid molecules in the biological sample of the organism, a location of the nucleic acid molecule in a reference genome of the organism can be identified. The plurality of nucleic acid molecules may include 500,000 or more molecules (fragments). This locating can be performed in various ways, including performing a sequencing of a molecule (e.g. via a random sequencing), to obtain one or two (paired-end) sequenced tags of the molecule and then aligning the sequenced tag(s) to the reference genome. Such alignment can be performed using such as tools as basic local alignment search tool (BLAST). The location can be identified as a number in an arm of a chromosome.

In step 630, a respective group of nucleic acid molecules may be identified as being from the chromosomal region based on the identified region, for each of the plurality of chromosomal regions. The respective group may include at least one nucleic acid molecule located at each of the plurality of loci of the chromosomal region.

In step 640, a computer system may calculate a respective value of the respective group of nucleic acid molecules for each of the plurality of chromosomal regions. The respective value may define a property of the nucleic acid molecules of the respective group. The property may be a count, a percentage, or a size of the nucleic acid molecules. The respective value may include a mean of a size distribution, a median of the size distribution, a mode of the size distribution, or a proportion of nucleic acid molecules having a size below a size threshold. Using size as a property is discussed in greater detail in Section IV.

In step 650, the respective value may be compared to a respective reference value to determine a classification of whether the chromosomal region exhibits a deletion or an amplification. The comparison may include determining a z-score based on the respective value and the respective reference value. The z-score can then be compared to one or more threshold values to determine whether a deletion or an amplification exists. Different thresholds can be used for a deletion and an amplification. In other embodiments, the reference value can include the threshold value, e.g., if the other values in the z-score were moved to the other side of the equation. A reference value can correspond to a value determined in a healthy sample, another chromosomal region (e.g., one not exhibiting an aberration), or the other haplotype when the region being tested is a first haplotype.

In step 660, a test pattern of the chromosomal regions that exhibit a deletion or amplification may be determined. The test pattern refers to the pattern of aberrant regions in the sample being tested. The test pattern may include a set of chromosomal regions that exhibit a deletion, an amplification, or are normal. The test pattern may also include a first subset of the set that is identified as exhibiting an amplification. The test pattern may further include a second subset of the set that is identified as exhibiting a deletion. The test pattern can further include a third subset of the set that is identified as not exhibiting an amplification or a deletion.

In step 670, the test pattern may be compared to a plurality of reference patterns of different types of cancer. A reference patterns for a type of cancer may include a known set of aberrant regions. The reference patterns may be determined from reference samples of tissues and/or mixtures of cell-free nucleic acid molecules. The reference pattern may include a number of regions, with each having a defined status of amplification, deletion, or no aberration. The comparison can determine which regions of the test pattern have a same aberration as regions in a reference pattern. For example, it can be determined whether the same region is indicated as having an amplification, a deletion, or is normal in both the test pattern and a reference pattern.

In step 680, based on the comparison, an amount of regions of the test pattern that exhibit a same deletion or amplification as a first reference pattern corresponding to a first type of cancer can be determined. In various embodiments, the amount may be a number or percentage of chromosomal regions that match with the known set of aberrant regions.

In step 690, the amount of regions is compared to a first threshold to determine a first classification of whether the biological sample exhibits the first type of cancer. The first threshold may be specific to the first type of cancer or be used across multiple types of cancer. Such a threshold may be a minimum amount of chromosomal regions needed to match with the known set of aberrant regions for the first type of cancer to be identified. In various embodiments, the minimum amount may be 3, 4, 5, 6, 7, 8, 9, 10, 11, 12, or 13 chromosomal regions. In some embodiments, specific regions may be required to be aberrant, and thus other criteria can be used besides the comparison of the amount to the first threshold. Such specific regions can be a constraint or be weighted higher than other regions. The specific aberrant regions may be a subset of the full set of known aberrant regions for a type of cancer. The type of cancer may include HCC, colorectal cancer, breast cancer, lung cancer, or nasopharyngeal carcinoma, among other cancers.

A threshold value used to determine the classification may vary based on the locations and the sizes of the regions that are counted. For example, the amount of regions on a particular chromosome or arm of a chromosome may be compared to a threshold for that particular chromosome (or arm) as a criterion for determining whether a particular type of cancer is implicated. Multiple thresholds may be used. For instance, the amount of matching regions (i.e., same classification of aberration in test pattern and reference pattern) on a particular chromosome (or arm or larger subchromosomal region) may be required to be greater than a first threshold value, and the total amount of matching regions in the genome may be required to be greater than a second threshold value.

The threshold value for the amount of matching regions can also depend on how strong the imbalance is for the classification of the regions. For example, the amount of matching regions that are used as the threshold for determining a classification of a type of cancer can depend on the specificity and sensitivity (aberrant threshold) used to detect an aberration in each region. For example, if the aberrant threshold is low (e.g. z-score of 2), then the amount threshold may be selected to be high (e.g., 15 matching regions or 80%). But, if the aberrant threshold is high (e.g., a z-score of 3), then the amount threshold may be lower (e.g., 5 matching regions or 60%). The amount of regions showing an aberration can also be a weighted value, e.g., one region that shows a high imbalance can be weighted higher than a region that just shows a little imbalance (i.e. there are more classifications than just positive and negative for the aberration). Such a weighting can act in a similar manner as certain regions that are required to have an aberration for the type of cancer to be identified.

In some embodiments, the threshold can be determined dynamically based on the number of matching regions for other types of cancers. For example, the threshold can be that the number of matching regions for the identified cancer be at least a specific number greater than the matching regions for the next most likely cancer type. Such a threshold can be an additional criterion in addition to a minimum threshold. Thus, in some instances, no cancer type might be identified if a sufficient number of matching regions do not exist.

B. Results

Method 600 was tested for a plurality of cancer types to determine the accuracy. Method 600 was tested with patients of known cancer type. Further, the thresholds used can be determined using samples of known cancer types. Different thresholds can be used for different cancer types.

The plasma DNA of each of 17 cancer patients (6 patients with HCC, 4 with colorectal cancers (CRC), 3 with breast cancers (BrC), 2 with lung cancers (LC) and 2 with nasopharyngeal carcinoma (NPC)) was sequenced. Copy number aberrations (CNAs) for each chromosome arm were analyzed for each patient based on the CAZA approach.

Figure 7:
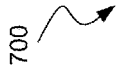
FIG. 7 shows chromosome arms that exhibit different patterns for different types of cancers in table 700 according to embodiments.

FIG. 7 shows chromosome arms that exhibit different patterns for different types of cancers in table 700 according to embodiments. CNAs that occur in ≥50% of the cases are highlighted in color. Copy number losses are highlighted in red, and copy number gains are highlighted in green.

Table 700 has the chromosome arm listed on the leftmost column. Each of the other columns lists the type of cancer and a patient number for the cancer type. A deletion is identified with '−'. An amplification is identified with '+'. A normal region is identified with 'Nil'.

The patterns of CNAs observed in the plasma samples are different for patients suffering from different types of cancers. Based on the most common patterns of CNAs observed in plasma, embodiments can deduce the potential tissue origin of cancers in patients with CNAs observed in plasma but the source of CNAs is unknown. The patterns of CNAs listed in table 700 are for illustration purposes, and a more comprehensive list of CNAs can be established by analyzing a much larger number of clinical samples.

The reference patterns of CNAs can also be determined from the analysis of tumor tissue. As examples, gains on 1q, 6p, 8q and 17q, and losses on 4q, 8p, 13q, 16q and 17p are commonly detected in HCC tumor tissues (Moinzadeh P et al. Br J Cancer 2005; 92:935-941). Gains on 5p, 8q, 9p, 13q and 20q, and losses on 8p, 9p, 17p and 18q are commonly detected in CRC tumor tissues (Farzana et al. PLoS One 2012; 2:231968 and Lips E H et al. J Pathol 2007; 212:269-77). Gains on 5p, 7p, 7q, 8q 14q, 17q and 20q, and losses on 3p, 8p, 9p, 13q and 18q are commonly detected in non-small cell lung cancer tissues whereas gains on 3q, 5p, 14q and 19q, and losses on 3p, 4p, 4q, 5q, 10p, 10q, 13q, 15q, 17p and 22q are commonly detected in small cell lung cancer tissues (Zhao X et al. Cancer Res 2005; 65:5561-70). Gains on 1q, 8q, 17q and 20q, and losses on 4p, 5q, 8p, 11q and 13q are common in breast cancer tissues (Andre F et al. Clin Cancer Res 2009; 15:441-51). The patterns of CNAs described here are serve as illustrative examples and are not intended to be the only patterns that can be used in methods described herein.

Based on the CNA patterns in this example, assume that plasma DNA sequencing was performed for the patient BrC2 for the purpose of cancer screening. CNAs, including copy number gains for 1q, 3q, 8q, and 14q and copy number losses for 2p, 2q, 3p, 4p, 7q, 8p, 9p, 11p, 12p, 12q, 16q, and 17p, were observed. The CNAs in her plasma matched 13 typical CNAs for breast cancers. In contrast, her CNAs only matched 3, 6, 4, and 1 typical CNAs of HCC, CRC, LC, and NPC, respectively. Therefore, based on the CNA pattern of her plasma DNA, the most likely cancer that she has is deduced to be breast cancer. The selected threshold can be used to determine if the number of CNAs observed is compatible with the typical CNAs of certain cancer types. In this example, a threshold of 7, 8, 9, 10, 11, 12, or 13 can be used to classify the CNAs as compatible with breast cancer. A percentage of matching regions can also be used. For example, a percentage of regions that match the commonly aberrant regions can be used. The commonly aberrant regions can be defined as regions that have a particular aberration in more than 50% of the reference samples.

In other embodiments, other statistical approaches, for example, but not limited to hierarchical clustering, can be used to deduce the most likely cancer type a patient is having. For example, each reference sample can be assigned a multidimensional data point, where each dimension corresponds to a different region. In one implementation, each dimension can be assigned a −1 (for a deletion), 0 (normal), or a 1 (for an amplification). Higher numbers could be possible for different levels of amplifications. The samples for a particular cancer type will cluster together, and a new sample can be assigned to a cluster. The threshold could correspond to the metric used to determine which cluster (if any) the new sample should be assigned, where the assigned cluster corresponds to the identified cancer type for the sample. For example, a cluster may have a centroid corresponding to regions of the reference patterns of the cluster shared by at least a predetermined number of reference patterns of the cluster. The cluster may include a boundary that defines which test patterns lie inside of the cluster. The boundary can have various shapes beyond simply spherical. The boundary can be determined as part of the clustering analysis when determining which reference patterns belong to which cluster, where references patterns farthest away from the centroid but within the cluster can define the boundary. The threshold for determining whether a test pattern is part of a cluster can be considered the distance from the centroid to the boundary in the direction from the centroid to the test pattern.

In yet another embodiment, the relative likelihood of having different types of cancer can be determined. The CNA pattern of a patient can be compared against the likelihood of a CNA for each type of cancer. For example, a patient has a 1q gain would be compared against the probability of the 1q gain for different types of cancers. For illustration purposes, we assume that a 1q gain may occur in 70% of HCC patients, 20% of LC patients, and 1% of CRC patients. With these likelihoods, an odds ratio can be determined based on the relative percentage of patients with different cancer types having the CNA. For instance, based on the 1q gain, the patient may be considered 3.5 times more likely to have HCC than LC and 70 times more likely to have HCC than CRC. An odds ratio for HCC to LC to CRC may be 70:20:1. One of skill would understand that this odds ratio could be expressed in several different, yet equivalent, forms. Odds ratios for different CNAs at chromosome arms other than 1q can be determined as well. An overall odds ratio may then be calculated with the likelihoods or odds ratios at the individual CNAs. In other words, given a CNA pattern from a patient and likelihoods of different types of cancer having the given CNA pattern, the likelihoods of the different types of cancer can be compared to each other in an overall odds ratio. Although this example used likelihoods of CNAs at different chromosome arms, likelihoods of CNAs at different subchromosomal regions other than chromosome arms can be used. In some embodiments, if no CNA is found at a chromosome arm or other subchromosomal region in a patient, the pattern of no CNAs can be compared against the likelihood of not finding a CNA at the chromosome arm or subchromosomal region for different types of cancer. The pattern of regions without CNAs from a patient can then be used to determine the likelihood of different types of cancer. In addition, combining the analysis of regions with CNAs and regions without CNAs can be used to determine the likelihood or relative likelihood of a type of cancer at a potentially higher accuracy than if only one type of region is used.

In another example, assume that the patient NPC1 has the plasma DNA sequenced. CNAs, including copy number gains for 2q, 12q, and 22q and copy number losses for 6q and 18q were observed. The CNA pattern of this patient matched four of the typical CNAs for NPC. By comparison, this CNA pattern matched 0, 2, 0, and 0 typical CNAs for the patterns of HCC, CRC, BrC, and LC. In another embodiment, the lack of the typical CNA for a cancer type can also be counted. For example, none of the typical CNAs for NPC were absent in this patient. In contrast, 7, 16, 13, and 8 typical CNAs for HCC, CRC, BrC and LC were absent in this patient. Therefore, the CNA pattern of this patient is not suggestive of HCC, CRC, BrC, and LC.

Figure 8A:
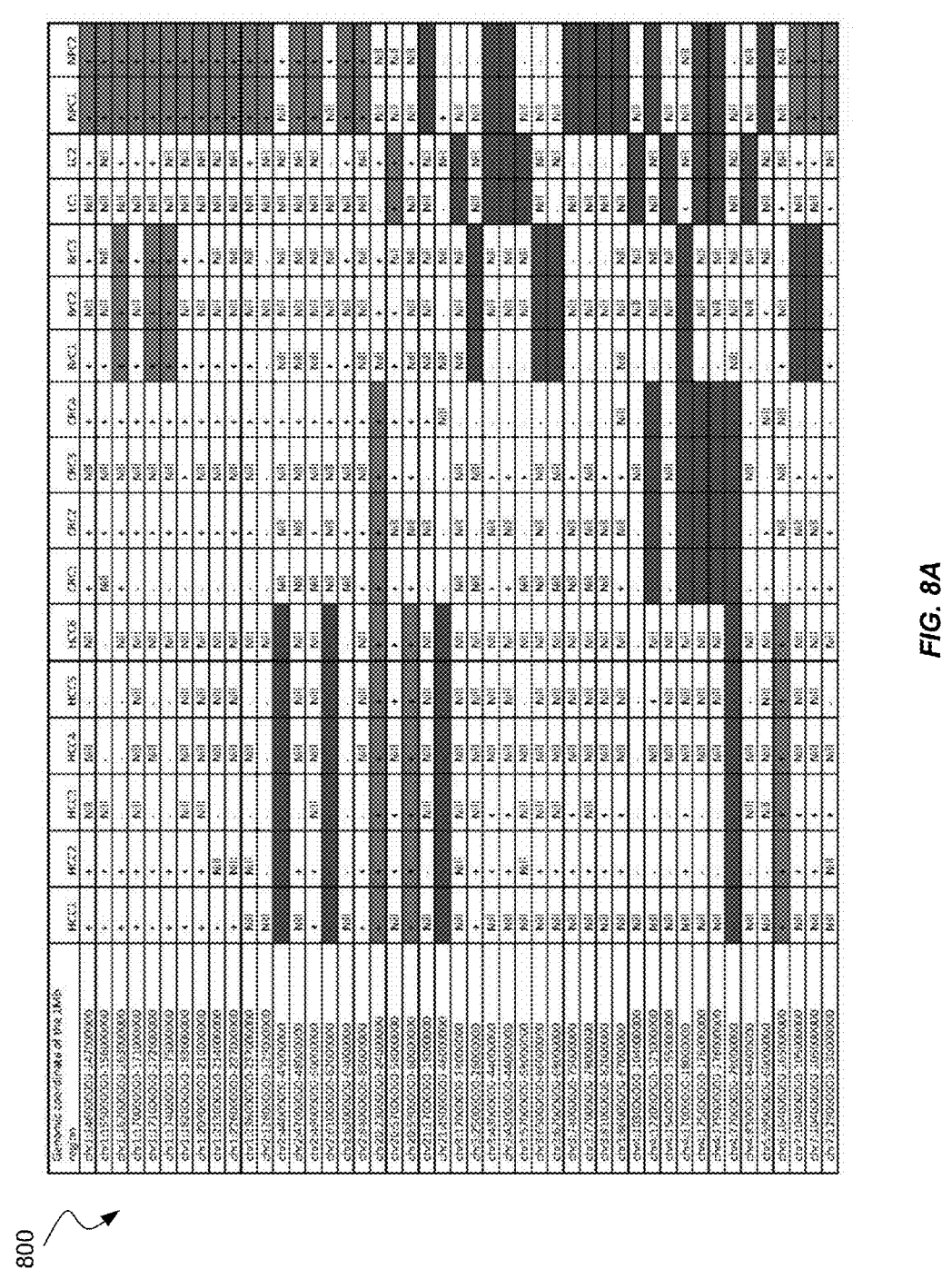
Figure 8B:
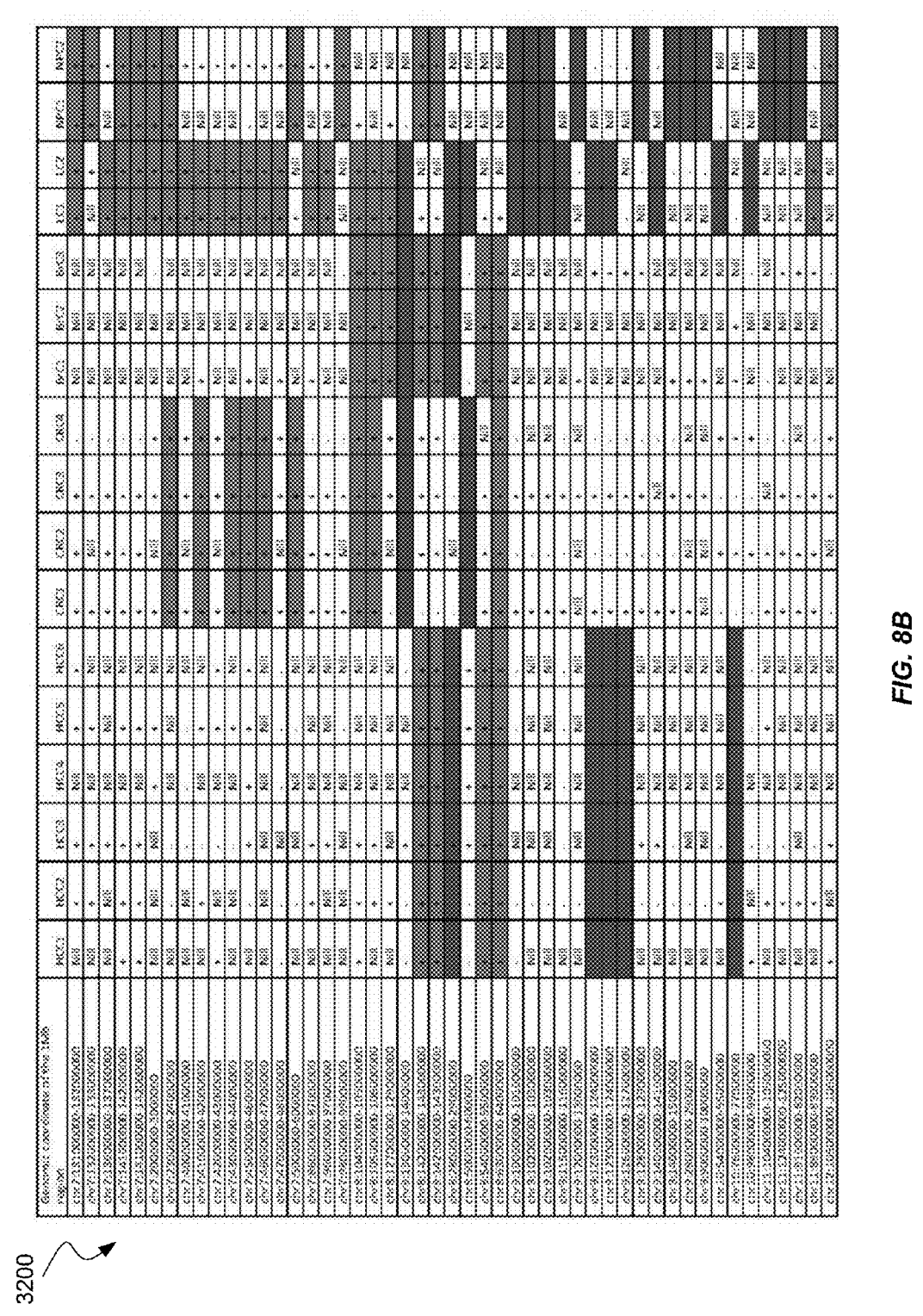
Figure 8C:
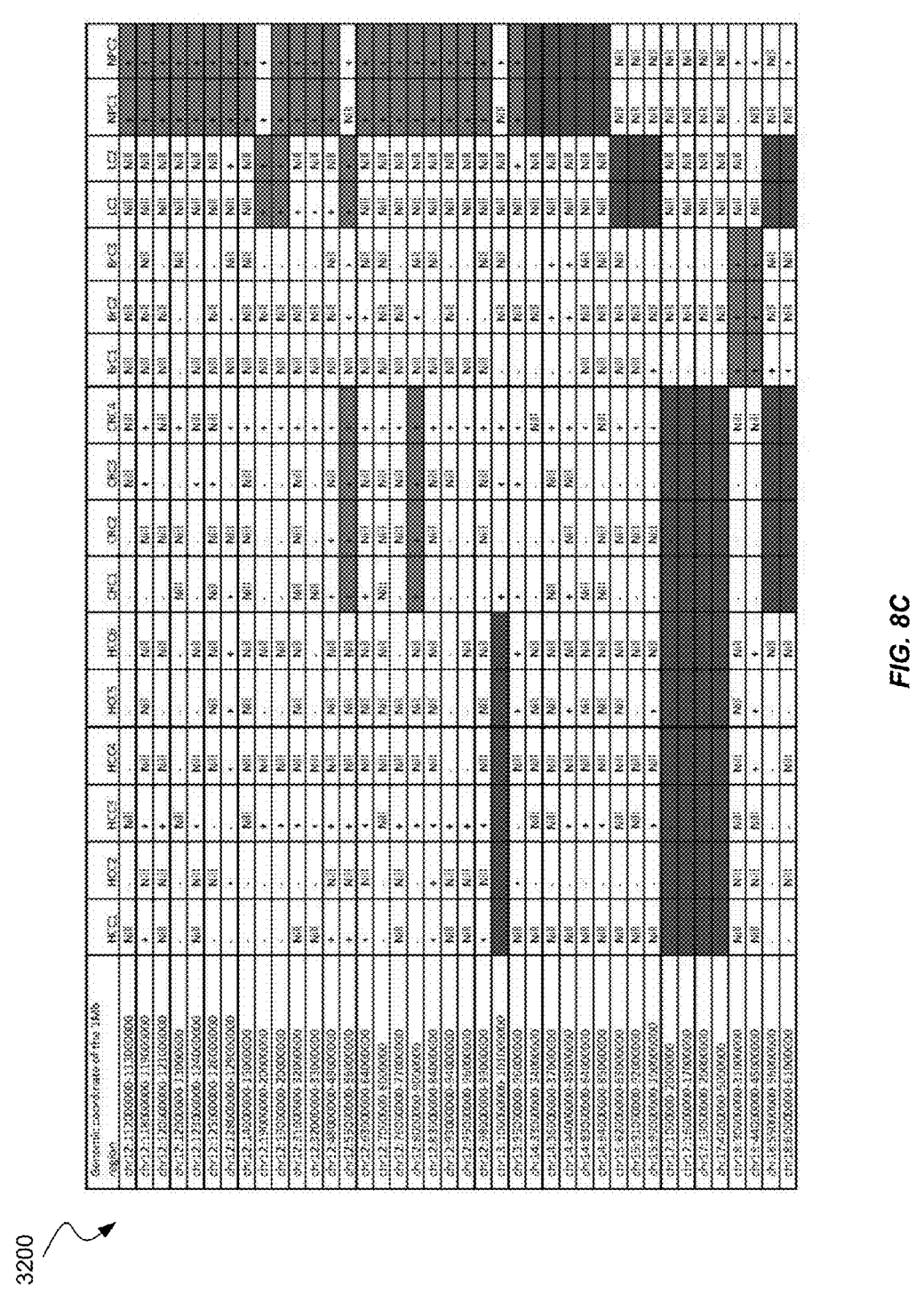

FIGS. 8A, 8B, and 8C show how the accuracy of this approach can further be enhanced by using higher resolution CNA analysis in table 800. The CNA affecting 1-Mb regions were identified in this cohort of cancer patients. Table 800 has the genomic coordinates of the 1-MB regions listed on the leftmost column. Each of the other columns lists the type of cancer and a patient number for the cancer type. A deletion is identified with '−'. An amplification is identified with '+'. A normal region is identified with 'Nil'.

In this example, the CNAs that spanned 1 Mb and were present in all the patients having the same cancer type were identified. With the higher resolution, subchromosomal CNAs that are present in a high proportion of patients with the same type of cancers can be identified. These cancer-type-specific CNAs are not identified in the arm-based analysis. For example, copy number gains on chromosome 18 spanning coordinates 30-31 Mb and 44-45 Mb were identified in all the three patients with lung cancer but were uncommon in patients with other cancer types. As discussed above, different statistical tests can be used to determine which cancer-specific CNA pattern is most similar to the tested case. Different statistical tests may include, for example, counting the number of typical CNAs in different cancer-associated CNA pattern and hierarchical clustering.

IV. SIZE ANALYSIS OF TUMOR-DERIVED DNA FRAGMENTS IN PLASMA

A statistically significant difference in the size distribution of DNA fragments can be used to identify an aberration, in a similar manner that the number of counts can. It has been reported that the size distribution of the total (i.e. tumoral plus non-tumoral) plasma DNA is increased in cancer patients (Wang B G, et al. Cancer Res. 2003; 63: 3966-8). However, if one is specifically studying the tumor-derived DNA (instead of the total (i.e. tumor plus non-tumor) amount of DNA), then it has been observed that the size distribution of tumor-derived DNA molecules is shorter than that of molecules derived from non-tumor cells (Diehl et al. Proc Natl Acad Sci USA. 2005; 102:16368-73). Therefore, the size distribution of circulating DNA can be used for determining if cancer-associated chromosomal aberrations are present.

The size analysis can use various parameters, as mentioned herein, and in U.S. Pat. No. 8,620,593. For example, the Q or F values from above may be used. Such size values do not need a normalization by counts from other regions as these values do not scale with the number of reads. Techniques involving the depth and refinement of a region may be used. In some embodiments, a GC bias for a particular region can be taken into account when comparing two regions. In some implementations, the size analysis uses only DNA molecules.

A. Method

Figure 9:
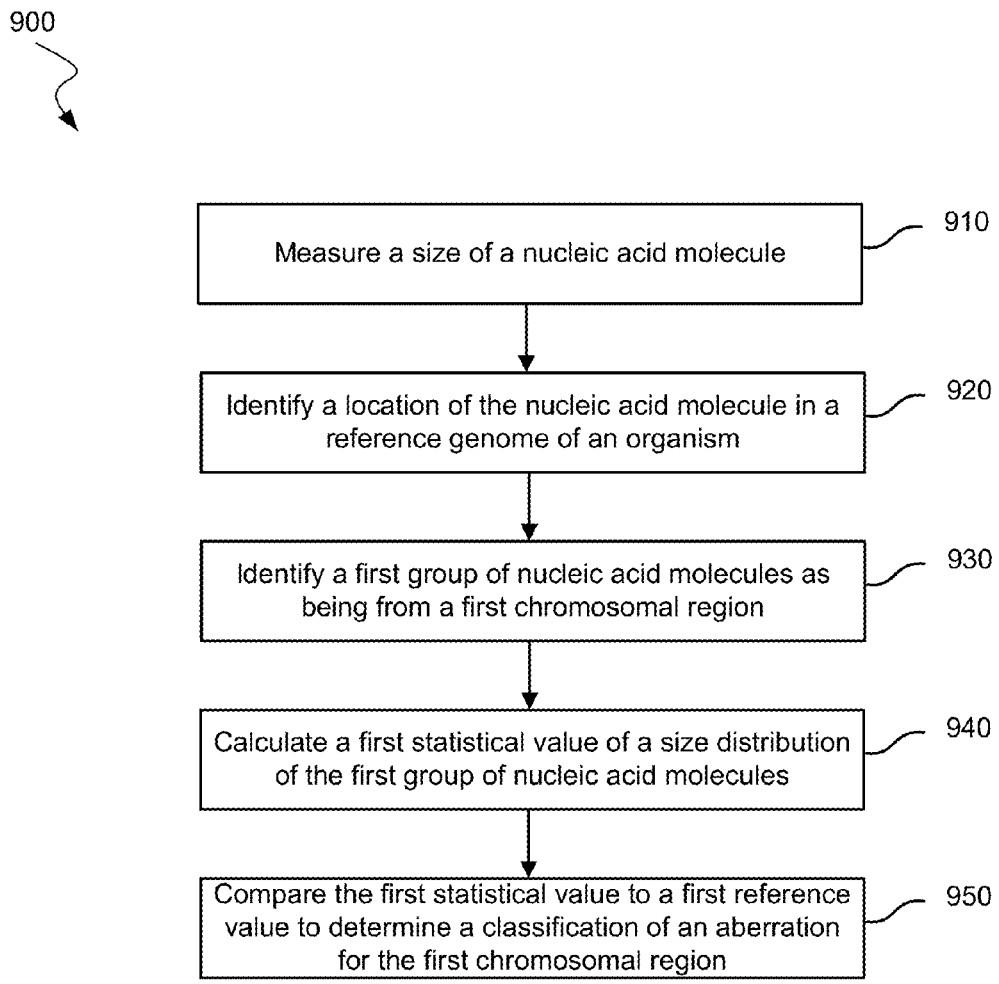
FIG. 9 shows a flowchart illustrating a method of analyzing a biological sample of an organism according to embodiments of the present invention.

FIG. 9 is a flowchart illustrating a method 900 of analyzing a biological sample of an organism according to embodiments of the present invention. The biological sample may include nucleic acid molecules originating from normal cells and potentially from cells associated with cancer. At least some of the nucleic acid molecules may be cell free in the biological sample. In one aspect, method 900 can be directed to determining a classification of a sequence imbalance based on a separation value (e.g. a difference or ratio) for the size of fragments of a first chromosome and the size of fragments of one or more reference chromosomes.

In step 910, for each of a plurality of nucleic acid molecules in the biological sample, a size of the nucleic acid molecule may be measured. Obtaining the size of a nucleic acid molecule is described in U.S. Patent Publication No. 2013/0237431 entitled "Size-Based Analysis of Fetal DNA Fraction in Maternal Plasma" by Lo et al. filed Mar. 7, 2013, the contents of which are incorporated herein by reference for all purposes.

In step 920, a location of the nucleic acid molecule in a reference genome of the organism may be identified. The location can be any part of a genome, as is described for step 120 and elsewhere. For example, it is identified which chromosome each of the plurality of nucleic acid molecules is derived. This determination can be made by a mapping to a reference genome.

In step 930, for each of the plurality of chromosomal regions, a respective group of nucleic acid molecules may be identified as being from a first chromosomal region based on the identified locations. The first chromosomal region may include a plurality of first loci.

In step 940, a computer system may calculate a first statistical value of a size distribution of the first group of nucleic acid molecules. In embodiments, the first statistical value may be determined by computing an area under a first curve at a specified size. The first curve may be a plot of a cumulative frequency of nucleic acid molecules for the first chromosomal region over a range of sizes. In one embodiment, the first statistical value can be an average, mean, median, or mode of the size distribution of the fragments corresponding to the first chromosome. In another embodiment, the first statistical value can include a sum of the length of fragments below a first size, which can be a type of cutoff. For example, each of the fragments that are smaller than 200 bp can have their lengths summed. The sum can be divided by another number, such as a sum of the lengths of all fragments corresponding to the first chromosome or a sum of the lengths of fragments greater than a second size cutoff (which may be the same as the first size). For example, the first statistical value can be a ratio of the total length of fragments below a first size cutoff relative to a total length of fragments, or a ratio of the total length of small fragments relative to a total length of large fragments.

In step 950, the first statistical value may be compared to a first reference value to determine a classification of whether the first chromosomal region exhibits an aberration. In embodiments, the first reference value may be a statistical value of a size distribution of a second group of nucleic acid molecules of a second chromosomal region. The second chromosomal region may be considered a reference chromosomal region. The first reference value may be determined by computing an area under a second curve at the specified size. The second curve may be a plot of cumulative frequency of nucleic acid molecules for the second chromosomal region over the range of sizes. In one embodiment, the first reference value may be a statistical value for a plurality of reference chromosomes. In one implementation, the statistical values can be combined such that the statistical value could be of one or more second chromosomes. In another embodiment, the statistical values for the plurality of reference chromosomes may be compared individually. The comparison may determine a classification of whether the first chromosomal region exhibits a deletion or an amplification.

The first statistical value and the first reference value may be compared to obtain a separation value. In one embodiment, the separation value can be a difference between the first statistical value and the first reference value is determined. In another embodiment, the separation value can be a ratio of the first statistical value to the first reference value. In yet another embodiment, a plurality of separation values can be determined, e.g., one for each reference value, which can be calculated for each reference chromosome.

The separation value may be a difference in the proportion of short DNA fragments between the first chromosomal region and the reference chromosomal region using the following equation:

$$\Delta F = P(\leq 150 \text{ bp})_{test} - P(\leq 150 \text{ bp})_{ref}$$

where $P(\leq 150 \text{ bp})_{test}$ denotes the proportion of sequenced fragments originating from the first chromosomal region with sizes $\leq 150$ bp, and $P(\leq 150 \text{ bp})_{ref}$ denotes the proportion of sequenced fragments originating from the reference chromosomoal region with sizes $\leq 150$ bp. In other embodiments, other size thresholds can be used, for example, but not limited to 100 bp, 110 bp, 120 bp, 130 bp, 140 bp, 160 bp and 166 bp. In other embodiments, the size thresholds can be expressed in bases, or nucleotides, or other units. In some implementations, the reference chromosomal region can be defined as all the subchromosomal regions excluding the first chromosomal region. In other implementations, the reference region can be just a portion of the subchromosomal regions excluding the first chromosomal region.

The same groups of controls used in the count-based analysis can be used in the size-based analysis. A size-based z-score of the tested region can be calculated using the mean and SD values of $\Delta F$ of the controls:

$$\text{Size-based } z\text{-score} = \frac{\Delta F_{sample} - \text{mean } \Delta F_{control}}{SD \Delta F_{control}}.$$

The separation value may be compared to one or more cutoff values. In one embodiment, the comparison can be performed for each of a plurality of separation values. For example, a different separation value can be determined between the first statistical value and each reference value. In various implementations, each separation value can be compared to the same or different cutoff values. In another embodiment, a separation value is compared to two cutoff values to determine whether the separation value is within a particular range. The range can include one cutoff to determine if a non-normal data point occurs (e.g. an aberration) and a second cutoff could be used to determine if the data point is likely caused by an error in measurement or analysis (e.g., if the separation value is larger than ever would be expected, even for a diseased sample).

A classification of whether a sequence imbalance (e.g. an aberration) exists for the first genomic location is determined based on the comparison. In one embodiment, a plurality of cutoffs (e.g. N cutoffs) can be used for a single separation value. In such an embodiment, N+1 classifications can be determined. For example, two cutoffs may be used to determine the classifications whether the chromosomal region is normal or healthy, indeterminate, or aberrant (e.g. amplification or deletion). In another embodiment where a plurality of comparisons are performed (e.g. one for each separation value), the classification can be based on each of the comparisons. For example, a rule-based method can look at the classifications resulting from each of the comparisons. In one implementation, a definitive classification is only provided when all of the classifications are consistent. In another implementation, the majority classification is used. In yet another implementation, a more complicated formula may be used based on how close each of the separation values is to a respective cutoff value, and these closeness values can be analyzed to determine a classification. For example, the closeness values could be summed (along with other factors, such as a normalization) and the result could be compared to another cutoff value. In other embodiments, variations of method 900 can also be applied to a direct comparison of a statistical value for the first chromosome to a cutoff value, which can be derived from a reference sample.

B. Correlation of Size to Cancer

Figure 10:
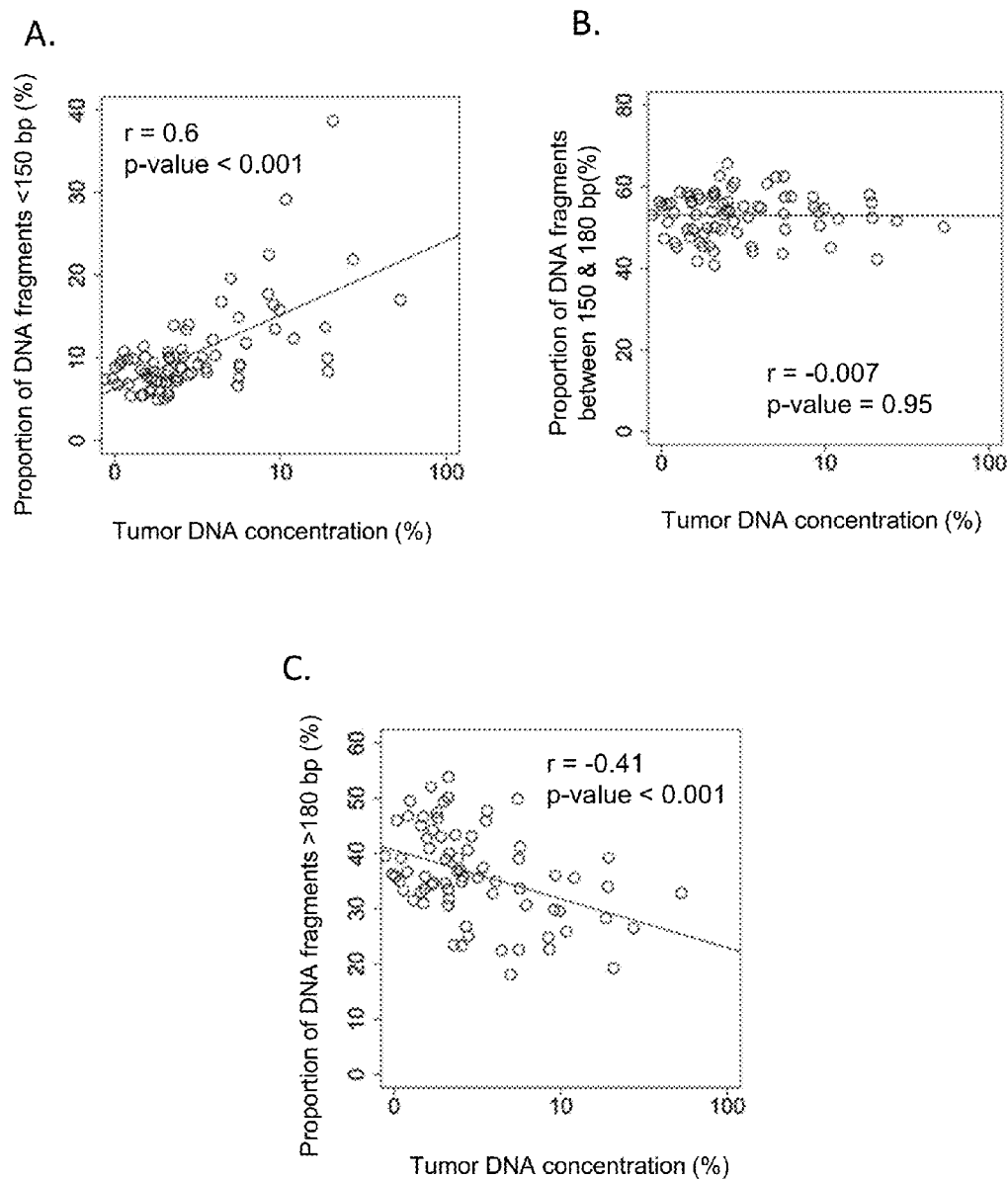
FIG. 10 shows plots of the proportions of plasma DNA fragments of (A) shorter than 150 bp, (B) from 150 to 180 bp, and (C) longer than 180 bp against tumor DNA fraction in plasma.

For further analyses, we separately explored plasma DNA molecules of three different size groups, namely, those less than 150 bp, those between 150 and 180 bp, and those above 180 bp. There is a positive correlation (Pearson's $r=0.6$; p-value $<0.001$) between the proportion of DNA fragments less than 150 bp and the tumor DNA fraction in plasma (FIG. 10A). The tumor DNA fraction in FIGS. 10A, 10B, and 10C is shown in a logarithmic scale. No correlation ($r=-0.07$; p-value=0.95) was observed between the proportion of DNA fragments with sizes between 150 and 180 bp and tumor DNA fraction in plasma (FIG. 10B). A negative correlation ($r=-0.41$; p-value $<-0.001$) was observed between the proportion of DNA more than 180 bp and tumor DNA fraction in plasma (FIG. 10C).

A lower tumor DNA fraction would more likely occur at the early stages of cancer, and a higher tumor DNA fraction would more likely occur at later stages of cancer. Thus, the existence of a larger average size (or other statistical value) than normal for DNA fragments can indicate an early-stage cancer, and existence of a smaller average size than normal for DNA fragments indicate a later stage cancer.

In other embodiments, the tumor DNA fraction can be measured. When the tumor DNA fraction is below a certain threshold, a size analysis can be performed to determine whether a statistical value of a size distribution is greater than a threshold (i.e., test whether the DNA fragments are long). When the tumor DNA fraction is above a certain threshold, a size analysis can be performed to determine whether a statistical value of a size distribution is less than a threshold (i.e., test whether the DNA fragments are short).

Methods of size analysis and data regarding the relationship of size with cancer are discussed in U.S. Patent Publication No. 2013/0040824 entitled "Detection of Genetic or Molecular Aberrations Associated with Cancer" by Lo et al. filed Nov. 30, 2011, the contents of which are incorporated herein by reference for all purposes.

V. CONFIRMING CNA ABERRATION WITH SIZE ANALYSIS

We used massively parallel sequencing to study the size profiles of plasma DNA samples at single base resolution and in a genomewide manner. We used CAZA to identify tumor-derived plasma DNA for studying their specific size profiles.

In this study, we used the CAZA approach to identify chromosomal arms that showed plasma DNA quantitative aberrations suggestive of the presence of tumor-associated CNA. After identifying the chromosome arms with amplifications or deletions, we focused on these regions as a strategy to compare tumor-derived (enriched in the amplified regions) and non-tumor derived plasma DNA (enriched in the deleted regions). We believe that this approach may provide a more robust means to identify tumoral DNA for size profiling analysis than based on the detection of cancer-associated mutations. For the latter, on average, it has been reported that there are of the order of thousands of point mutations in cancer genomes (29-32, 39). For CAZA, on the other hand, any of the myriad of plasma DNA molecules derived from the genomic regions exhibiting CNAs, totaling in terms of tens of megabases, would be useful.

A. Combined Analysis

Figure 11:
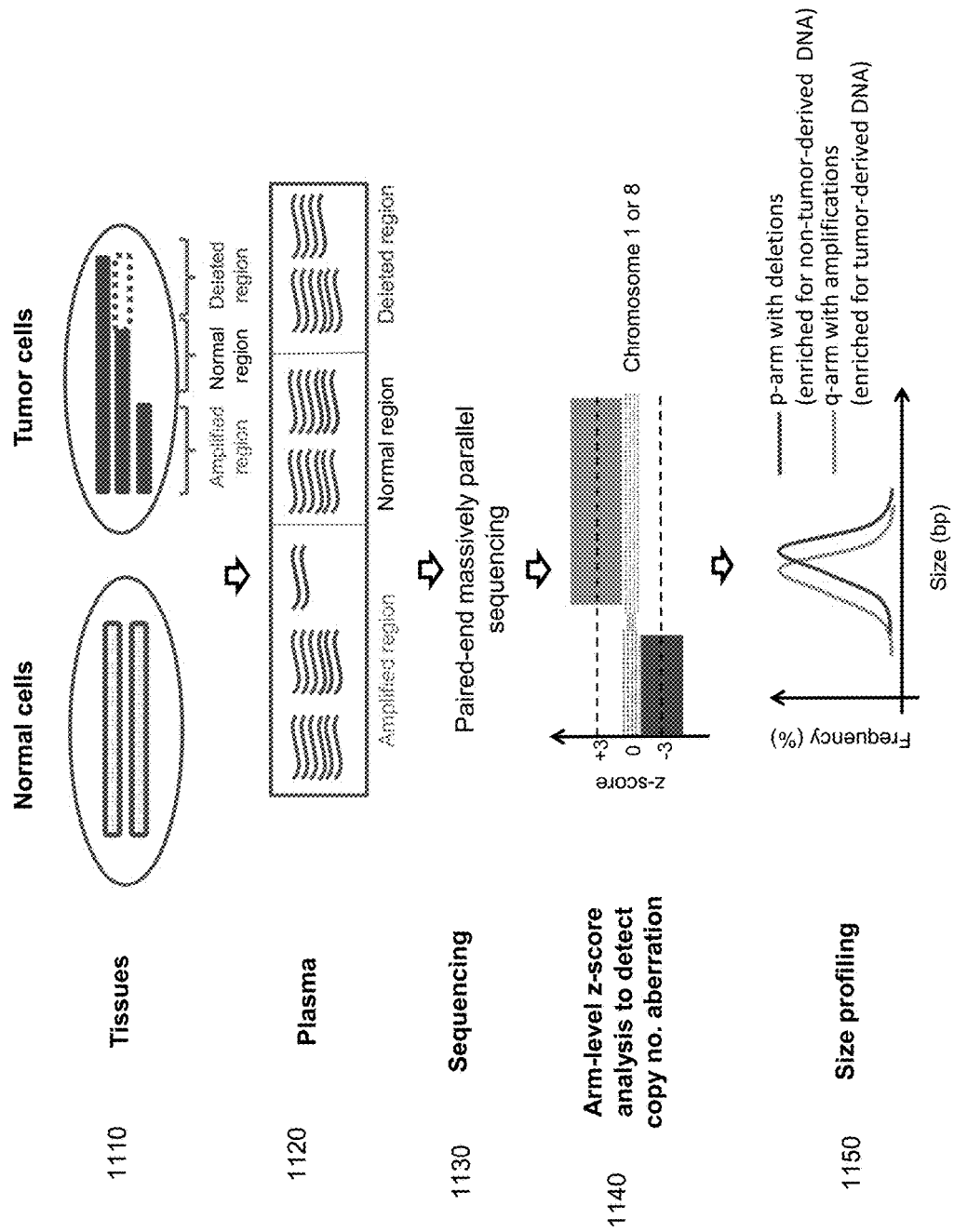
FIG. 11 is a schematic illustration of the principle of plasma DNA size analysis in cancer patients.

FIG. 11 shows a schematic illustration of the principle of plasma DNA size analysis in cancer patients. FIG. 11 shows stages 1110-2150. Stage 1110 shows the cells of the tissues in plasma. The tumor cells can include amplifications and/or deletions in various regions, as is described above. The example shows one region amplified on a particular chromosome and another region deleted.

At stage 1120, the plasma is shown with contributions from various regions. DNA fragments are shown in the plasma sample. In cancer patients, plasma DNA is derived from both tumor (red molecules) and non-tumor cells (blue molecules). Genomic regions that are amplified in the tumor tissue would contribute more tumoral DNA to plasma. Genomic regions that are deleted in the tumor tissue would contribute less DNA to plasma.

At stage 1130, paired-end sequencing is performed. The paired-end sequencing can be used to determine sizes of the DNA fragments in the plasma sample.

At stage 1140, a count-based analysis is used to identify aberrant regions. In the example shown, a CAZA analysis was used to determine if a chromosome arm is over- or under-represented in plasma DNA, suggestive of the presence of amplification or deletion of the chromosome arm in the tumor. A large positive z-score may indicate the presence of an amplification of the chromosome arm, while a large negative z-score may indicate the presence of a deletion of the chromosome arm. Other sizes of regions can be used besides the arms.

At stage 1150, the size distribution of a test region can be analyzed. As explained above, the tumor DNA fragments are shorter than DNA fragments of healthy cells. The DNA fragments of an aberrant region can be tested to confirm that the size analysis also shows a same aberration. In the example shown, a size distribution of a region exhibiting an amplification is compared to a size distribution of a region exhibiting a deletion. Thus, in some embodiments, the size profiles of plasma DNA molecules originating from chromosome arms that are under-represented (enriched for non-tumor DNA) and over-represented (enriched for tumor-derived DNA) can be compared, as described in greater detail below.

B. Size Difference Between Two Regions

To compare the size profiles of plasma DNA originating from tumor and non-tumor tissues, we analyzed the plasma DNA fragments from the chromosome arms with CNAs. Based on previous studies (34-36) as well as our findings in this study, typical CNAs associated with HCC include 1p and 8p deletions, and 1q and 8q amplifications. A HCC case (H291) with 53% tumor-derived DNA in plasma is used to illustrate the principle. This case showed 8p deletion and 8q amplification in plasma. Thus, the tumor would release more plasma DNA from the amplified region of 8q than the deleted region of 8p. As a result, 8q would be relatively enriched for tumor-derived DNA and 8p would be relatively depleted of tumor DNA (or in other words, relatively enriched for non-tumor DNA) compared with regions without CNA. The size profiles of plasma DNA for 8p and 8q are shown in FIG. 12A. The size profile for 8q was on the left side of that for 8p, indicating that the size distribution of plasma DNA for 8q was shorter than that for 8p. Because 8q is enriched with tumor DNA, the data suggest that DNA released by the tumor tends to be shorter than DNA not originating from the tumor.

To quantify the degree of shortening, cumulative frequency plots (FIG. 12B) for the size profiles for 8p and 8q were constructed for each plasma sample. These plots show the progressive accumulation of DNA molecules, from short to long sizes, as a proportion of all the plasma DNA molecules in the sample. The difference in the two curves ΔS (FIG. 12C) was then calculated as $$\Delta S = S_{8q} - S_{8p}$$

where ΔS represents the difference in the cumulative frequencies between 8p and 8q at a particular size, and $S_{8p}$ and $S_{8q}$ represent the proportions of plasma DNA fragments less than a particular size on 8p and 8q, respectively. A positive value of ΔS for a particular size indicates a higher abundance of DNA shorter than that particular size on 8q compared with 8p. Using this method, we scanned the ΔS values from 50 bp to 250 bp for all HCC cases that exhibited CNAs on 8p and 8q in plasma. The difference in cumulative frequencies, ΔS, between 8q and 8p for the HCC case H291 is plotted as a red line in FIG. 12C. Compared with the healthy controls (grey lines), all these HCC cases showed higher abundance of plasma DNA shorter than 200 bp originating from 8q (enriched for tumor DNA) than from 8p (enriched for non-tumor DNA) (FIG. 13A). FIG. 13A shows a plot of ΔS against size for all the HCC cases with different CNAs on 8p and 8q in plasma. Cases with different ranges of fractional tumor DNA concentrations in plasma are shown in different colors. As the fractional tumor DNA concentration increases, the ΔS increases, indicating a higher abundance of shorter DNA fragments. These data further support that tumor-derived DNA was shorter than that of non-tumor derived DNA.

The value of ΔS attained a maximum at 166 bp suggesting that the key difference between plasma DNA derived from tumor and non-tumor tissues is the relative abundance of DNA <166 bp and ≥166 bp. We denote this value as $\Delta S_{166}$. The $\Delta S_{166}$ was plotted for all subjects of this study, including the HBV carriers and patients with liver cirrhosis (FIG. 13B). For the HCC group, patients with and without different CNAs on 8p and 8q as determined by plasma CAZA analysis are represented by red and black dots, respectively. For almost all of the non-HCC subjects, the $\Delta S_{166}$ values were close to 0 indicating that the size distributions for DNA from 8p and 8q were similar. The $\Delta S_{166}$ (or the value at some other specified size) can be compared to a threshold, and if the difference exceeds the threshold, then at least one of the regions can be identified as exhibiting an aberration. If one region is known to not have an aberration (e.g., from CNA analysis), then the other region would be identified as exhibiting an aberration when the difference exceeds a threshold. In such an embodiment, the sign of the difference can indicate the type of aberration. For example, when the first region has an amplification and the second region does not, then the difference would be a positive number. When the first region has a deletion and the second region does not, then the difference would be a negative number. If an aberration is determined, then both regions can be identified as potentially having an aberration, with the sign indicating the type of aberration that each region may have. If the difference is big enough, it can indicate that one region has an amplification and the other region has a deletion (or amount of amplification is different), as then the difference would be larger than an amplified region compared to a normal region. The copy number analysis can provide an initial classification for the regions, so that a suitable threshold may be chosen.

Figure 14:
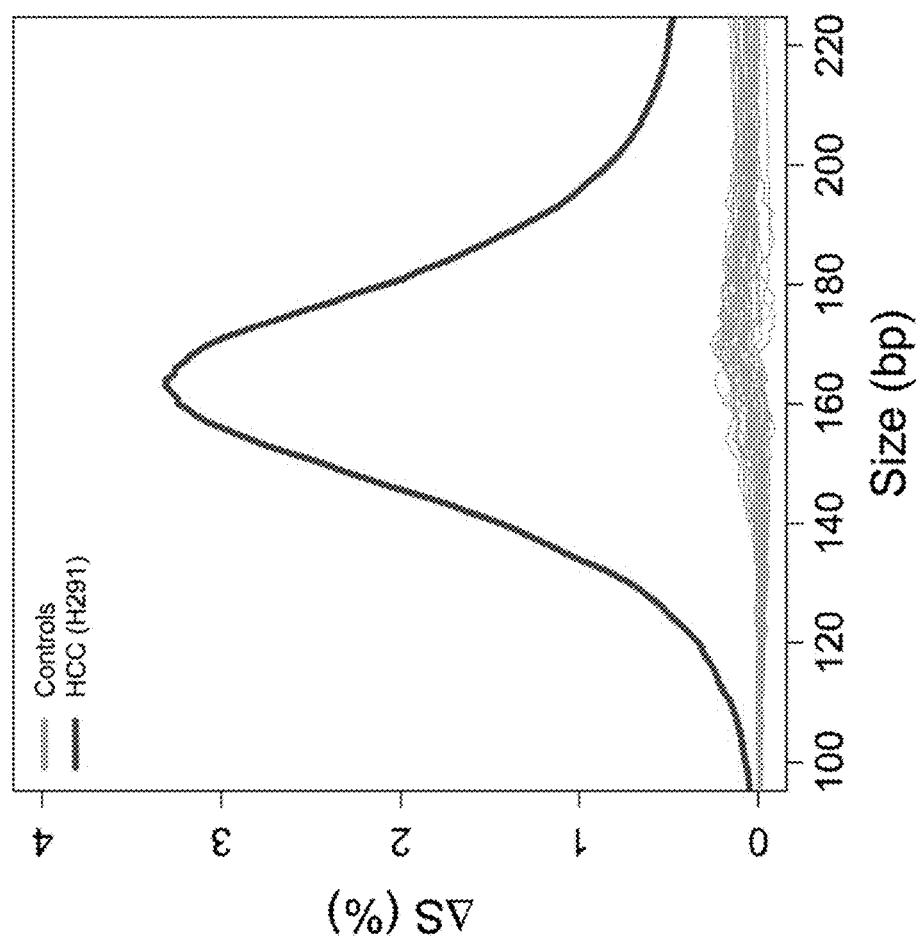
FIG. 14 is a plot of the values of $\Delta S$ between 1q and 1p against size for a representative HCC patient.
Figure 15:
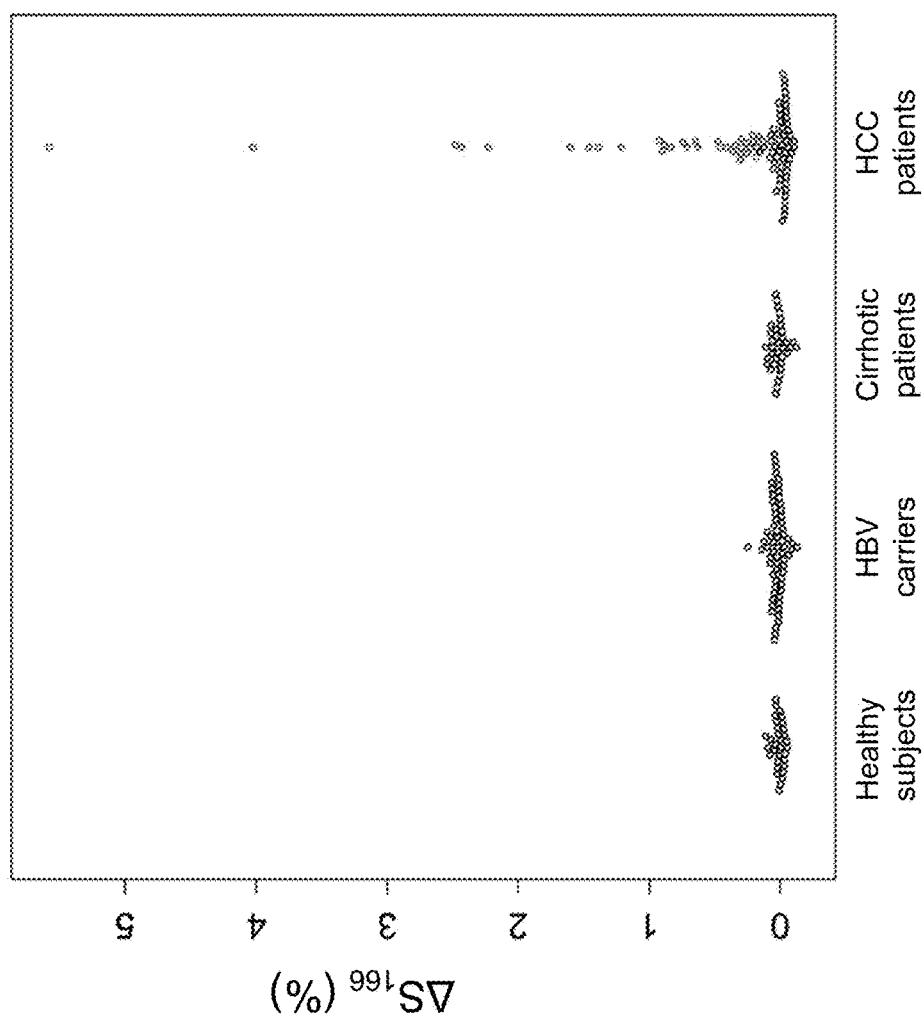
FIG. 15 is a plot of the values of $\Delta S_{166}$ between 1q and 1p for healthy control subjects, HBV carriers, cirrhotic patients and HCC patients.

Size analysis based on the plasma DNA size profiles of 1p and 1q was also performed (FIGS. 14 and 15) and showed the same trend. In FIG. 15, for the HCC group, patients with and without different CNAs on 1p and 1q as determined by plasma CAZA analysis are represented by red and black dots, respectively. This size analysis can be performed using amplified region in a normal region, or normal region and a deleted region.

In another embodiment, a size distribution for amplified or deleted region can be compared to a size distribution of one or more reference subjects that are known to have cancer or known to be healthy. The size distribution can be represented by a value, e.g., a statistical value, such as a mean or median size.

Accordingly, the aberration of a chromosomal region can be used to select particular regions for a size analysis. The size analysis of the selected regions can then be used to determine a classification of a level of cancer. The combination of using CNA and size analysis can provide greater accuracy. The CNA analysis can occasionally yield false positives, i.e., patients who do not have cancer but who have regions with copy number aberration. Thus, a patient that is identified to have cancer due to a sufficient number of regions exhibiting aberration can then be confirmed using a size analysis. In one embodiment, the selected regions are ones that have amplification.

This study was designed with an intent to explore the plasma DNA size profile of HCC patients in a high resolution and comprehensive manner which may shed light on the mechanisms related to the generation or release of plasma DNA by tumor tissues. Another goal of the study was to resolve some of the apparent inconsistencies that existed in the literature regarding cancer-associated plasma DNA size profiles. Studies have reported the presence of longer DNA in the plasma of cancer patients (20-23) while others reported higher prevalence of cancer-associated DNA mutations among the shorter plasma DNA molecules (12, 25). To achieve these study goals, a two-step approach was adopted. First, we measured the lengths of all DNA molecules in plasma samples of the recruited subjects with the use of paired-end massively parallel sequencing. This approach allows one to determine the lengths of individual plasma DNA molecules up to single base resolution. Furthermore, plasma DNA molecules across the genome could be analyzed and the relative amounts between DNA of different sizes could be determined with high precision. Hence, a broad and deep survey of the plasma DNA size profile could be obtained. Second, we took advantage of the relative difference in tumoral DNA content in plasma DNA originating from genomic locations that were associated with amplifications or deletions, the CAZA approach, as a means to identify tumor-derived plasma DNA for detailed analysis.

Figure 16:
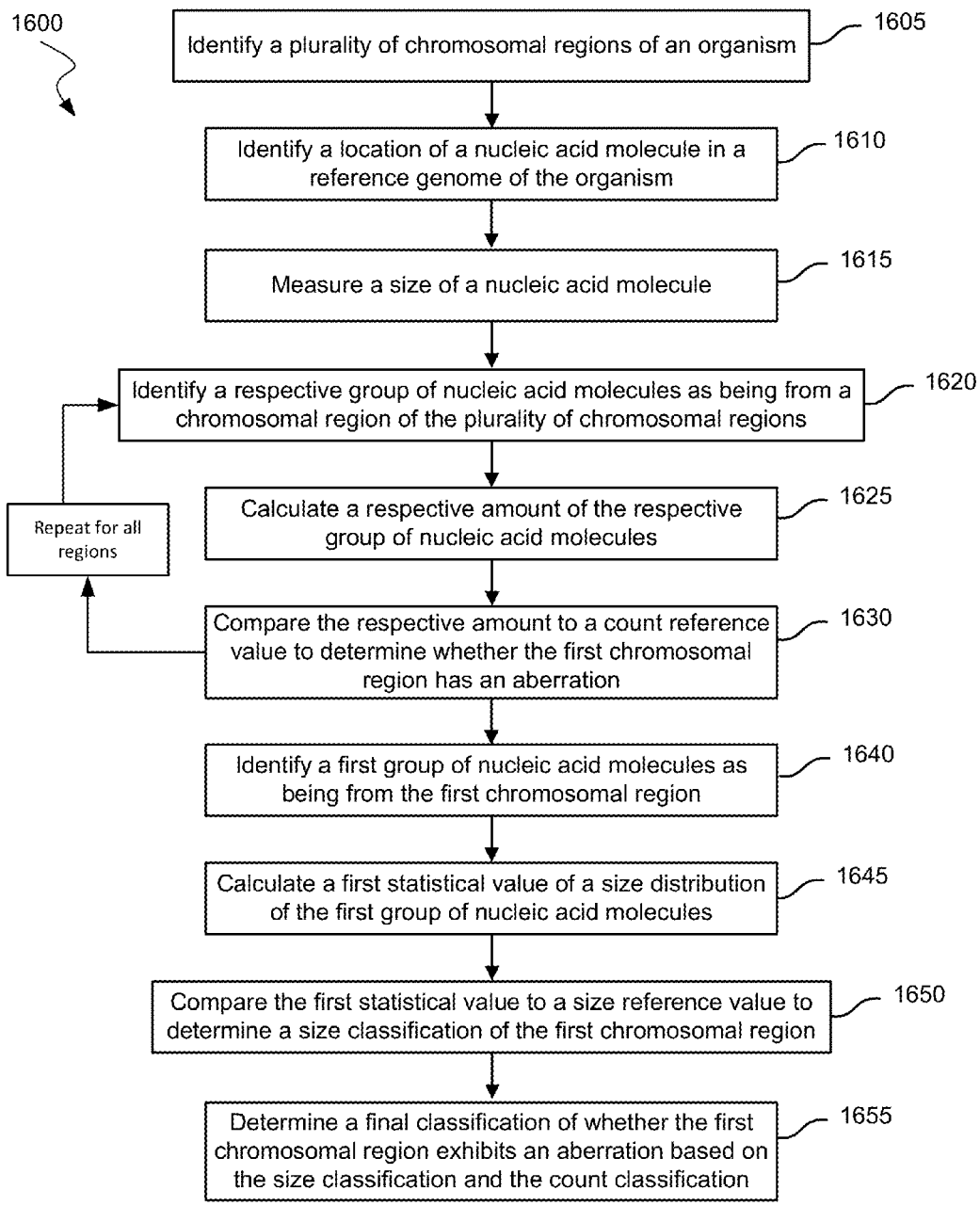
FIG. 16 is a flowchart illustrating a method of performing chromosome arm-level z-score analysis (CAZA) and size analysis in order to analyze a biological sample of an organism according to embodiments of the present invention.

This study provides a number of insights into the biological mechanisms that might be involved in the release of plasma DNA. Plasma DNA of all recruited subjects, including the HBV carriers, patients with liver cirrhosis or HCC, exhibited a prominent peak at 166 bp (FIGS. 14 and 16). This pattern is analogous to observations in the plasma of pregnant women and organ transplant recipients (26, 27). The presence of the characteristic 166 bp peak in the plasma DNA size profile of all groups of patients studied suggests that most of the circulating DNA molecules in human plasma, including that of pregnant women, transplant recipients, patients with HCC, liver cirrhosis or chronic HBV, resemble mononucleosomal units and are likely to originate from the process of apoptosis.

Figure 13:
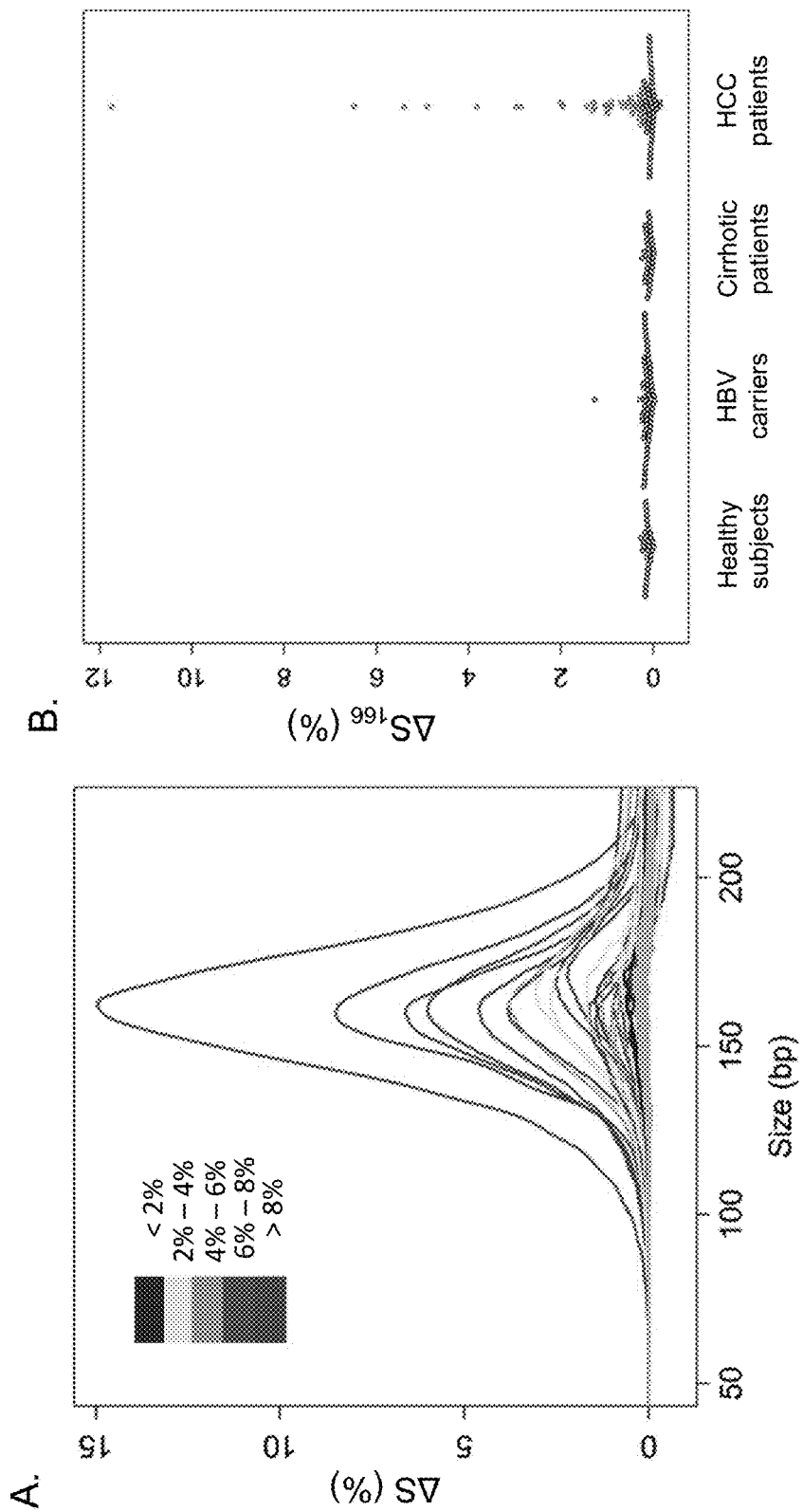
FIG. 13 shows the difference in the cumulative frequencies for size between 8q and 8p ($\Delta S$). (A) Plot of $\Delta S$ against size for all the HCC cases with different CNAs on 8p and 8q in plasma. (B) The values of $\Delta S_{166}$ amongst different groups.

The study of the size profile of plasma DNA molecules bearing tumor-associated CNAs indicates that such molecules are shorter than those not carrying such signatures (FIG. 13). This is consistent with our observation that with increasing fractional concentrations of tumor DNA in plasma, the size profile of plasma DNA would shift towards the left. However, the fact that HCC patients with low fractional concentrations of tumor DNA in plasma had an apparently longer size distribution than healthy controls suggest that there was an additional component of plasma DNA that did not carry the tumor-associated genomic signatures. It is possible that this component would be derived from the non-neoplastic liver tissues surrounding the tumor. These long DNA molecules could be derived from necrosis instead of apoptosis. It has been reported that cell death associated with tissue necrosis may generate longer DNA fragments in addition to the typical oligonucleosomal DNA fragments (37, 38). For future studies, it would be interesting to study the DNA methylation profile of these longer DNA molecules to see if they bear resemblances to that expected for the liver.

We showed that populations of aberrantly short and long DNA molecules co-existed in the plasma of patients with hepatocellular carcinoma. The short ones preferentially carried the tumor-associated copy number aberrations.

In summary, we profiled the size distribution of plasma DNA in patients with HCC at single-nucleotide resolution. We have demonstrated a difference in the size of plasma DNA derived from tumor and non-tumor tissues.

Figure 30:
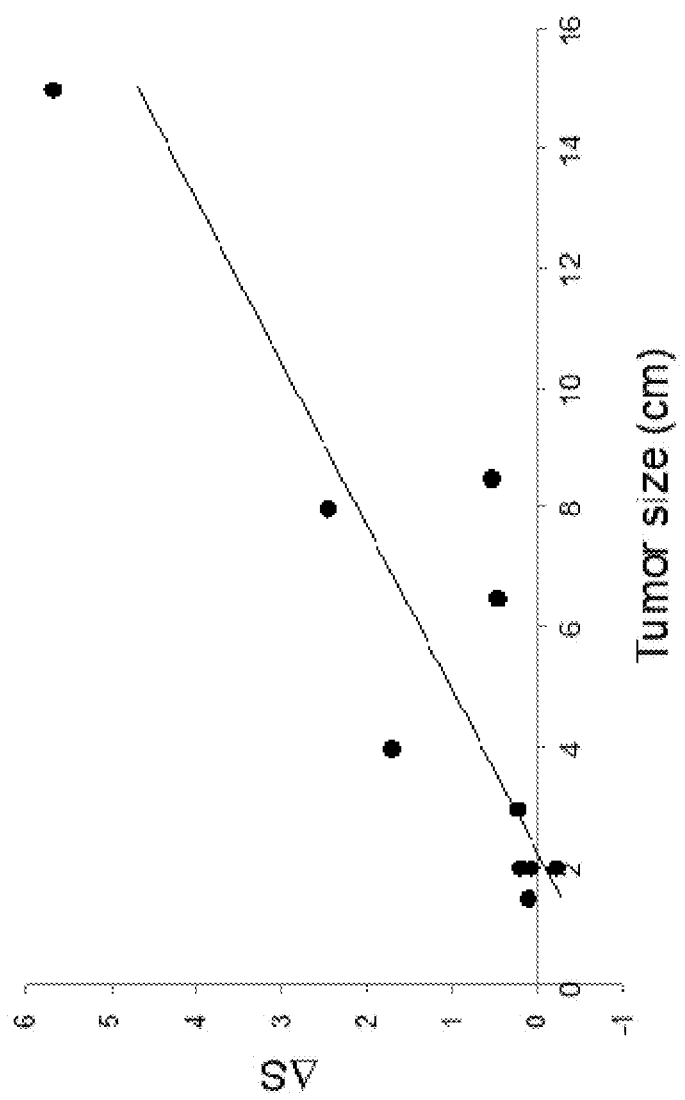
FIG. 30 is a plot of $\Delta S$ versus tumor size of HCC patients.

The relationship between $\Delta S$ and tumor size was also analyzed. The plasma DNA samples of 10 HCC patients with 8p deletion and 8q amplification in plasma were analyzed using $\Delta S$ analysis. The $\Delta S$ was determined for the size difference between the plasma DNA fragments mapping to 8p and 8q. A positive value for $\Delta S$ indicates the more abundance of short DNA fragments below 150 bp for 8q compared with 8p. In FIG. 30, the values of $\Delta S$ were plotted against the longest dimension of the tumor of the HCC patients.

A positive correlation between $\Delta S$ and tumor size was observed (r=0.876, Pearson correlation). This observation suggests that the size distribution of plasma DNA fragments from regions exhibiting different types of CNAs can be used to reflect the size of the tumor in HCC patients.

Figure 31:
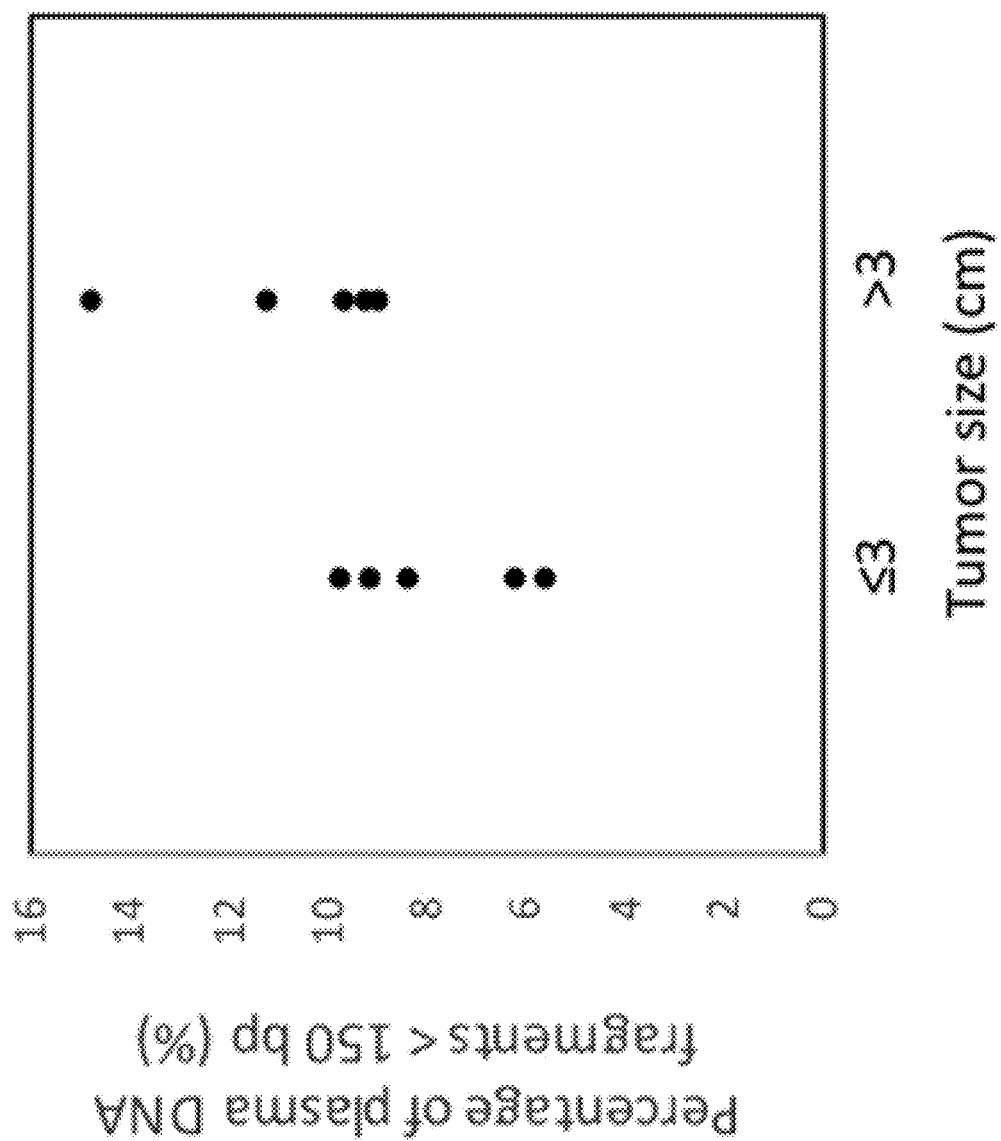
FIG. 31 is a plot of the percentage of DNA fragments of a certain size against tumor size.

The overall size distribution of the total plasma DNA was also analyzed for these 10 HCC patients. The percentage of plasma DNA fragments of less than 150 bp (P(<150)) was determined for each case and plotted against tumor size in FIG. 31. The proportion of short fragments was significantly higher in patients with larger cancer of more than 3 cm in the largest dimension. In one embodiment, the proportion of short fragments can be used to reflect the size and severity of the cancer. In other implementations, other cutoffs for size can be used, for example, but not limited to 100 bp, 110 bp, 120 bp, 130 bp, 140 bp, 160 bp and 166 bp.

A calibration function may be used to provide a relationship between size of the tumor and a statistical value. The calibration function may be determined from calibration data points of reference samples from organisms with tumors of known size. The calibration data point may include a measurement of the size of the tumor and a corresponding statistical measurement of sizes of nucleic acid molecules from a chromosomal region. When a new sample is obtained from a new subject, the statistical value may be determined, and the calibration function may be used to convert the statistical value into a tumor size. An example of a calibration function is a linear fit, similar to the linear fit shown in FIG. 30. Other types of regression analysis, such as a least squares fit, may be used to generate the calibration function.

The calibration function be defined in a variety of ways, e.g., as a plurality of coefficients of a specified function, such as a linear or non-linear function. Other embodiments can store a plurality of calibration data points (e.g., data points of the calibration function) so that the calibration function can be generated. Further, an interpolation can be performed between such calibration data points to obtain the calibration function. The calibration function may be stored in and retrieved from computer memory.

C. Method

FIG. 16 is a flowchart illustrating a method 1600 of performing CAZA and size analysis in order to analyze a biological sample of an organism according to embodiments of the present invention.

In step 1605, a plurality of chromosomal regions of an organism may be identified. Each chromosomal region may include a plurality of loci. One of the plurality of chromosomal regions may be selected as a first chromosomal region. Identifying the plurality of chromosomal regions may be similar to step 610 of FIG. 6.

In step 1610, a location of a nucleic acid molecule in a reference genome of the organism may be identified for each of a plurality of nucleic acid molecules. Identifying the location of the nucleic acid molecule may be performed in a similar manner as step 620 of FIG. 6.

In step 1615, a size of a nucleic acid molecule may be measured for each of the plurality of nucleic acid molecules in the biological sample. The size of the nucleic acid molecule may be measured similar to step 910 of FIG. 9.

In step 1620, a respective group of nucleic acid molecules may be identified, based on the identified locations, as being from a chromosomal region for each chromosomal region of the plurality of chromosomal regions. The respective group may include at least one nucleic acid molecule located at each of the plurality of loci of the chromosomal region. Identification of the respective group of nucleic acid molecules may be similar to step 120 of FIG. 1.

In step 1625, a computer system may calculate a respective amount of the respective group of nucleic acid molecules. Calculating the respective amount may be similar to the calculation in step 130 of FIG. 1.

In step 1630, the respective amount may be compared to a count reference value to determine a count classification of whether the chromosomal region exhibits an amplification. Based on the comparison, the first chromosomal region may be identified as potentially exhibiting an aberration. Steps 1620-1630 may be performed in a similar manner as steps 120-140 of FIG. 1 or steps 630-650 of FIG. 6.

In step 1640, a first group of nucleic acid molecules may be identified as being from the first chromosomal region.

In step 1645, a computer system may calculate a first statistical value of a first size distribution of the first group of nucleic acid molecules. The first statistical value may be determined by computing an area under a first curve at a specified size. The first curve may be a plot of cumulative frequency of nucleic acid molecules for the first chromosomal region over a range of sizes. Calculating the first statistical value in step 1645 may be similar to calculating the first statistical value in step 940 in FIG. 9.

In step 1650, the first statistical value may be compared to a size reference value to determine a size classification of whether the first chromosomal region exhibits an aberration. The size reference value may be determined by computing an area under a second curve at the specified size. The second curve may be a plot of cumulative frequency of nucleic acid molecules for the second chromosomal region over the range of sizes. The comparison may be based on a difference between the two curves. In some embodiments, comparing the first statistical value to the size reference value may be similar to step 950 in FIG. 9.

In step 1655, a final classification of whether the first chromosomal region exhibits an aberration may be determined. For example, at least one of the size classification and count classification can be used to determine whether the aberration exists for the first chromosomal region. In some embodiments, the final classification may be that the first aberration exists only when the count classification and the size classification indicate the same aberration. Thus, the comparison of the first statistical value to the size reference value may confirm whether the first chromosomal region exhibits an aberration. In some embodiments, a set of size classifications may be determined for a set of chromosomal regions identified as aberrant based on corresponding count classifications. Based on the set of size classifications, each of the chromosomal regions may be confirmed as aberrant or not aberrant.

In some embodiments, the final classification of whether the first chromosomal region exhibits an aberration may be based on multiple count reference values and multiple size reference values. Each of the count reference values can correspond to a different count classification (e.g., a discrimination between a unique pair of count classification, such as between level 1 and level 2, or between level 2 and level 3). Similarly, each of the size reference values can correspond to a different size classification. The final classification can be determined from the particular combination of size classification and count classification.

The size classification may include multiple classifications depending on a statistical value of the size distribution. For example, a large difference between the statistical value and a size reference value may result in a size classification corresponding to a high likelihood of an aberration, while a small difference between the statistical value and the size reference value may result in a size classification corresponding to a low likelihood of an aberration. Similarly, the count classification may include multiple classifications depending on the amount of a group of nucleic acid molecules. For example, a large difference between the amount of a group of nucleic acid molecules compared to a count reference value may result in a count classification corresponding to a high likelihood of an aberration, while a small difference may result in a count classification corresponding to a low likelihood of an aberration.

Accordingly, the final classification may be based on different thresholds for different size classifications and count classifications. For instance, a size classification indicating a high likelihood of an aberration may result in a final classification indicating an aberration given a count classification indicating a certain, possibly low, likelihood of an aberration. As the likelihood of an aberration as indicated by one of the size classification or the count classification increases, then the threshold for the likelihood indicated by the other classification is lowered. In some cases, one classification may show a high likelihood of a first type of aberration, the other classification may show a low likelihood of a second type of aberration, and the final classification may indicate that the first type of aberration is present. In some cases, the final classification may correspond to a likelihood or probability of an aberration.

D. Example Cases

The specificity of the detection of cancer-associated CNA can be improved by plasma DNA size analysis, as shown in the following two cases. Case 1 was a patient with hepatitis B-associated cirrhosis, and Case 2 was a chronic carrier of hepatitis B infection. Both of them were not known of having any cancer at the time of recruitment. They had been followed clinically for two years since recruitment and no cancer was detected. Venous blood was collected from each of the two subjects at recruitment. The plasma DNA was sequenced. CNA involving chromosome 1q was detected in each of these two patients. For Case 1, the z-score for 1p and 1q were −2.3 and 15.5, respectively. These results are consistent with the interpretation of 1q amplification. In the plasma DNA fragment size analysis, the ΔS was −0.019. The negative value of ΔS indicates that short DNA fragments were less abundant in 1q compared with 1p. As the count-based analysis suggests that 1q was amplified, the size-based analysis result is opposite to what we expected for cancer-associated CNAs. In cancer patients, regions with copy number gain are expected to show an overall shorter size distribution due to the presence of more cancer-derived short fragments compared with regions with amplification or regions without any CNA. Therefore, the size analysis in this case is not suggestive of the presence of cancer-associated CNAs in the plasma DNA.

For Case 2, the z-scores for 1p and 1q were 0.4 and −4.4, respectively. These results are compatible with the interpretation of 1q deletion. In the plasma DNA fragment size analysis, the ΔS was 0.044. The positive value of ΔS indicates that short DNA fragments were more abundant in 1q compared with 1p. As the count-based analysis suggests that 1q was deleted, the size-based analysis result is opposite to what we expected for cancer-associated CNAs. In cancer patients, regions with copy number loss are expected to show an overall longer size distribution due to the presence of less cancer-derived short fragments compared with regions with amplification or regions without any CNA. Therefore, the size analysis in this case is not suggestive of the presence of cancer-associated CNAs in the plasma DNA.

VI. DETERMINATION OF STAGES OF CANCER

As mentioned above, the size of the DNA fragments can indicate the stage of the cancer. A later stage of cancer exhibits smaller fragments for regions exhibiting amplification.

Apart from the intrinsic biological interest, plasma DNA size profiling may also be useful for the development of diagnostic approaches for detecting cancer-associated changes in plasma. For example, enrichment of tumoral DNA from plasma may be achieved by focusing on the analysis of short DNA fragments. In addition, we observed that the proportion of short DNA molecules bore a positive relationship with the fractional concentration of tumor-derived DNA in plasma. The changes in size profiles can be used for the monitoring of patients during the course of treatment. Furthermore, the presence of the population of long DNA molecules in the plasma of the patients with and without HCC warrants further investigation. When the tissue source or pathological process that governs the release of these DNA molecules are better understood, measuring the proportion of long DNA in plasma might be useful for the assessment of such diseases.

A. Plasma DNA Size Distribution of HCC Patients

Figure 18:
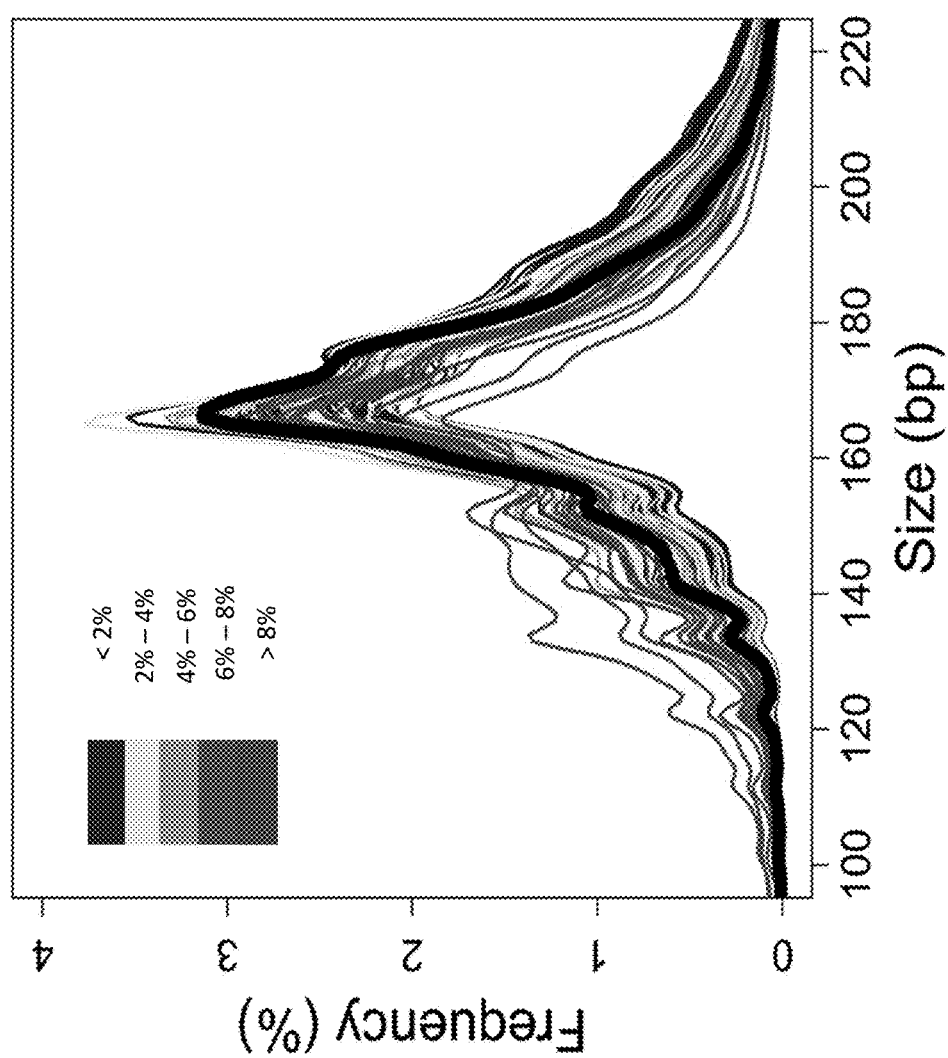
FIG. 18 shows size distributions of plasma DNA fragments in the HCC patients with different fractional concentrations of tumor-derived DNA in plasma.
Figure 19:
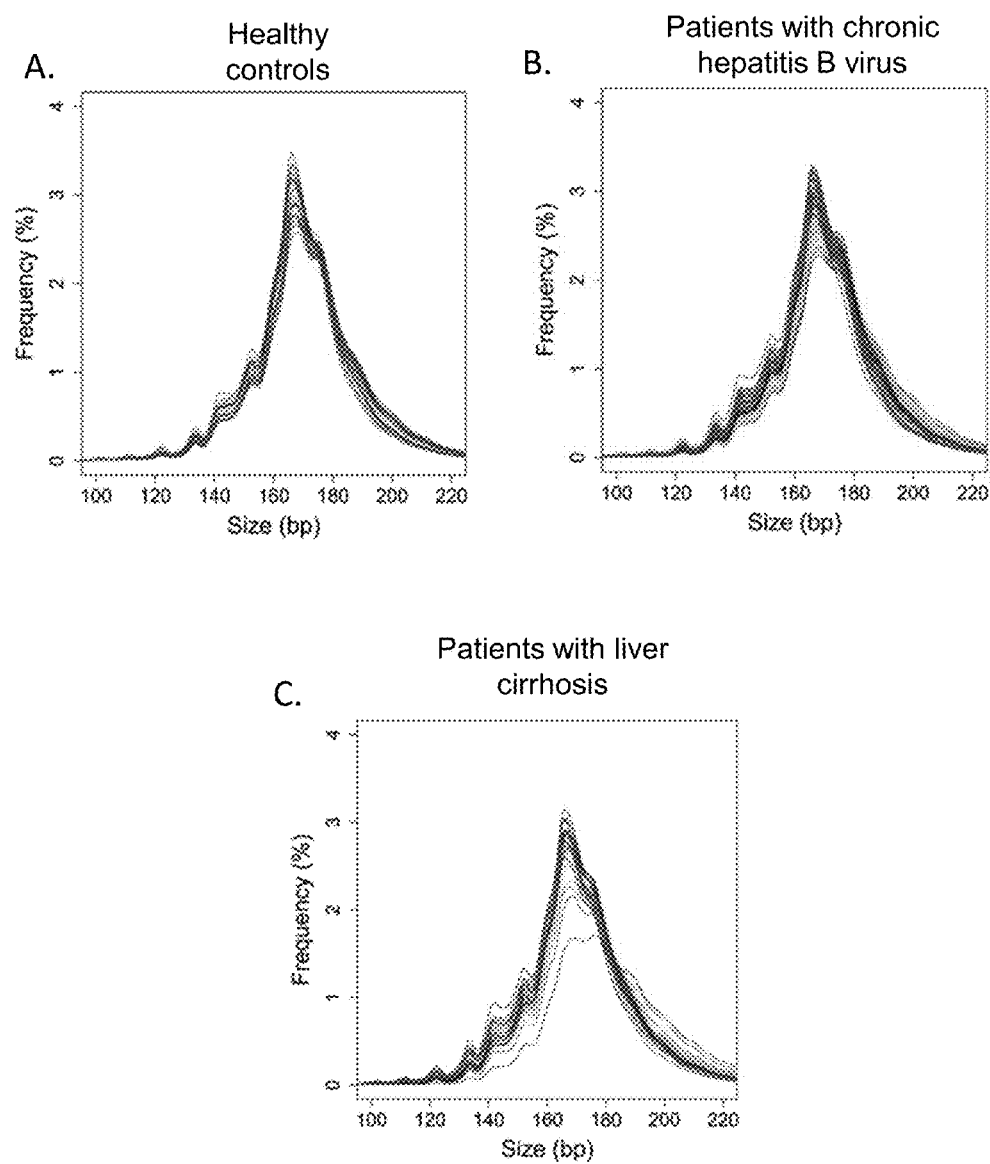
FIG. 19 shows size profiles of plasma DNA for (A) healthy controls, (B) chronic HBV carriers, and (C) cirrhotic patients.

The size distributions of plasma DNA of the HCC patients, HBV carriers, cirrhosis patients and healthy controls are shown in FIGS. 18 and 19. In FIG. 19, each individual is represented by a different color. In general, the most prominent peak was observed at 166 bp in the size distribution plot of each subject. This observation is consistent with previous reports on pregnant women and transplant recipients (26-28), suggesting that most of the circulating DNA molecules are derived from apoptosis. Interestingly, when compared with the median size distribution profile for 32 healthy controls (thick black line in FIG. 18), the sizes of plasma DNA in HCC patients with low fractional tumor DNA concentrations were longer. However, with increasing fractional concentrations of tumor DNA in plasma, the size distribution of plasma DNA shifted progressively to the left (FIG. 18).

As described earlier, FIG. 13A is a plot of ΔS against size for all the HCC cases with different CNAs on 8p and 8q in plasma. As the fractional tumor DNA concentration in plasma increases from less than 2% to over 8%, the ΔS increases, indicating a higher abundance of shorter DNA fragments. The fractional tumor DNA concentration in plasma may increase as the stage of cancer progresses. As a result, the amount of shorter DNA fragments may indicate a later stage of cancer. FIG. 13B shows that $\Delta S_{166}$ is higher for HCC patients, compared to non-HCC subjects, indicating that the relative abundance of DNA <166 bp and ≥166 bp may be used to indicate the presence of cancer. Accordingly, $\Delta S_{166}$ may also indicate the stage of cancer.

Figure 20:
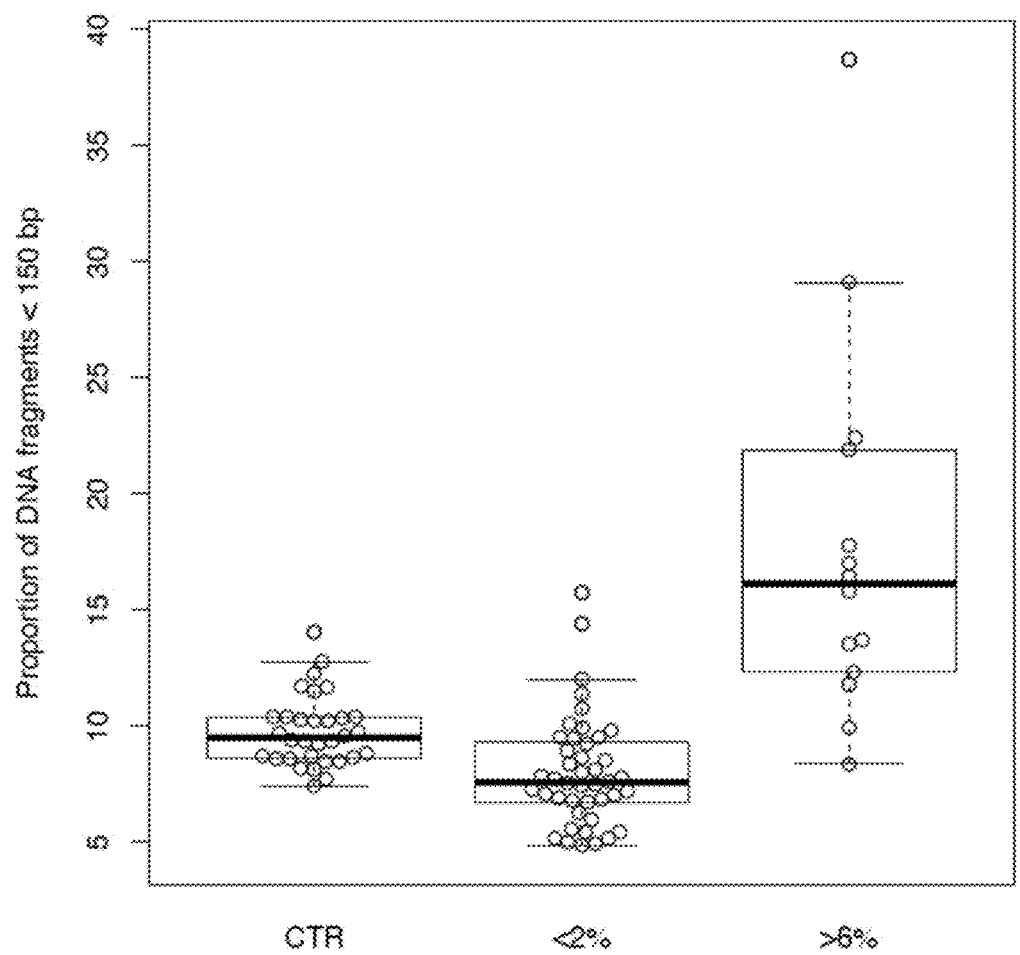
FIG. 20 shows boxplots of the proportion of short fragments for healthy control subjects, HCC patients with tumor DNA fraction of less than 2% in plasma, and HCC patients with tumor DNA fraction of greater than 6%.

FIG. 20 shows an example of when the proportion of short fragments can be used to differentiate HCC patients from healthy control subjects. The proportion of plasma DNA fragments less than 150 bp was plotted for 32 healthy subjects, HCC patients with tumor DNA fraction of less than 2% in plasma and HCC patients with tumor DNA fraction of greater than 6% in plasma. Compared with healthy control subjects (labeled as 'CTR'), HCC patients with tumor DNA fraction of less than 2% had significantly lower proportion of short DNA fragments of less than 150 bp (p=0.0002, t-test), and those with tumor DNA fraction of greater than 6% had significantly higher proportion of short fragments (p=0.003, t-test). HCC patients with a tumor DNA fraction from 2% to 6% have a proportion of DNA fragments between HCC patients with a tumor fraction of less than 2% and HCC patients with a tumor fraction greater than 6%. In this manner, HCC patients with the tumor fraction from 2% to 6% may have a distribution similar to the healthy control subjects.

Figure 21:
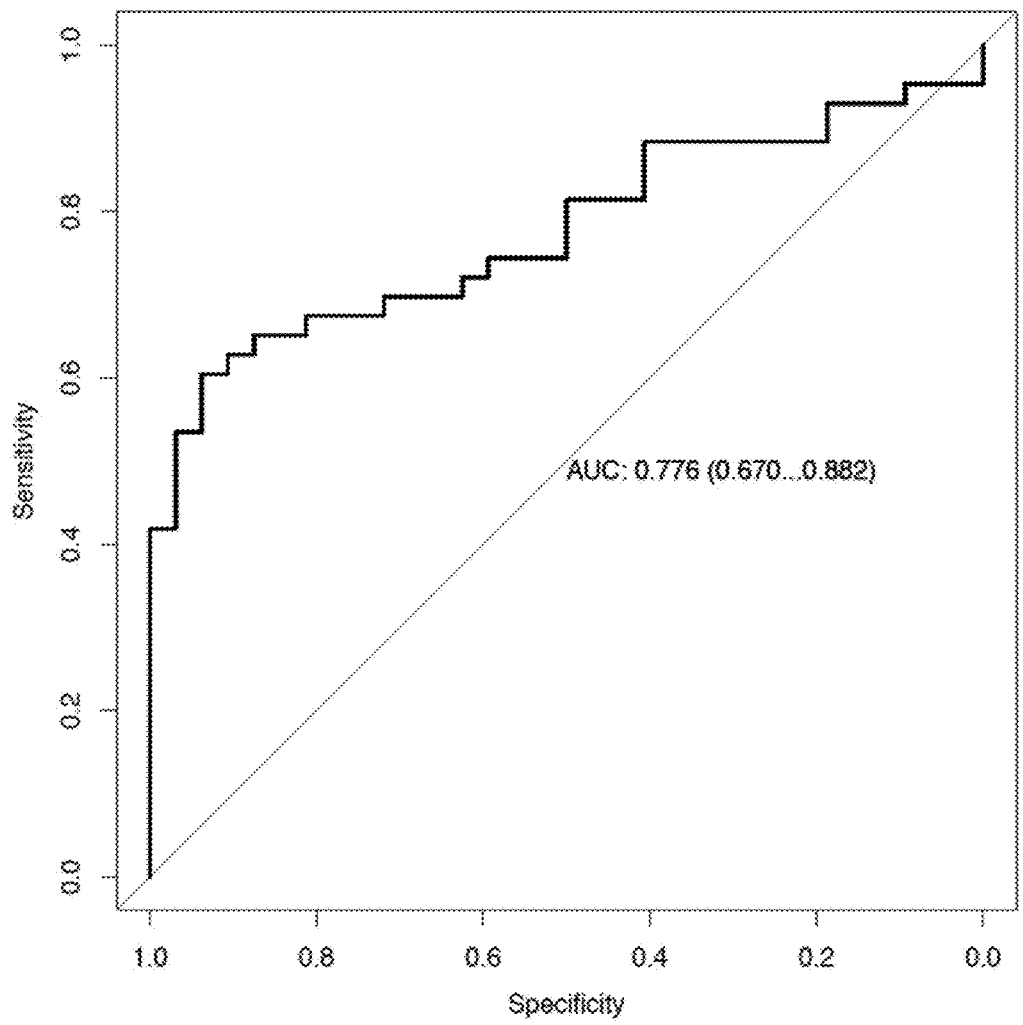
FIG. 21 is a receiver operating characteristic (ROC) curve for applying P(<150) to differentiate HCC patients with less than 2% tumor DNA fraction from healthy control subjects.

FIG. 21 shows a receiver operating characteristic (ROC) curve for applying P(<150) to differentiate HCC patients with less than 2% tumor DNA fraction from healthy control subjects. The tumor fraction was determined based on the magnitude of under-representation of the chromosome regions exhibiting under-representation in the plasma that were compatible with a copy number loss in the tumor. For cases without significant under-representation of any chromosome arm, the magnitude of over-representation for regions that were compatible with copy number gain was used to determine the tumor fraction with an assumption of single copy gain. The tumor fraction can be determined with the following equation:

$$\text{Tumor fraction} = \frac{|P_{test} - P_{normal}|}{P_{normal} \times \Delta N / 2}$$

where $P_{test}$ represents the proportion of fragments mapped to the chromosome arm of interest for the test case, $P_{normal}$ represents the mean proportion of fragments mapped to the chromosome arm for the healthy controls, and $\Delta N$ represents the magnitude of the copy number change (e.g., 1 for either a duplication or a deletion, and higher numbers for higher order amplifications). The area under the curve (AUC) was 0.776 with 95% confidence limits of 0.670 and 0.882. This result indicates that size analysis can be used to identify HCC patients with tumor fraction of less than 2% in plasma. ROC curve analysis indicates that different thresholds can be selected to achieve different sensitivities and specificities.

Figure 22:
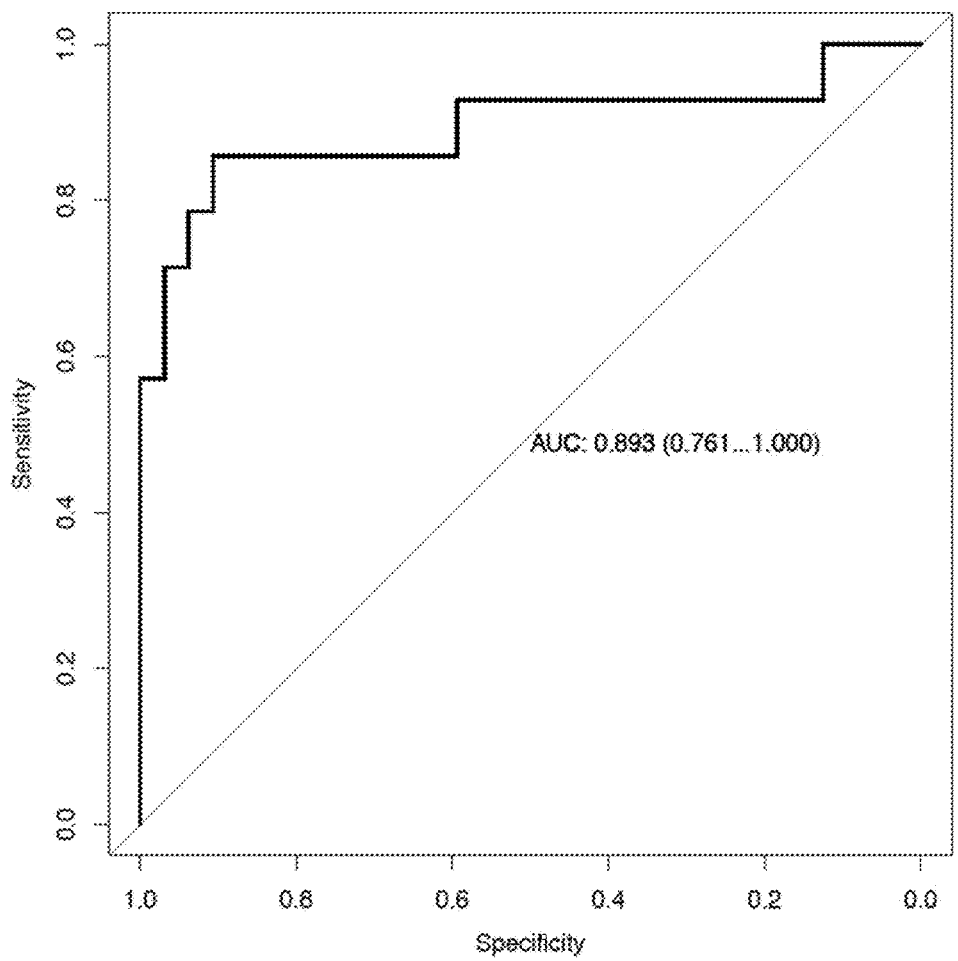
FIG. 22 is a receiver operating characteristic (ROC) curve for applying P(<150) to differentiate HCC patients with greater than 6% tumor DNA fraction and healthy subjects.

FIG. 22, similar to FIG. 21, shows that size analysis with P(<150) can also detect HCC patients with a tumor fraction of greater than 6% in the plasma. The AUC for differentiating these patients from healthy subjects was 0.893 with 95% confidence limits of 0.761 and 1.000.

Figure 23:
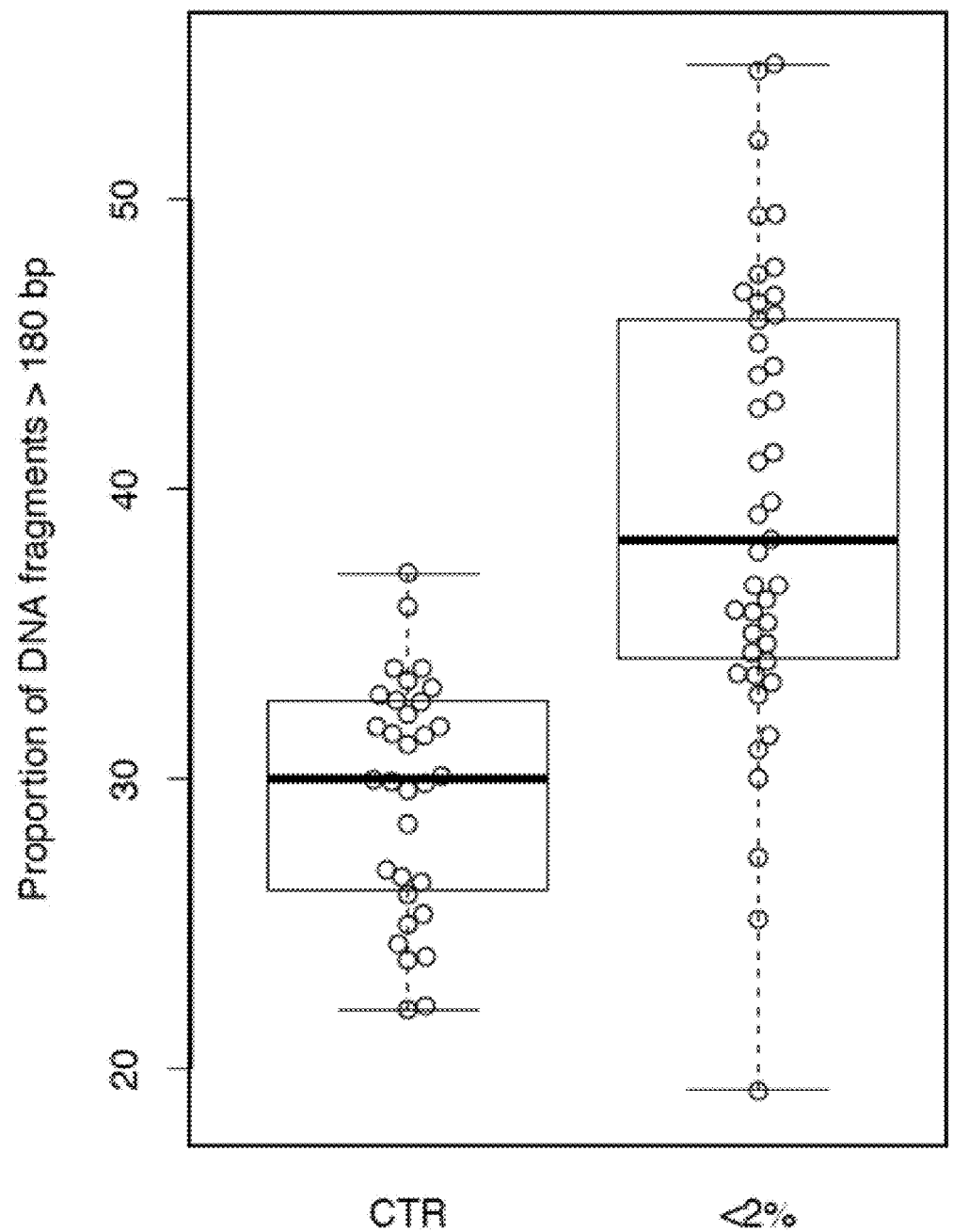
FIG. 23 shows boxplots of the proportion of long fragments for healthy control subjects and HCC patients with tumor DNA fraction of less than 2% in plasma.

FIG. 23 shows that the proportion of long plasma DNA fragments can be used for detecting HCC, as FIG. 20 showed with the proportion short plasma DNA fragments. In this example, the proportion of fragments greater than 180 bp, denoted as P(>180), was plotted for HCC patients with less than 2% and greater than 6% tumor DNA fraction in plasma and healthy control subjects. This proportion was significantly higher in HCC patients with less than 2% tumor DNA fraction (p<0.00001, t-test).

Figure 24:
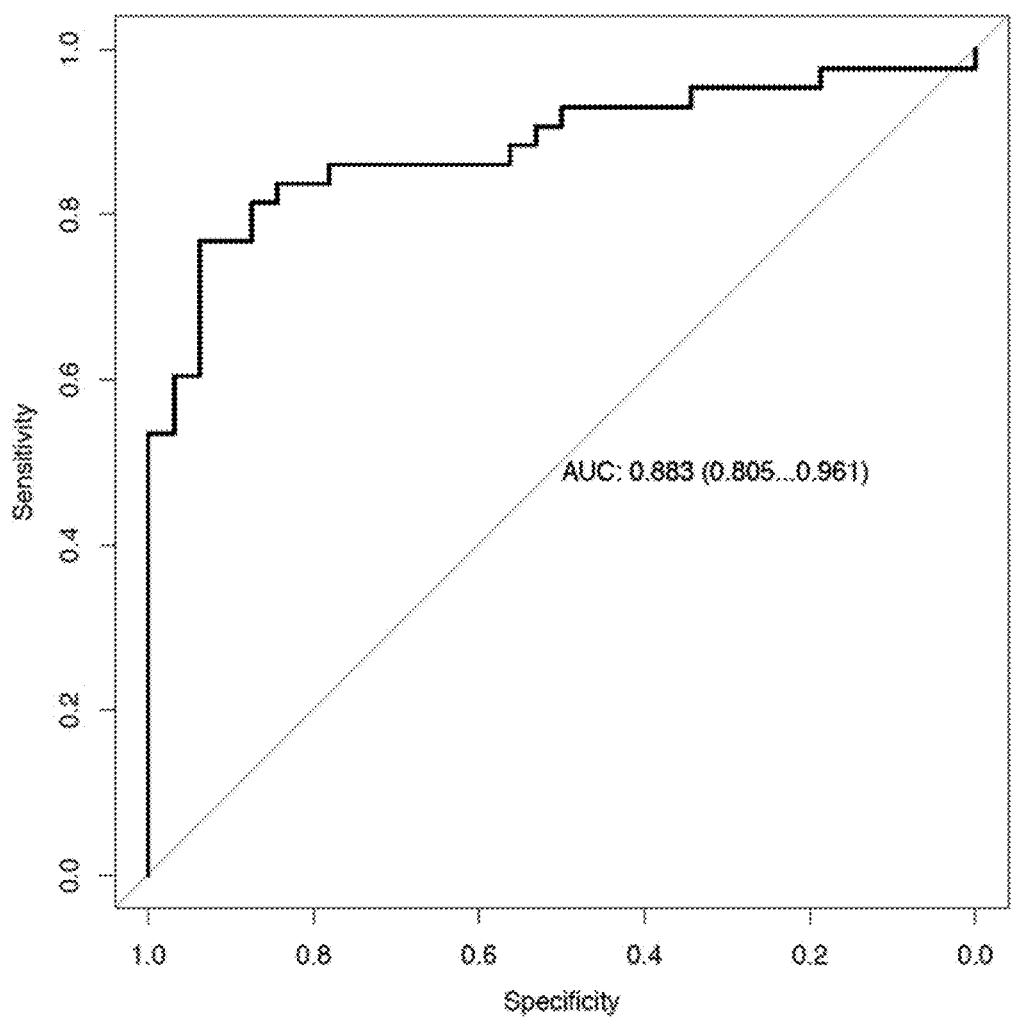
FIG. 24 is an ROC curve for using P(>180) to differentiate HCC patients with less than 2% tumor DNA fraction from healthy control subjects.

FIG. 24 shows an ROC curve for using P(>180) to differentiate HCC patients with less than 2% tumor DNA fraction from healthy control subjects. The AUC was 0.883 with 95% confidence limits of 0.805 and 0.961.

Figure 25:
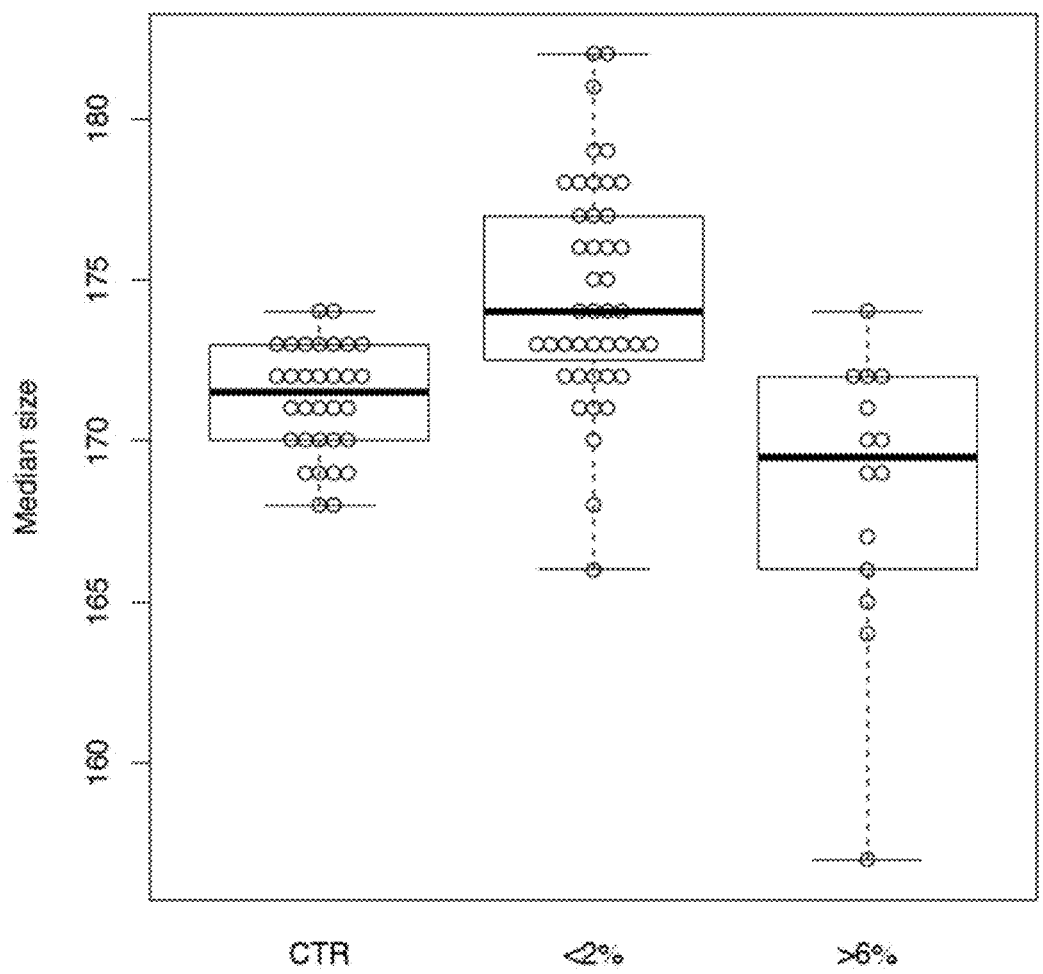
FIG. 25 shows boxplots of median fragment size of healthy control subjects, HCC patients with less than 2% tumor DNA fraction, and HCC patients with greater than 6% tumor DNA fraction.

FIG. 25 provides another example of the different size distributions of DNA fragments with different tumor DNA fractions. FIG. 25 shows boxplots of the median fragment size of healthy control subjects, HCC patients with less than 2% tumor DNA fraction, and HCC patients with greater than 6% tumor DNA fraction. The median size of DNA fragments of the HCC patients with less than 2% tumor DNA fraction were significantly longer (P<0.00001, t-test) than the healthy control subjects. In contrast, the median size of DNA fragments of the HCC patients with greater than 6% tumor DNA fraction were significantly shorter (p=0.03, t-test). FIG. 25 supports the use of DNA fragment size as a way to determine stage of cancer. A longer median size is associated with a smaller tumor DNA fraction, while a shorter median size is associated with a larger tumor DNA fraction. If an individual has a smaller tumor DNA fraction below a first cutoff and a median size above a long size threshold, then early stage cancer may be confirmed. On the other hand, if an individual has a larger tumor DNA fraction above a second cutoff and a median size below a short size threshold, then late stage cancer may be confirmed.

HCC patients with a tumor DNA fraction from 2% to 6% have a median DNA fragments size between HCC patients with a tumor fraction of less than 2% and HCC patients with a tumor fraction greater than 6%. In this manner, HCC patients with the tumor fraction from 2% to 6% may have a distribution similar to the healthy control subjects in FIG. 25. Hence, if an individual has a tumor DNA fraction from the low cutoff to the high cutoff and a median size from a short size threshold to a long size threshold, then middle stage cancer may be confirmed.

Figure 26:
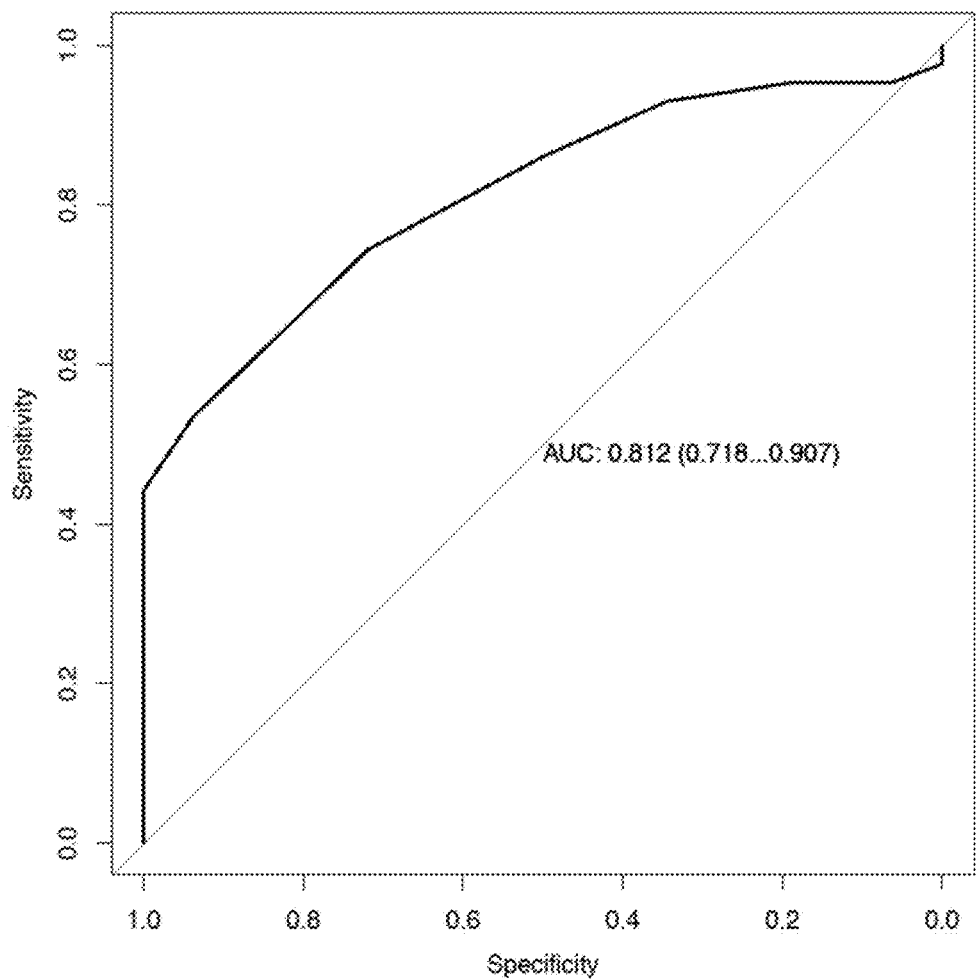
FIG. 26 is an ROC curve for using median fragment size to differentiate between HCC patients with less than 2% tumor DNA fraction and healthy control subjects.
Figure 27:
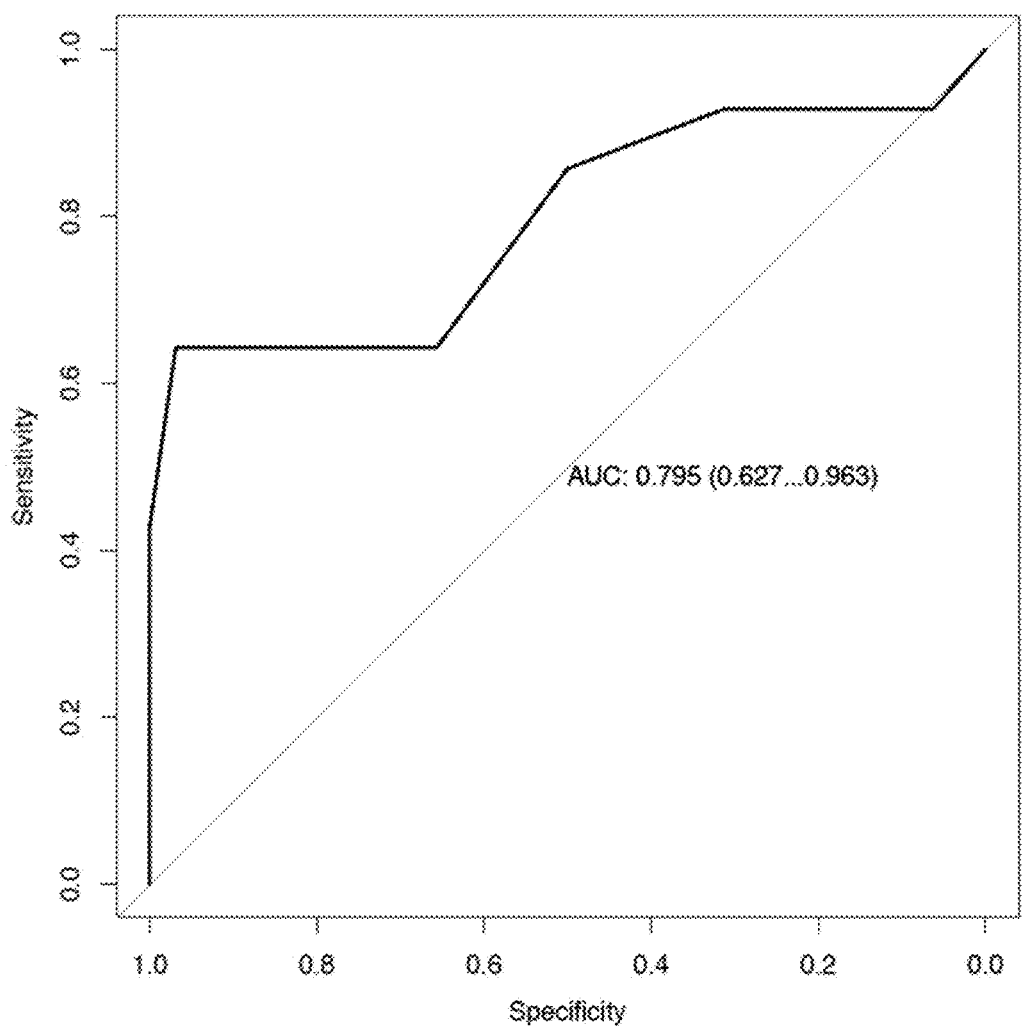
FIG. 27 is an ROC curve for using median fragment size to differentiate between HCC patients with greater than 6% tumor DNA fraction and healthy control subjects.

FIGS. 26 and 27 are ROC curves that show that different size thresholds can be used to differentiate HCC patients from healthy control subjects. FIG. 26 is an ROC curve for using median fragment size to differentiate between HCC patients with less than 2% tumor DNA fraction and healthy control subjects. The AUC was 0.812 with 95% confidence limits of 0.718 and 0.907.

FIG. 27 is an ROC curve for using median fragment size to differentiate between HCC patients with greater than 2% tumor DNA fraction and healthy control subjects. The AUC was 0.795 with 95% confidence limits of 0.627 and 0.963.

Other statistical characteristics of the size distribution (e.g., median, mean, percentile) can be used as a parameter for the differentiation of HCC patients and healthy subjects.

In addition to analyzing the size distribution of plasma DNA fragments arising from all genomic regions, size analysis can also focus on DNA fragments arising from specific genomic regions. A specific genomic region may be a chromosome arm.

Figure 28:
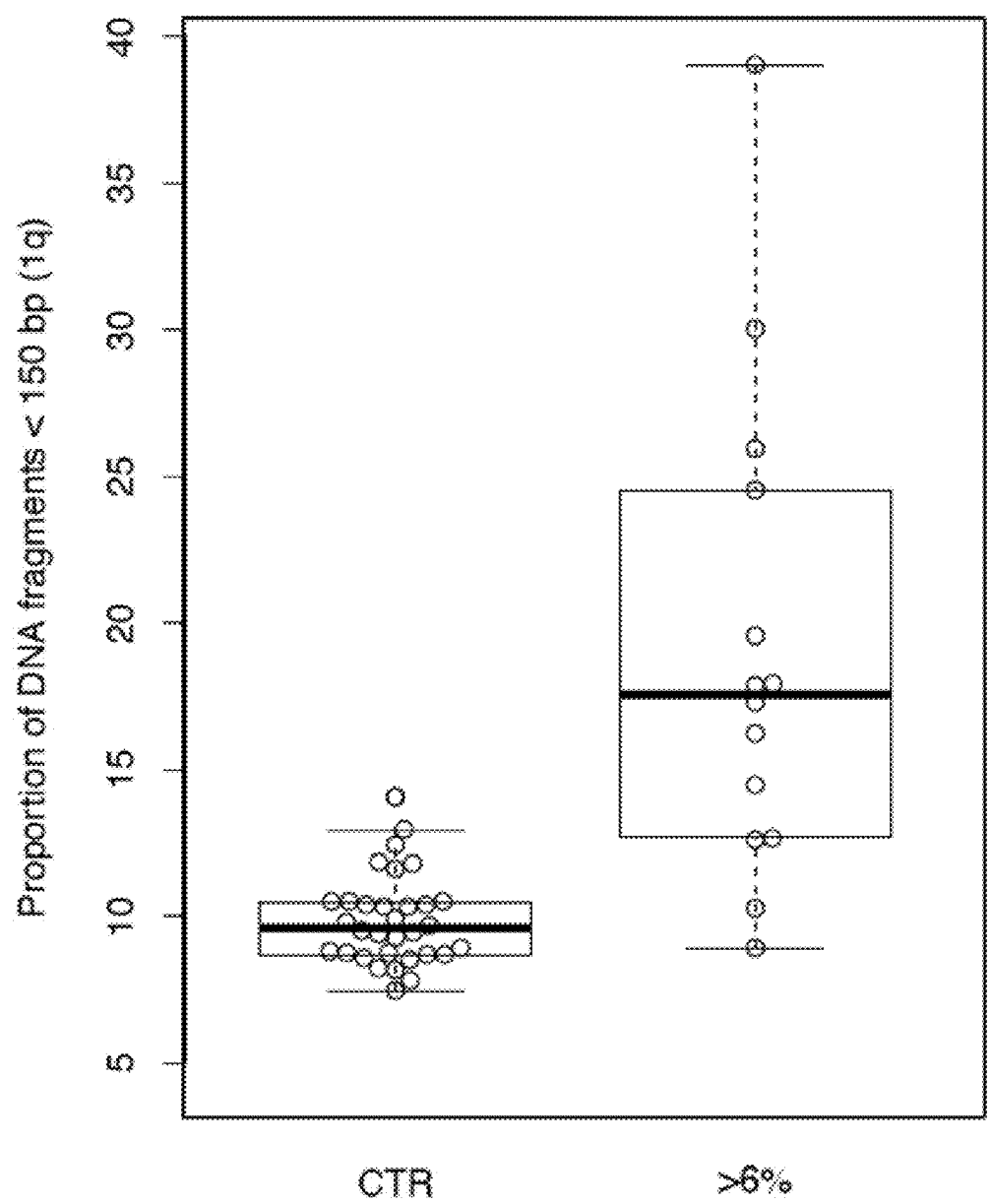
FIG. 28 shows a boxplot of the proportion of short plasma DNA fragments of less than 150 bp that were aligned to chromosome 1q for HCC patients with greater than 6% tumor DNA fraction and for healthy control subjects.

FIG. 28 shows a boxplot of the proportion of short plasma DNA fragments of less than 150 bp that were aligned to chromosome 1q for HCC patients with greater than 6% tumor DNA fraction and for healthy control subjects. The proportion of short fragments was significantly higher (p<0.00001, t-test) in the HCC patients.

Figure 29:
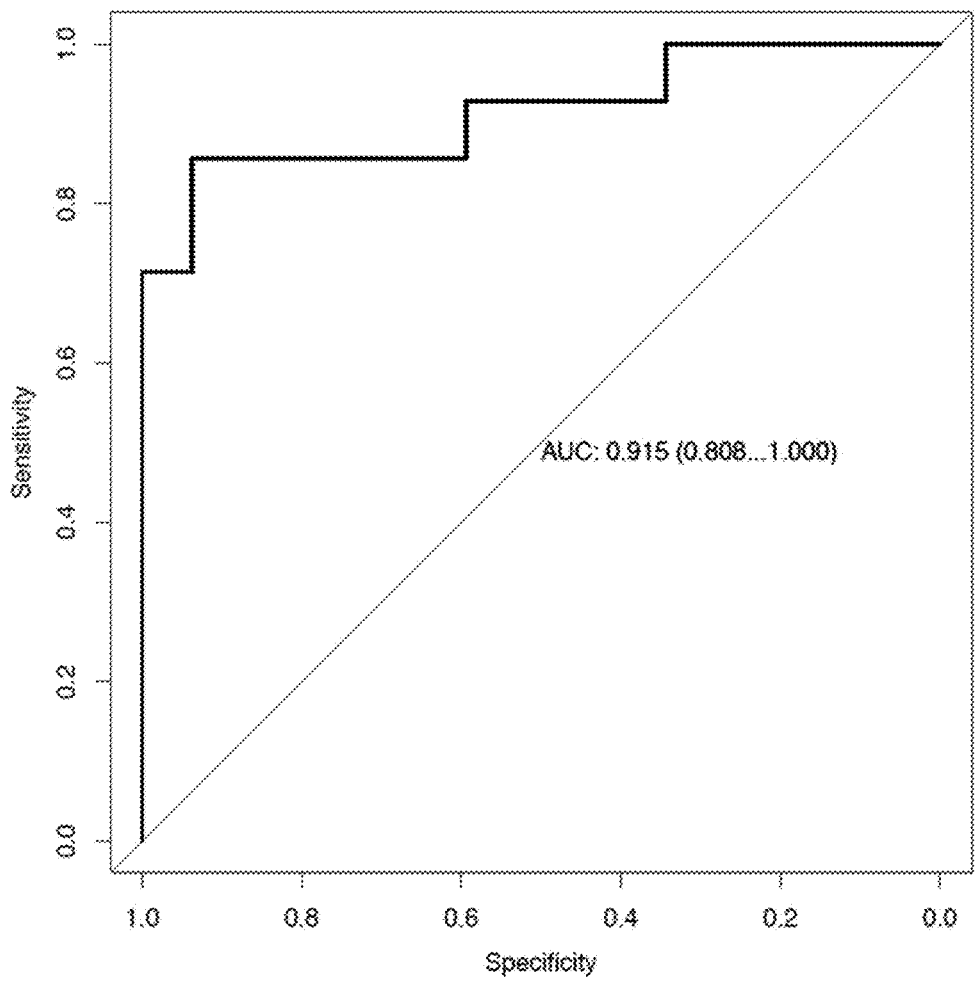
FIG. 29 is an ROC curve for using the proportion of short plasma DNA fragments of less than 150 bp to differentiate between HCC patients with greater than 6% tumor DNA fraction and healthy control subjects.

FIG. 29 is an ROC curve for using the proportion of short plasma DNA fragments of less than 150 bp to differentiate between HCC patients with greater than 6% tumor DNA fraction and healthy control subjects. The AUC was 0.915 with a 95% confidence interval from 0.808 to 1.000.

B. Method

Figure 17:
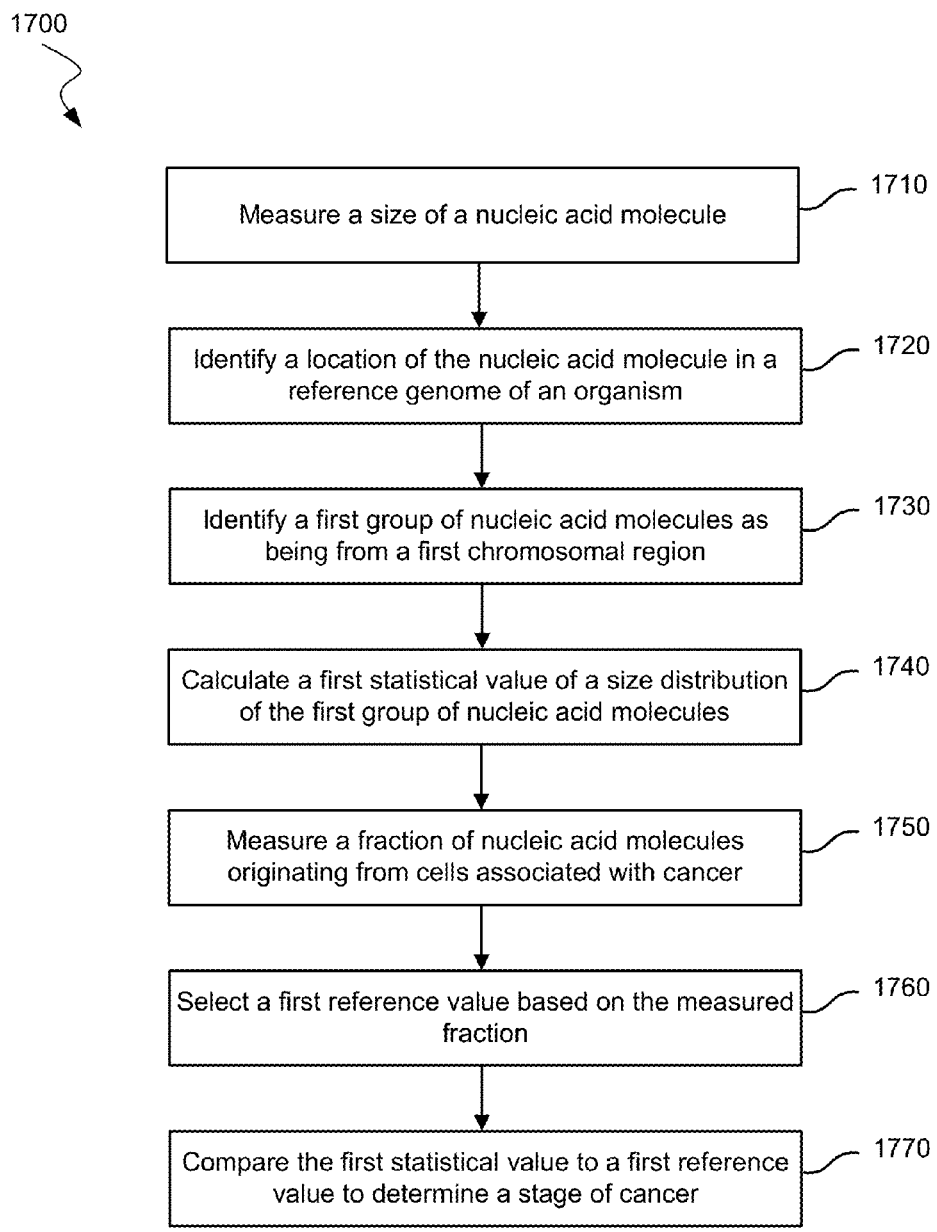
FIG. 17 is a flowchart illustrating a method of analyzing a biological sample of an organism according to embodiments of the present invention.

FIG. 17 is a flowchart illustrating a method 1700 of analyzing a biological sample of an organism according to embodiments of the present invention. The biological sample may include nucleic acid molecules originating from normal cells and from cells associated with cancer. At least some of the nucleic acid molecules are cell-free in the biological sample.

In step 1710, for each of a plurality of the nucleic acid molecules in the biological sample, a size of the nucleic acid molecule is measured. The size of the nucleic acid molecule may be measured similar to step 910 of FIG. 9.

In step 1720, a location of the nucleic acid molecule in a reference genome of the organism is identified. Identifying the location of the nucleic acid molecule may be performed in a similar manner as step 620 of FIG. 6.

In step 1730, a first group of nucleic acid molecules is identified as being from a first chromosomal region based on the identified locations. The first chromosomal region may include a plurality of first loci. Identification of the respective group of nucleic acid molecules may be similar to step 120 of FIG. 1.

In step 1740, a computer system may calculate a first statistical value of a size distribution of the first group of nucleic acid molecules. Calculating the respective amount may be similar to the calculation in step 130 of FIG. 1.

In step 1750, a fraction of nucleic acid molecules originating from cells associated with cancer may be measured. The fraction may be calculated according to methods described in U.S. Patent Publication No. 2013/0040824 entitled "Detection of Genetic or Molecular Aberrations Associated with Cancer" by Lo et al. filed Nov. 30, 2011. The fraction of tumor nucleic acid molecules corresponds to a proportion of the nucleic acid molecules in the sample that are from the tumor(s). The fraction/proportion may be expressed as any percentage or decimal value.

The following examples are methods for the measurement of the fraction of tumor nucleic acids but other methods can be used. The fraction of tumor nucleic acids can be determined based on the magnitude of under-representation (or over-representation) in the plasma for regions exhibiting significant under-representation that is compatible with copy number loss (or copy number gain) in the tumor tissues. Another example is to determine the degree of allelic imbalance on two homologous chromosomes for regions affected by copy number aberrations, e.g., regions with the loss of one copy of the two homologous chromosomes. Another example is to determine the fractional concentration of a cancer-associated mutation, including single nucleotide mutation, deletion of nucleotide(s), and translocation. The tumor fraction may be determined by methods described with FIG. 21 above.

In step 1760, a first reference value based on the measured fraction may be selected. In one example, selecting the first reference value may include selecting a size threshold when the measured fraction is below a cutoff. In another example, selecting the first reference value may include selecting a size threshold when the measured fraction is above a cutoff. In these examples, the cutoffs and the size thresholds may differ and may depend on the value of the measured fraction.

In step 1770, the first statistical value may be compared to a first reference value to determine a stage of cancer of the biological sample. The first statistical value may be any statistical value described herein.

Whether cancer exists can be confirmed based on the size analysis along with the measured fraction of nucleic acid molecules originating from cells associated with cancer. For example, when the measured fraction is below a low cutoff, it can be confirmed whether the size distribution is longer than for healthy controls (e.g., whether the first statistical value is above the size threshold). If the size distribution is longer than for healthy controls, this can confirm an early stage of cancer. Examples of the low cutoff are 0.01, 0.015, 0.02, or 0.025. As another example, when the measured fraction is above a high cutoff, it can be confirmed whether the size distribution is shorter than for healthy controls (e.g., whether the first statistical value is below the size threshold). If the size distribution is shorter for healthy controls, this can confirm a late stage of cancer. Examples of the high cutoff may be a fraction of 0.03, 0.035, 0.04, 0.045, 0.05, 0.055, 0.06, 0.065, or 0.07.

We showed that there were additional populations of shorter and longer DNA molecules in plasma of HCC patients. These data might have resolved the apparent inconsistencies that existed in the literature where groups reported the presence of either an increase in the longer or the shorter DNA molecules in the plasma of cancer patients.

VII. MATERIALS AND METHODS

Techniques used in obtaining the results of FIGS. 2-5 are now discussed. Such techniques can be used in other examples above.

Subjects recruited for study included 90 patients with HCC admitted to the Department of Surgery of the Prince of Wales Hospital, Hong Kong, for tumor resection. All blood samples were collected before operation. Sixty-seven HBV carriers and 36 patients with HBV-related cirrhosis were recruited from the Department of Medicine and Therapeutics of the Prince of Wales Hospital, Hong Kong. All patients gave written informed consent and the study was approved by the institutional review board.

In order to extract DNA and prepare sequence libraries, peripheral blood samples were collected into EDTA-containing tubes. Peripheral blood samples were centrifuged at 1,600 g for 10 min at 4° C. The plasma portion was recentrifuged at 16,000 g for 10 min at 4° C. to obtain cell-free plasma. DNA was extracted from 3 to 4.8 mL of plasma using the QIAamp DSP DNA Blood Mini Kit (Qiagen). The plasma DNA was concentrated with a Speed-Vac Concentrator (Savant DNA120; Thermo Scientific) into a 75-μL final volume per sample. Indexed DNA libraries were prepared by using the Kapa Library Preparation Kit (Kapa Biosystems) following the manufacturer's instructions. The adaptor-ligated DNA was enriched by a 14-cycle PCR using the KAPA HiFi HotStart ReadyMix PCR Kit (Kapa Biosystems). The libraries were then analyzed by a 2100 Bioanalyzer (Agilent) and quantified by the Kapa Library Quantification Kit (Kapa Biosystems) before sequencing.

To sequence and align DNA, each DNA library was diluted and hybridized to a paired-end sequencing flow cell (Illumina). DNA clusters were generated on a cBot cluster generation system (Illumina) with the TruSeq PE Cluster Generation Kit v3 (Illumina), followed by 76×2 cycles of sequencing on a HiSeq 2000 system (Illumina) with the TruSeq SBS Kit v3 (Illumina). Sequencing was performed using a 4-plex protocol. We performed an additional 7 cycles of sequencing to decode the index sequence on each sequenced DNA molecule. Real-time image analysis and base calling were performed using the HiSeq Control Software (HCS) v1.4 and Real Time Analysis (RTA) Software v1.13 (Illumina), by which the automated matrix and phasing calculations were based on the spiked-in PhiX control v3 sequenced with the libraries. After base calling, adapter sequences and low quality bases (i.e. quality score <5) were removed.

For sequencing data analysis, sequences from each lane were assigned to the corresponding samples based on the six-base index sequences. The sequenced reads were then aligned to the non-repeat-masked human reference genome (NCBI build 37/hg19) using the Short Oligonucleotide Alignment Program 2 (SOAP2) (40). Up to two nucleotide mismatches were allowed for each member of the paired-end reads but insertions or deletions were not allowed. Reads mapped to a unique genomic location were used for downstream analyses. Paired-end reads aligned to the same chromosome with a correct orientation and spanning an insert size of ≤600 bp were retained for downstream size analyses. After alignment to the reference human genome, the size of each plasma DNA fragment could be deduced from the coordinates of the nucleotides at the outermost ends of each pair of sequence reads. The first single-end reads were used for CNA analysis. Reads with mapping quality of greater than 30 (i.e. 1 erroneous alignment per 1,000 alignments) using the Bowtie 2 software (41) were accepted.

For performing CAZA analysis for CNA, the entire human genome was divided into 100-kb bins. The GC-corrected read count was determined for each 100-kb bin as reported previously (42). The number of GC-corrected read counts for each chromosome arm of interest was determined by summing all values of each 100-kb bin on the chromosome arm. A z-score statistic was used to determine if the plasma DNA representation in a chromosome arm would be significantly increased or decreased when compared with the reference group. The percentage of sequencing reads mapped to each chromosome arm was calculated and compared with the mean value of the 32 healthy control subjects for the respective chromosome arm. An arm-level z-score was calculated as $$\text{z-score} = \frac{P_{test} - P_{normal}}{SD_{normal}}$$

where $P_{test}$ represents the proportion of fragments mapped to the chromosome arm of interest for the test case; $P_{normal}$ and $SD_{normal}$ represent the mean and SD of the proportion of fragments mapped to the chromosome arm for the healthy controls, respectively. Chromosome arms with z scores of <−3 and >3 were regarded as having CNAs in plasma corresponding to deletions and amplifications, respectively.

The fractional concentration of tumor-derived DNA in the plasma (F) can be calculated as $$F = \frac{|P_{test} - P_{normal}|}{\Delta N / 2 \times P_{normal}}$$

where $P_{test}$ represents the proportion of fragments mapped to the chromosome arm of interest for the test case; $P_{normal}$ represents the mean proportion of fragments mapped to the chromosome arm for the healthy controls and $\Delta N$ represents the copy number change. For cases showing a deletion in at least one chromosome arm, we calculate F based on the deleted chromosome arm(s). As most chromosome arm deletions involve only one of the two homologous chromosomes (33), we assumed a single copy loss for our analysis. For the 24 cases with only chromosome arm amplification but no deletion, F was calculated based on the amplified arm with the assumption of single copy gain.

Sequencing data analysis was performed by using bioinformatics programs written in Perl and R languages. A p-value of <0.05 was considered as statistically significant and all probabilities were two-tailed.

VIII. COMPUTER SYSTEM

Figure 32:
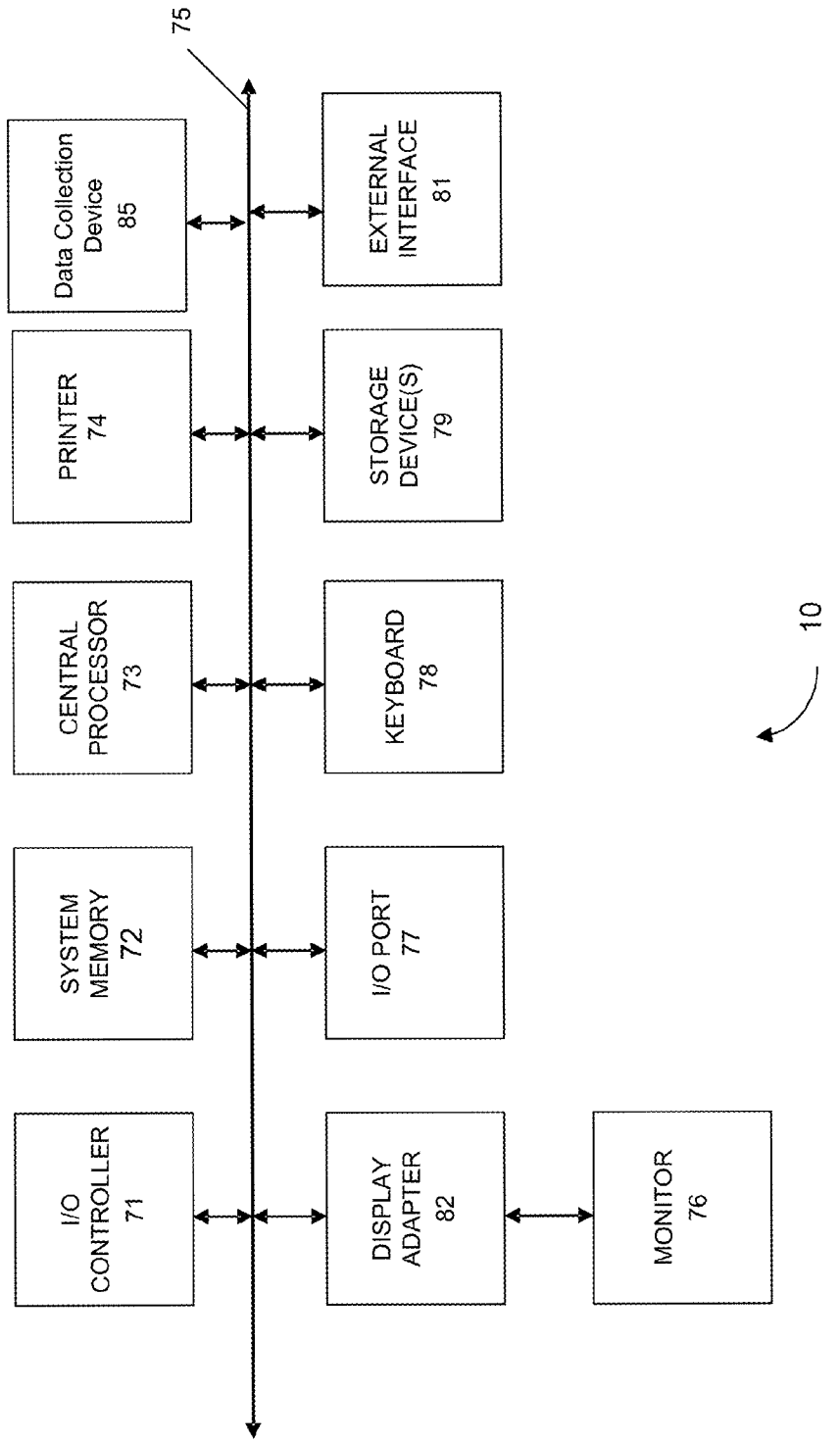
FIG. 32 shows a block diagram of an example computer system 10 usable with system and methods according to embodiments of the present invention.

Any of the computer systems mentioned herein may utilize any suitable number of subsystems. Examples of such subsystems are shown in FIG. 32 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 32 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer apparatus 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

IX. REFERENCES

1. Chan K C A (2013) Scanning for cancer genomic changes in plasma: toward an era of personalized blood-based tumor markers. *Clin Chem* 59(11):1553-1555.
2. Dawson S J, Rosenfeld N, & Caldas C (2013) Circulating tumor DNA to monitor metastatic breast cancer. *N Engl J Med* 369(1):93-94.
3. Bidard F C, Weigelt B, & Reis-Filho J S (2013) Going with the flow: from circulating tumor cells to DNA. *Sci Transl Med* 5(207):207ps214.
4. Chan K C A, et al. (2013) Cancer genome scanning in plasma: detection of tumor-associated copy number aberrations, single-nucleotide variants, and tumoral heterogeneity by massively parallel sequencing. *Clin Chem* 59(1): 211-224.
5. Heitzer E, et al. (2013) Establishment of tumor-specific copy number alterations from plasma DNA of patients with cancer. *Int J Cancer* 133(2):346-356.
6. Heitzer E, et al. (2013) Tumor-associated copy number changes in the circulation of patients with prostate cancer identified through whole-genome sequencing. *Genome Med* 5(4):30.
7. Leary R J, et al. (2012) Detection of chromosomal alterations in the circulation of cancer patients with whole-genome sequencing. *Sci Transl Med* 4(162): 162ra154.
8. Chan K C A, et al. (2013) Noninvasive detection of cancer-associated genome-wide hypomethylation and copy number aberrations by plasma DNA bisulfite sequencing. *Proc Natl Acad Sci USA* 110(47): 18761-18768.
9. Chan K C A, et al. (2008) Quantitative analysis of circulating methylated DNA as a biomarker for hepatocellular carcinoma. *Clin Chem* 54(9):1528-1536.
10. Wong I H, et al. (1999) Detection of aberrant p16 methylation in the plasma and serum of liver cancer patients. *Cancer Res* 59(1):71-73.
11. Balgkouranidou I, et al. (2014) Breast cancer metastasis suppressor-1 promoter methylation in cell-free DNA provides prognostic information in non-small cell lung cancer. *Br J Cancer* 110(8):2054-2062.
12. Diehl F, et al. (2005) Detection and quantification of mutations in the plasma of patients with colorectal tumors. *Proc Natl Acad Sci USA* 102(45):16368-16373.
13. Yung T K F, et al. (2009) Single-molecule detection of epidermal growth factor receptor mutations in plasma by microfluidics digital PCR in non-small cell lung cancer patients. *Clin Cancer Res* 15(6):2076-2084.
14. Murtaza M, et al. (2013) Non-invasive analysis of acquired resistance to cancer therapy by sequencing of plasma DNA. *Nature* 497(7447):108-112.
15. Forshew T, et al. (2012) Noninvasive identification and monitoring of cancer mutations by targeted deep sequencing of plasma DNA. *Sci Transl Med* 4(136):136ra168.
16. Lo Y M D, et al. (1999) Quantitative analysis of cell-free Epstein-Barr virus DNA in plasma of patients with nasopharyngeal carcinoma. *Cancer Res* 59(6):1188-1191.
17. Chan K C A, et al. (2013) Early detection of nasopharyngeal carcinoma by plasma Epstein-Barr virus DNA analysis in a surveillance program. *Cancer* 119(10):1838-1844.
18. McBride D J, et al. (2010) Use of cancer-specific genomic rearrangements to quantify disease burden in plasma from patients with solid tumors. *Genes, Chromosomes & Cancer* 49(11):1062-1069.
19. Leary R J, et al. (2010) Development of personalized tumor biomarkers using massively parallel sequencing. *Sci Transl Med* 2(20):20ra14.
20. Chan K C A, Leung S F, Yeung S W, Chan A T C, & Lo Y M D (2008) Persistent aberrations in circulating DNA integrity after radiotherapy are associated with poor prognosis in nasopharyngeal carcinoma patients. *Clin Cancer Res* 14(13):4141-4145.
21. Gao Y J, et al. (2010) Increased integrity of circulating cell-free DNA in plasma of patients with acute leukemia. *Clin Chem Lab Med* 48(11):1651-1656.
22. Umetani N, et al. (2006) Increased integrity of free circulating DNA in sera of patients with colorectal or periampullary cancer: direct quantitative PCR for ALU repeats. *Clin Chem* 52(6):1062-1069.
23. Wang B G, et al. (2003) Increased plasma DNA integrity in cancer patients. *Cancer Res* 63(14):3966-3968.
24. Umetani N, et al. (2006) Prediction of breast tumor progression by integrity of free circulating DNA in serum. *J Clin Oncol* 24(26):4270-4276.
25. Schwarzenbach H, et al. (2012) Loss of heterozygosity at tumor suppressor genes detectable on fractionated circulating cell-free tumor DNA as indicator of breast cancer progression. *Clin Cancer Res* 18(20):5719-5730.

26. Lo Y M D, et al. (2010) Maternal plasma DNA sequencing reveals the genome-wide genetic and mutational profile of the fetus. *Sci Transl Med* 2(61):61ra91.
27. Zheng Y W L, et al. (2012) Nonhematopoietically derived DNA is shorter than hematopoietically derived DNA in plasma: a transplantation model. *Clin Chem* 58(3):549-558.
28. Yu S C Y, et al. (2014) Size-based molecular diagnostics using plasma DNA for noninvasive prenatal testing. *Proc Natl Acad Sci USA* 111(23):8583-8588.
29. Pleasance E D, et al. (2010) A comprehensive catalogue of somatic mutations from a human cancer genome. *Nature* 463(7278):191-196.
30. Fujimoto A, et al. (2012) Whole-genome sequencing of liver cancers identifies etiological influences on mutation patterns and recurrent mutations in chromatin regulators. *Nat Genet* 44(7): 760-764.
31. Tao Y, et al. (2011) Rapid growth of a hepatocellular carcinoma and the driving mutations revealed by cell-population genetic analysis of whole-genome data. *Proc Natl Acad Sci USA* 108(29):12042-12047.
32. Totoki Y, et al. (2011) High-resolution characterization of a hepatocellular carcinoma genome. *Nat Genet* 43(5): 464-469.
33. Beroukhim R, et al. (2010) The landscape of somatic copy-number alteration across human cancers. *Nature* 463(7283):899-905.
34. Chiang D Y, et al. (2008) Focal gains of VEGFA and molecular classification of hepatocellular carcinoma. *Cancer Res* 68(16):6779-6788.
35. Kan Z, et al. (2013) Whole-genome sequencing identifies recurrent mutations in hepatocellular carcinoma. *Genome Res* 23(9):1422-1433.
36. Kim T M, et al. (2008) Clinical implication of recurrent copy number alterations in hepatocellular carcinoma and putative oncogenes in recurrent gains on 1q. *Int J Cancer* 123(12):2808-2815.
37. Nakano H & Shinohara K (1994) X-ray-induced cell death: apoptosis and necrosis. *Radiation Research* 140 (1):1-9.
38. Walker N I, Harmon B V, Gobe G C, & Kerr J F (1988) Patterns of cell death. *Methods and Achievements in Experimental Pathology* 13:18-54.
39. Alexandrov L B, et al. (2013) Signatures of mutational processes in human cancer. *Nature* 500(7463):415-421.
40. Li R, et al. (2009) SOAP2: an improved ultrafast tool for short read alignment. *Bioinformatics* 25(15):1966-1967.
41. Langmead B & Salzberg S L (2012) Fast gapped-read alignment with Bowtie 2. *Nature Methods* 9(4):357-359.
42. Chen E Z, et al. (2011) Noninvasive prenatal diagnosis of fetal trisomy 18 and trisomy 13 bp maternal plasma DNA sequencing. *PLoS One* 6(7):e21791.

What is claimed is:

1. A method of analyzing a biological sample of an organism, the biological sample including nucleic acid molecules originating from normal cells and potentially from cells associated with cancer, wherein at least some of the nucleic acid molecules are cell-free in the biological sample, the method comprising:
    identifying a plurality of chromosomal regions of the organism, each chromosomal region including a plurality of loci;
    for each of a plurality of the nucleic acid molecules in the biological sample:
        measuring a size of the nucleic acid molecule; and
        identifying a location of the nucleic acid molecule in a reference genome of the organism;
    for each of the plurality of chromosomal regions:
        identifying a respective group of nucleic acid molecules as being from the chromosomal region based on the identified locations, the respective group including at least one nucleic acid molecule located at each of the plurality of loci of the chromosomal region;
        calculating, with a computer system, a respective amount of the respective group of nucleic acid molecules; and
        comparing the respective amount to a count reference value to determine a count classification of whether the chromosomal region exhibits an aberration, the count classification for a first chromosomal region of the plurality of chromosomal regions indicating a first aberration;
    identifying a first group of nucleic acid molecules as being from the first chromosomal region based on the identified locations;
    calculating, with a computer system, a first statistical value of a first size distribution of the first group of nucleic acid molecules;
    comparing the first statistical value to a size reference value to determine a size classification of whether the first chromosomal region exhibits the first aberration;
    determining a final classification of whether the first chromosomal region exhibits the first aberration using the count classification and the size classification of the first chromosomal region; and
    determining whether cancer exists in the organism using the final classification.

2. The method of claim 1, wherein the final classification is that the first aberration exists only when the count classification and the size classification indicate a same aberration.

3. The method of claim 1, wherein the plurality of chromosomal regions are non-overlapping.

4. The method of claim 1, wherein the final classification is that the first aberration exists, the method further comprising:
    obtaining a calibration function that provides a relationship between a size of a tumor and the first statistical value; and
    determining the size of the tumor using the calibration function.

5. The method of claim 4, wherein the calibration function is determined from calibration data points of reference samples from organisms with tumors of known size, wherein a calibration data point includes a measurement of the size of the tumor and a corresponding statistical measurement of sizes of nucleic acid molecules from the first chromosomal region.

6. The method of claim 1, wherein the respective value comprises a mean of the first size distribution, a median of the first size distribution, a mode of the of the first size distribution, or a proportion of nucleic acid molecules having a size below a size threshold.

7. The method of claim 1, wherein the size reference value corresponds to a second statistical value of a second size distribution of a second chromosomal region.

8. The method of claim 7, wherein comparing the first statistical value to the size reference value includes:
    determining a separation value between the first statistical value and the size reference value; and
    comparing the separation value to a threshold value.

9. The method of claim 1, further comprising:
   determining a set of size classifications for a set of chromosomal regions identified as aberrant based on corresponding count classifications; and
   confirming whether the set of chromosomal regions are aberrant based on the set of size classifications.

10. A computer product comprising a computer readable medium storing a plurality of instructions for controlling a computer system to perform a method, the method comprising:
   identifying a plurality of chromosomal regions of the organism, each chromosomal region including a plurality of loci;
   for each of a plurality of the nucleic acid molecules in the biological sample:
      measuring a size of the nucleic acid molecule; and
      identifying a location of the nucleic acid molecule in a reference genome of the organism;
   for each of the plurality of chromosomal regions:
      identifying a respective group of nucleic acid molecules as being from the chromosomal region based on the identified locations, the respective group including at least one nucleic acid molecule located at each of the plurality of loci of the chromosomal region;
      calculating, with a computer system, a respective amount of the respective group of nucleic acid molecules; and
      comparing the respective amount to a count reference value to determine a count classification of whether the chromosomal region exhibits an aberration, the count classification for a first chromosomal region of the plurality of chromosomal regions indicating a first aberration;
   identifying a first group of nucleic acid molecules as being from the first chromosomal region based on the identified locations;
   calculating, with a computer system, a first statistical value of a first size distribution of the first group of nucleic acid molecules;
   comparing the first statistical value to a size reference value to determine a size classification of whether the first chromosomal region exhibits the first aberration;
   determining a final classification of whether the first chromosomal region exhibits the first aberration using the count classification and the size classification of the first chromosomal region; and
   determining whether cancer exists in the organism using the final classification.

11. The method of claim 1, further comprising:
   for each of the plurality of chromosomal regions:
      identifying a respective group of nucleic acid molecules as being from the chromosomal region based on the identified locations,
      calculating, with a computer system, a respective statistical value of a respective size distribution of the respective group of nucleic acid molecules,
      comparing the respective statistical value to the size reference value to determine a size classification of whether the chromosomal region exhibits the aberration, and
      determining a respective final classification of whether the chromosomal region exhibits the aberration using the respective count classification and the respective size classification of the chromosomal region.

12. The method of claim 11, wherein the count classification for each of the plurality of chromosomal regions is that the chromosomal region exhibits an aberration.

13. The method of claim 11, wherein determining whether cancer exists in the organism comprises:
   determining an amount of chromosomal regions exhibiting an aberration; and
   comparing the amount of chromosomal regions to a threshold.

* * * * *